US007211395B2

(12) United States Patent
Sato et al.

(10) Patent No.: US 7,211,395 B2
(45) Date of Patent: May 1, 2007

(54) SERUM ALBUMIN BINDING MOIETIES

(75) Inventors: Aaron K. Sato, Somerville, MA (US);
Arthur C. Ley, Newton, MA (US);
Edward H. Cohen, Belmont, MA (US)

(73) Assignee: Dyax Corp., Cambridge, MA (US)

( * ) Notice: Subject to any disclaimer, the term of this patent is extended or adjusted under 35 U.S.C. 154(b) by 652 days.

(21) Appl. No.: 10/094,401

(22) Filed: Mar. 8, 2002

(65) Prior Publication Data
US 2003/0069395 A1   Apr. 10, 2003

Related U.S. Application Data

(60) Provisional application No. 60/292,975, filed on May 23, 2001, provisional application No. 60/331,352, filed on Mar. 9, 2001.

(51) Int. Cl.
G01N 33/53 (2006.01)
A61K 38/00 (2006.01)

(52) U.S. Cl. .................... 435/7.1; 436/501; 530/300; 530/350; 530/363

(58) Field of Classification Search ................. 530/300, 530/350, 363; 435/7.1; 436/501
See application file for complete search history.

(56) References Cited

U.S. PATENT DOCUMENTS

| 5,116,944 | A | 5/1992 | Sivam et al. |
| 5,223,409 | A | 6/1993 | Ladner et al. |
| 5,538,897 | A | 7/1996 | Yates, III et al. |
| 5,767,243 | A | 6/1998 | Lichenstein et al. |
| 5,780,594 | A * | 7/1998 | Carter ................. 530/363 |
| 5,830,858 | A | 11/1998 | Rosenthal |
| 5,834,318 | A | 11/1998 | Buettner |
| 5,958,736 | A | 9/1999 | Ståhl et al. |
| 6,177,542 | B1 | 1/2001 | Ruoslahti et al. .......... 530/326 |
| 6,919,424 | B2 | 7/2005 | Rondon et al. |
| 2002/0019350 | A1 | 2/2002 | Levine et al. |
| 2002/0146750 | A1 | 10/2002 | Hoogenboon et al. |
| 2002/0164667 | A1 | 11/2002 | Alitalo et al. |
| 2003/0069395 | A1 | 4/2003 | Sato et al. |
| 2003/0104591 | A1 | 6/2003 | Murray |
| 2004/0009534 | A1 | 1/2004 | Sato et al. |
| 2004/0071705 | A1 | 4/2004 | Sato et al. |
| 2005/0250700 | A1 | 11/2005 | Sato et al. |

FOREIGN PATENT DOCUMENTS

| EP | 0 395 918 A2 | 11/1990 |
| EP | 0 395918 | 11/1990 |
| WO | WO 01/01743 | 2/1991 |
| WO | WO 91/01743 | 2/1991 |
| WO | WO 92/12236 | 7/1992 |
| WO | WO 00/37501 | 6/2000 |
| WO | WO 01/45746 | 6/2001 |
| WO | WO 03/074005 | 9/2003 |

OTHER PUBLICATIONS

Sequence Alignment Results for SEQ ID No. 4, p. 2.*
Sato et al. Biotechnology Prog. 2002, 18, 182-192.*
Briggs et al. (European Journal of Cancer, 1993, vol. 29A, No. 2, pp. 230-237).*
Adams, P. et al., "Heme-Peptide/Protein Interactions: The Binding of Heme Octa and Undecapeptides, and Microperoxidase-8 and -11, to Human Serum Albumin," *J. Inorg. Biochem.*, 37:91-103, (1989).
Arakawa, T. and Kita, Y., "Stabilizing Effects of Caprylate and acetyltryptophanate on Heat-Induced Aggregation of Bovine Serum Albumin," *Biochim. Biophy. Acta*, 1479:32-36, (2000).
Chhabra, S. et al., "An Appraisal of New Variants of Dde Amine Protecting Group for Solid Phase Peptide Synthesis," *Tetrahedron Lett.*, 39:1603-1606, (1998).
Cheruvallath, V. et al., "The effect of Octanoic Acid on the Binding of the Enantiomers of Ibuprofen and Naproxen to Human Serum Albumin: A Chromatographic Implication," *Pharm. Res.*, 13:173-178, (1996).
Hollon, T., "HGS Targets Patent-Expiring Drugs," *Nat. Biotechnol.*, 18:1238-1239, (2000).
Kobayashi, K. et al., "The Development of Recombinant Human Serum Albumin," *Ther. Apher*, 2:257-262, (1998).
Kragh-Hansen, U., "Octanoate Binding to the Indole- and Benzodiazepine-Binding Region of Human Serum Albumin," *Biochem. J.*, 273:641-644, (1991).
Luik, A. et al., "Study of Human Serum Albumin Structure by Dynamic Light Scattering: Two Types of Reactions Under Different pH and Interaction With Physiologically Active Compounds," *Spectrochim. Acta Part A*, 54:1503-1507, (1998).
Mahany, T. et al., "Studies on the Affinity Chromatography of Serum Albumins from Human and Animal Plasmas," *Comp. Biochem, Physiol.*, 68B:319-323, (1981).
Merrifield, R., "Solid Phase Peptide Synthesis. I. The Synthesis of a Tetrapeptide," *J. Am. Chem. Soc.*, 85:2149-2154, (1963).
Norde, W. and Giacomelli, C., "BSA Structural Changes During Homomolecular Exchange Between the Adsorbed and the Dissolved States," *J. Biotechnol.*, 79:259-268, (2000).
Pingali, A. et al., "Peptides as Affinity Surfaces for Protein Purification," *J. Mol. Recognit.*, 9:426-432, (1996).
Ross, P. et al., "Thermal Stability of Human Albumin Measured by Differential Scanning Calorimetry," *Vox Sang.*, 47:19-27, (1984).
Saeed, M. et al., "Blood Pool MR Contrast Agents for Cardiovascular Imaging," *J. Magn. Reson. Imaging*, 12:890-898, (2000).
Seabold, J., "Radionuclide Venography and Labeled Platelets in Deep Venous Thrombosis," *Semin. Nucl. Med.*, 31:124-128, (2001).
Shani, M. et al., "Expression of Human Serum Albumin in the Milk of Transgenic Mice," *Transgenic Res.*, 1:195-208, (1992).

(Continued)

Primary Examiner—Long V. Le
Assistant Examiner—Lisa V Cook
(74) Attorney, Agent, or Firm—Fish & Richardson P.C.

(57) ABSTRACT

Compositions comprising non-naturally occurring serum albumin binding moieties are described, together with methods of use thereof, e.g., for detecting or isolating serum albumin molecules in a solution, for blood circulation imaging, and for linking therapeutics or other molecules to albumin. Preferred serum albumin binding peptides having a high affinity for human serum albumin are particularly disclosed.

20 Claims, 4 Drawing Sheets

OTHER PUBLICATIONS

Shrake, A. et al., "Thermal Stability of Human Albumin Measured by Differential Scanning Calorimetry," *Vox Sang.*, 47:7-18, (1984).

Sijmons, P. et al., "Production of Correctly Processed Human Serum Albumin in Transgenic Plants," *Biotechnology*, 8:217-221, (1990).

Yeh, P. et al., "Design of Yeast-Secreted Albumin Derivatives for Human Therapy: Biological and Antiviral Properties of a Serum Albumin-CD4 Genetic Conjugate," *Proc. Natl. Acad. Sci. USA*, 89:1904-1908, (1992).

Szekerke, M. et al., "A New Approach to the Study of the Contribution of Peptide Carriers to Antitumor Activity: Binding of the Peptide Moiety to Human Serum Albumin," *FEBS Letters*, 44:160-163, (1974).

Akerstrom et al., "Definition of IgG- and Albumin-binding Regions of Streptococcal Protein G*". *Journal of Biological Chemistry* 262(28):13388-13391 (1987).

Burger et al. "Pre-Clinical Evaluation of a Methotrexate-Albumin Conjugate (MTX-HSA) in Human Tumor Xenografts in Vivo" *International Journal of Cancer* 92:718-724 (2001).

Sato et al., "Development of Mammalian Serum Albumin Affinity Purification Media by Phage Display." *Biotechnol. Prog.* 18:182-192 (2002).

Venerando et al., "Interactions of Ganglioside $G_{M1}$ with Human and Fetal Calf Sera Formation of Ganglioside-Serum Albumin Complexes", *Biochimica et Biophysica Acta* 692: 18-26 (1982).

Yousif et al., "Staphylococcal Neutral Phosphatase: A highly cataonic molecule with binding properties for immunoglobulin", *APMIS* 102: 891-900 (1994).

U.S. Appl. No. 60/331,352, by inventors Aaron K. Sato, Arthur C. Ley and Edward H. Cohen, filed Feb. 11, 2002.

U.S. Appl. No. 60/292,975, by inventors Aaron K. Sato, Arthur C. Ley and Edward H. Cohen, filed May 23, 2001.

Birn H et al. "Cubilin is an albumin binding protein important for renal tubular albumin reabsorption" *The Journal of Clinical Investigation*, vol. 105, No. 10:pp. 1353-1361 (2000).

Cuozzo J W et al. "Competition between glutathione and protein thiols for disulphide-bond formation" *Nature Cell Biology*, vol. 1, No. 3:pp. 130-135 (1999).

Mehta A I et al "Biomarker Amplification by Serum Carrier Protein Binding" *Disease Markers*, vol. 19, No. 1:pp. 1-10 (2003).

Rajkovic Vvan A Erefili Valiontis et al. "Direct quantitation of growth hormone binding protein in human serum by a ligand immunofunctional assay: Comparison with immunoprecipitation and chromatographic methods" *Journal of Clinical Endocrinology and Metabolism*, vol. 78, No. 3:pp. 772-777 (1994).

Sjobring U "Isolation and molecular characterization of a novel albumin-binding protein from group *G streptococci*" *Infection and Immunity*, American Society of Microbiology, vol. 60, No. 9::pp. 3601-3608 (1992).

Supplementary Partial European Search Report (Oct. 18, 2005).

Sequence Alignment Results for SEQ ID No. 4, p. 2 dated Apr. 8, 2005 from U.S. Appl. No. 10/094,401.

Robert C. Ladner, "Constrained peptides as binding entities," TIBTECH, Oct. 13, 1995: 426-430.

* cited by examiner

SERUM ALBUMIN BINDING MOIETIES

CROSS-REFERENCE TO RELATED APPLICATIONS

Applicants claim the benefit under 35 U.S.C. §119 of the previously filed U.S. provisional applications Ser. No. 60/331,352 filed Mar. 9, 2001 and Ser. No. 60/292,975 filed May 23, 2001.

FIELD OF THE INVENTION

This invention provides polypeptides that bind to serum albumin, in particular human serum albumin (HSA), and methods for their use, for example, in purification and for medical uses.

BACKGROUND OF THE INVENTION

The most abundant protein component in circulating blood of mammalian species is serum albumin, which is normally present at a concentration of approximately 3 to 4.5 grams per 100 milliters of whole blood. Serum albumin is a blood protein of approximately 70,000 daltons which provides several important functions in the circulatory system. For instance, it functions as a transporter of a variety of organic molecules found in the blood, as the main transporter of various metabolites such as fatty acids and bilirubin through the blood, and, owing to its abundance, as an osmotic regulator of the circulating blood. Human serum albumin (HSA) has been used clinically in protein replacement therapy and as a plasma expander for patients that have experienced blood loss, e.g., resulting from surgery, burns, trauma, or shock.

Since patients often receive large quantities of HSA in a single treatment, commercial HSA must have a higher degree of purity than many other proteins used therapeutically. The protein must also have the correct conformation to avoid antigenic responses.

HSA is obtained in useful quantities either by purification from human serum derived from human blood donors or by expression and isolation from a recombinant expression system, e.g., transgenic murine milk (Shani et al., *Tranasgenic Res.*, 1: 195–208 (1992)), *Pichia pastoris* (Kobayashi et al., *Ther. Apher*, 2: 257–262 (1998)), and transgenic leafy or tuber plants, such as tobacco and potato plants (Sijmons et al., *Biotechnology (NY)*, 8: 217–221 (1990)). Since HSA harvested from human serum must be purified away from any possible human pathogens and then scrupulously tested, recombinant sources have a tremendous advantage in that they lack such transmissible pathogens.

In research and assay protocols, serum albumin has found a variety of uses. For example, serum albumin is used as a component in various tissue culture growth media to grow eukaryotic, and especially mammalian, cells. Serum albumin may also be used as a blocking protein in various assay protocols, such as in enzyme-linked immunosorbent assays (ELISAs) and Western immunoblots, to prevent potential interference due to non-specific binding by other molecules. In addition, serum albumin may also be used as a carrier molecule to which antigens may be adsorbed or conjugated to form immunogenic compounds, which elicit antibody production to the particular antigen. The size of serum albumin also makes it useful as a standard molecular weight marker protein, which may be used to estimate or calculate the size of other proteins by comparison.

Clearly, serum albumin is a protein that has found and will continue to find use in a wide variety of medicinal, diagnostic, and research applications. Of particular importance is the demand for highly purified serum albumin, especially highly purified HSA. Typically, methods of obtaining highly purified preparations of HSA include a step that uses affinity chromatography with a dye conjugated to a matrix or resin, such as Cibacron Blue SEPHAROSE® affinity matrix (Amersham Pharmacia Biotech, Upsala, Sweden). However, current dye-based affinity chromatography is not able to provide highly purified HSA in a single step and, therefore, requires additional steps that increase production time and costs.

Accordingly, there is a continuing need for the means and methods for producing serum albumins, and especially HSA, in a highly purified state and in greater yield using fewer production steps. In addition, needs remain for means and methods to more thoroughly remove or trap serum albumins from a solution, including whole blood, in various processes and production methods.

SUMMARY OF THE INVENTION

The invention described herein provides the means and methods for producing highly purified preparations of serum albumin or detecting serum albumin by providing a group of non-naturally occurring serum albumin binding moieties, which bind one or more types of mammalian serum albumins, including human serum albumin (HSA). Serum albumin binding moieties of the invention comprise a serum albumin binding polypeptide described herein; phage, phagemids, bacteria, host cells or other replicable genetic packages displaying a serum albumin binding polypeptide described herein, and molecules that comprise a serum albumin binding polypeptide described herein further linked (covalently or non-covalently) to other molecules (such as other polypeptides, detectable molecular tags, etc.).

Utilizing phage display technology, recombinant bacteriophage displaying non-natural, small cyclic polypeptides that specifically bind mammalian serum albumin have been identified and isolated. The phage products and isolated polypeptides have proved to be valuable reagents for specifically binding serum albumin in various solutions, including whole blood and fractions thereof.

In specific embodiments, the invention provides serum albumin binding polypeptides, albumin separation media, and methods for detecting, isolating and purifying mammalian serum albumin from solutions, particularly whole blood, blood serum, other blood fractions, and other mixtures (e.g., conditioned media) containing serum albumin. Preferred features of the invention include recombinant bacteriophage (including phagemids), bacteria, mammalian host cells or other replicable genetic packages expressing exogenous deoxyribonucleic acid (DNA) encoding serum albumin binding polypeptides, which are displayed on the surface of the phage particles.

The invention also provides a non-naturally occurring, serum albumin binding moiety comprising a polypeptide comprising the amino acid sequence of:

Cys-$Xaa_1$-$Xaa_2$-$Xaa_3$-$Xaa_4$-Cys (SEQ ID NO: 1), wherein $Xaa_1$ is Asp, Asn, Ser, Thr, or Trp;

$Xaa_2$ is Asn, Gln, His, Ile, Leu, or Lys;

$Xaa_3$ is Ala, Asp, Phe, Trp, or Tyr; and $Xaa_4$ is Asp, Gly, Leu, Phe, Ser, or Thr.

The invention also provides a non-naturally occurring, serum albumin binding moiety comprising a polypeptide comprising the amino acid sequence of:

Xaa$_1$-Xaa$_2$-Xaa$_3$-Cys-Xaa$_4$-Xaa$_5$-Xaa$_6$-Xaa$_7$-Cys-Xaa$_8$-Xaa$_9$-Xaa$_{10}$ (SEQ ID NO:2), wherein
Xaa$_1$ is Asn, His, Leu, Phe, Trp, or Val;
Xaa$_2$ is Ala, Glu, His, Lys, Trp, or Val;
Xaa$_3$ is Asp, Gly, Ile, His, Ser, Trp, or Val;
Xaa$_4$ is Asp, Asn, Ser, Thr, or Trp;
Xaa$_5$ is Asn, Gln, His, Ile, Leu, or Lys;
Xaa$_6$ is Ala, Asp, Phe, Trp, or Tyr;
Xaa$_7$ is Asp, Gly, Leu, Phe, Ser, or Thr;
Xaa$_8$ is Glu, Ile, Leu, Met, Ser, or Val;
Xaa$_9$ is Asn, Asp, Gln, Gly, Met, Ser, or Trp; and
Xaa$_{10}$ is Ala, Asn, Asp, Pro, Tyr, or Val.

In yet another embodiment, the invention provides a non-naturally occurring, serum albumin binding moiety comprising a polypeptide comprising the amino acid sequence of:

Ala-Glu-Gly-Thr-Gly-Ser-Xaa$_1$-Xaa$_2$-Xaa$_3$-Cys-Xaa$_4$-Xaa$_5$-Xaa$_6$-Xaa$_7$-Cys-Xaa$_8$-Xaa$_9$-Xaa$_{10}$-Ala-Pro-Glu (SEQ ID NO: 3), wherein
Xaa$_1$ is Asn, His, Leu, Phe, Trp, or Val;
Xaa$_2$ is Ala, Glu, His, Lys, Trp, or Val;
Xaa$_3$ is Asp, Gly, Ile, His, Ser, Trp, or Val;
Xaa$_4$ is Asp, Asn, Ser, Thr, or Trp;
Xaa$_5$ is Asn, Gln, His, Ile, Leu, or Lys;
Xaa$_6$ is Ala, Asp, Phe, Trp, or Tyr;
Xaa$_7$ is Asp, Gly, Leu, Phe, Ser, or Thr;
Xaa$_8$ is Glu, Ile, Leu, Met, Ser, or Val;
Xaa$_9$ is Asn, Asp, Gln, Gly, Met, Ser, or Trp; and
Xaa$_{10}$ is Ala, Asn, Asp, Pro, Tyr, or Val.

The invention also provides a non-naturally occurring, serum albumin binding moiety comprising a polypeptide comprising the amino acid sequence of:

Cys-Xaa$_1$-Xaa$_2$-Xaa$_3$-Xaa$_4$-Xaa$_5$-Xaa$_6$-Cys (SEQ ID NO: 130)

wherein
Xaa$_1$ is Ala, Leu, His, Met, Phe, Ser, or Thr;
Xaa$_2$ is Ile, Phe, Pro, Ser, Trp, or Tyr;
Xaa$_3$ is Asp, Gln, Glu, Lys, Pro, Trp, or Tyr;
Xaa$_4$ is Asp, Gln, Gly, Leu, Pro, or Trp;
Xaa$_5$ is Asp, Ile, Leu, Lys, Met, Pro, Trp, or Tyr; and
Xaa$_6$ is Glu, Gly, Ile, Phe, Thr, Trp, or Val.

The invention also provides a non-naturally occurring, serum albumin binding moiety comprising a polypeptide comprising the amino acid sequence of:

Xaa$_1$-Xaa$_2$-Xaa$_3$-Cys-Xaa$_4$-Xaa$_5$-Xaa$_6$-Xaa$_7$-Xaa$_8$-Xaa$_9$-Cys-Xaa$_{10}$-Xaa$_{11}$-Xaa$_{12}$ (SEQ ID NO: 131), wherein
Xaa$_1$ is Ala, Gln, Leu, Lys, Phe, Trp, or Tyr;
Xaa$_2$ is Asn, Gln, Glu, Ble, Thr, or Trp;
Xaa$_3$ is Asn, Gly, Phe, Thr, Trp, or Tyr;
Xaa$_4$ is Ala, Leu, His, Met, Phe, Ser, or Thr;
Xaa$_5$ is Ile, Phe, Pro, Ser, Trp, or Tyr;
Xaa$_6$ is Asp, Gln, Glu, Lys, Pro, Trp, or Tyr;
Xaa$_7$ is Asp, Gln, Gly, Leu, Pro, or Trp;
Xaa$_8$ is Asp, Ile, Leu, Lys, Met, Pro, Trp, or Tyr;
Xaa$_9$ is Gln, Gly, Ile, Phe, Thr, Trp, or Val;
Xaa$_{10}$ is Asp, Glu, Gly, Leu, Lys, Pro, or Ser;
Xaa$_{11}$ is Glu, His, Ile, Leu, Lys, Ser, Trp, or Val; and
Xaa$_{12}$ is Ala, Asn, His, Ile, Met, Phe, Pro, or Ser.

In yet another embodiment, the invention provides a non-naturally occurring, serum albumin binding moiety comprising a polypeptide comprising the amino acid sequence of:

Ala-Gly-Xaa$_1$-Xaa$_2$-Xaa$_3$-Cys-Xaa$_4$-Xaa$_5$-Xaa$_6$-Xaa$_7$-Xaa$_8$-Xaa$_9$-Cys-Xaa$_{10}$-Xaa$_{11}$-Xaa$_{12}$-Gly-Thr (SEQ ID NO: 132), wherein
Xaa$_1$ is Ala, Gln, Leu, Lys, Phe, Trp, or Tyr;
Xaa$_2$ is Asn, Gln, Glu, Ile, Thr, or Trp;
Xaa$_3$ is Asn, Gly, Phe, Thr, Trp, or Tyr;
Xaa$_4$ is Ala, Leu, His, Met, Phe, Ser, or Thr;
Xaa$_5$ is Ile, Phe, Pro, Ser, Trp, or Tyr;
Xaa$_6$ is Asp, Gln, Glu, Lys, Pro, Trp, or Tyr;
Xaa$_7$ is Asp, Gln, Gly, Leu, Pro, or Trp;
Xaa$_8$ is Asp, Ile, Leu, Lys, Met, Pro, Trp, or Tyr;
Xaa$_9$ is Gln, Gly, Ile, Phe, Thr, Trp, or Val;
Xaa$_{10}$ is Asp, Glu, Gly, Leu, Lys, Pro, or Ser;
Xaa$_{11}$ is Glu, His, Ile, Leu, Lys, Ser, Trp, or Val; and
Xaa$_{12}$ is Ala, Asn, His, Ile, Met, Phe, Pro, or Ser.

The invention also provides a non-naturally occurring serum albumin binding moiety comprising a polypeptide comprising the amino acid sequence:

Cys-Xaa$_1$-Xaa$_2$-Xaa$_3$-Xaa$_4$-Xaa$_5$-Xaa$_6$-Xaa$_7$-Xaa$_8$-Cys (SEQ ID NO: 133), wherein
Xaa$_1$ is Gln, Glu, Phe, or Met;
Xaa$_2$ is Asp, Pro, or Thr;
Xaa$_3$ is Ile, Ser, or Trp;
Xaa$_4$ is His, Met, Phe or Pro;
Xaa$_5$ is Asn, Leu, or Thr;
Xaa$_6$ is Arg, Asn, His, or Thr;
Xaa$_7$ is Arg, Met, Phe, or Tyr; and
Xaa$_8$ is Asp, Gly, Phe, or Trp.

In another embodiment, the invention provides a non-naturally occurring, serum albumin binding moiety comprising a polypeptide comprising the amino acid sequence of:

Xaa$_1$-Xaa$_2$-Xaa$_3$-Cys-Xaa$_4$-Xaa$_5$-Xaa$_6$-Xaa$_7$-Xaa$_8$-Xaa$_9$-Xaa$_{10}$-Xaa$_{11}$-Cys-Xaa$_{12}$-Xaa$_{13}$-Xaa$_{14}$ (SEQ ID NO: 134), wherein
Xaa$_1$ is Arg, Phe, or Tyr;
Xaa$_2$ is Arg, Leu, Ser, or Trp;
Xaa$_3$ is Asn, Asp, Phe, or Tyr;
Xaa$_4$ is Gln, Glu, Phe, or Met;
Xaa$_5$ is Asp, Pro, or Thr;
Xaa$_6$ is Ile, Ser, or Trp;
Xaa$_7$ is His, Met, Phe or Pro;
Xaa$_8$ is Asn, Leu, or Thr;
Xaa$_9$ is Arg, Asn, His, or Thr;
Xaa$_{10}$ is Arg, Met, Phe, or Tyr;
Xaa$_{11}$ is Asp, Gly, Phe, or Trp;
Xaa$_{12}$ is Ala, Asn, or Asp;
Xaa$_{13}$ is Arg, Phe, Pro, or Tyr; and
Xaa$_{14}$ is Arg, His, Phe, or Ser.

In still another embodiment, the invention provides a non-naturally occurring, serum albumin binding moiety comprising a polypeptide comprising the amino acid sequence of:

Gly-Ser-Xaa$_1$-Xaa$_2$-Xaa$_3$-Cys-Xaa$_4$-Xaa$_5$-Xaa$_6$-Xaa$_7$-Xaa$_8$-Xaa$_9$-Xaa$_{10}$-Xaa$_{11}$-Cys-Xaa$_{12}$-Xaa$_{13}$-Xaa$_{14}$-Ala-Pro (SEQ ID NO: 135), wherein
Xaa$_1$ is Arg, Phe, or Tyr;
Xaa$_2$ is Arg, Leu, Ser, or Trp;

Xaa$_3$ is Asn, Asp, Phe, or Tyr;
Xaa$_4$ is Gln, Glu, Phe, or Met;
Xaa$_5$ is Asp, Pro, or Thr;
Xaa$_6$ is Ile, Ser, or Trp;
Xaa$_7$ is His, Met, Phe or Pro;
Xaa$_8$ is Asn, Leu, or Thr;
Xaa$_9$ is Arg, Asn, His, or Thr;
Xaa$_{10}$ is Arg, Met, Phe, or Tyr;
Xaa$_{11}$ is Asp, Gly, Phe, or Trp;
Xaa$_{12}$ is Ala, Asn, or Asp;
Xaa$_{13}$ is Arg, Phe, Pro, or Tyr; and
Xaa$_{14}$ is Arg, His, Phe, or Ser.

The invention also provides a non-naturally occurring serum albumin binding moiety comprising a polypeptide comprising the amino acid sequence:

Cys-Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Cys (SEQ ID NO: 4), wherein
Xaa$_1$ is Ala, Asn, Asp, Gln, Glu, Gly, Ile, Leu, Lys, Phe, Pro, Ser, Thr, Trp, Tyr, or Val;
Xaa$_2$ is Ala, Arg, Asp, Glu, Gly, His, Ile, Leu, Lys, Met, Phe, Ser, Thr, Trp, Tyr, or Val;
Xaa$_3$ is Ala, Arg, Asp, Gln, Glu, Gly, Ile, Leu, Lys, Met, Pro, Ser, Thr, Trp, Tyr, or Val;
Xaa$_4$ is Ala, Arg, Asn, Asp, Ile, Leu, Phe, Pro, Ser, Trp, or Tyr;
Xaa$_5$ is Ala, Asp, Glu, Gly, Ile, Met, Phe, Pro, Thr, Trp, or Tyr;
Xaa$_6$ is Ala, Arg, Asn, Asp, Gln, Glu, His, Ile, Leu, Lys, Phe, Ser, Thr, Trp, or Tyr;
Xaa$_7$ is Ala, Arg, Asp, Glu, Gly, His, Met, Phe, Pro, Ser, Thr, or Trp;
Xaa$_8$ is Ala, Arg, Asp, Gln, Glu, His, Ile, Leu, Met, Phe, Pro, Ser, Thr, Trp, or Val;
Xaa$_9$ is Ala, Arg, Asp, Gln, Glu, His, Ile, Leu, Lys, Met, Phe, Pro, Ser, Thr, Trp, Tyr, or Val;
Xaa$_{10}$ is Ala, Asp, Gln, Glu, Gly, His, Ile, Leu, Lys, Phe, Pro, Ser, Thr, Trp, Tyr, or Val.

In another embodiment, the invention provides a non-naturally occurring, serum albumin binding moiety comprising a polypeptide comprising the amino acid sequence of:

Xaa$_1$-Xaa$_2$-Xaa$_3$-Cys-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Cys-Xaa$_{14}$-Xaa$_{15}$-Xaa$_{16}$ (SEQ ID NO: 5), wherein
Xaa$_1$ is Ala, Arg, Asp, Asn, Gly, His, Leu, Phe, Pro, Ser, Trp, Tyr;
Xaa$_2$ is Ala, Arg, Asp, Asn, Gly, His, Phe, Pro, Ser, or Trp;
Xaa$_3$ is Ala, Asn, Asp, Glu, Glu, Gly, His, Leu, Met, Phe, Ser, Thr, Trp, Tyr, or Val;
Xaa$_4$ is Ala, Asn, Asp, Gln, Glu, Gly, Ile, Leu, Lys, Phe, Pro, Ser, Thr, Trp, Tyr, or Val;
Xaa$_5$ is Ala, Arg, Asp, Glu, Gly, His, Ile, Leu, Lys, Met, Phe, Ser, Thr, Trp, Tyr, or Val;
Xaa$_6$ is Ala, Arg, Asp, Gln, Glu, Gly, Ile, Leu, Lys, Met, Pro, Ser, Thr, Trp, Tyr, or Val;
Xaa$_7$ is Ala, Arg, Asn, Asp, Ile, Leu, Phe, Pro, Ser, Trp, or Tyr;
Xaa$_8$ is Ala, Asp, Glu, Gly, Ile, Met, Phe, Pro, Thr, Trp, or Tyr;
Xaa$_9$ is Ala, Arg, Asn, Asp, Gln, Glu, His, Ile, Leu, Lys, Phe, Ser, Thr, Trp, or Tyr;
Xaa$_{10}$ is Ala, Arg, Asp, Glu, Gly, His, Met, Phe, Pro, Ser, Thr, or Trp;

Xaa$_{11}$ is Ala, Arg, Asp, Gln, Glu, His, Ile, Leu, Met, Phe, Pro, Ser, Thr, Trp, or Val;
Xaa$_{12}$ is Ala, Arg, Asp, Glu, Glu, His, Ile, Leu, Lys, Met, Phe, Pro, Ser, Thr, Trp, Tyr, or Val;
Xaa$_{13}$ is Ala, Asp, Glu, Glu, Gly, His, Ile, Leu, Lys, Phe, Pro, Ser, Thr, Trp, Tyr, or Val;
Xaa$_{14}$ is Ala, Arg, Asn, Asp, Glu, Gly, His, Ile, Leu, Lys, Met, Pro, Ser, Thr, Trp, or Tyr;
Xaa$_{15}$ is Ala, Arg, Asn, Asp, Gly, His, Leu, Phe, Pro, Ser, Trp, or Tyr; and
Xaa$_{16}$ is Ala, Asn, Asp, Gly, His, Leu, Phe, Pro, Ser, Trp, or Tyr.

Particularly preferred embodiments having the structure of SEQ ID NO: 5, above, include polypeptides comprising the amino acid sequence (A) or (B):

(A) Xaa$_1$-Arg-Xaa$_2$-Cys-Xaa$_3$-Thr-Xaa$_4$-Xaa$_5$-Pro-Xaa$_6$-Xaa$_7$-Xaa$_8$-Xaa$_9$-Xaa$_{10}$-Cys-Xaa$_{11}$-Xaa$_{12}$-Xaa$_{13}$ (SEQ ID NO: 270), wherein
Xaa$_1$ is Asn, Leu, or Phe, preferably Leu;
Xaa$_2$ is Ala, Asn, Asp, Gln, Glu, Gly, His, Leu, Met, Phe, Ser, Thr, Trp, Tyr, or Val;
Xaa$_3$ is Ala, Asn, Asp, Gln, Glu, Gly, Ile, Leu, Lys, Phe, Pro, Ser, Thr, Trp, Tyr, or Val;
Xaa$_4$ is Ala, Arg, Asp, Gln, Glu, Gly, Ile, Leu, Lys, Met, Pro, Ser, Thr, Trp, Tyr, or Val;
Xaa$_5$ is Phe, Trp, or Tyr, preferably Trp;
Xaa$_6$ is His or Phe, preferably Phe;
Xaa$_7$ is Asp, Glu, or Thr;
Xaa$_8$ is Ala, Arg, Asp, Gln, Glu, His, Ile, Leu, Met, Phe, Pro, Ser, Thr, Trp, or Val;
Xaa$_9$ is Ala, Arg, Asp, Gln, Glu, His, Ile, Leu, Lys, Met, Phe, Pro, Ser, Thr, Trp, Tyr, or Val;
Xaa$_{10}$ is Ala, Asp, Gln, Glu, Gly, His, Ile, Leu, Lys, Phe, Pro, Ser, Thr, Trp, Tyr, or Val;
Xaa$_{11}$ is Pro or Ser;
Xaa$_{12}$ is Asn or Pro; and
Xaa$_{13}$ is Asn or Pro; or (B) Xaa$_1$-Xaa$_2$-Xaa$_3$-Cys-Ile-Thr-Xaa$_4$-Pro-Phe-Xaa$_5$-Xaa$_6$-Xaa$_7$-Xaa$_8$-Xaa$_9$-Cys-Xaa$_{10}$-Asn-Xaa$_{11}$ (SEQ ID NO: 271), wherein
Xaa$_1$ is Ala, Arg, Asp, Asn, Gly, His, Leu, Phe, Pro, Ser, Trp, Tyr;
Xaa$_2$ is Ala, Arg, Asp, Asn, Gly, His, Phe, Pro, Ser, or Trp;
Xaa$_3$ is Glu, Leu, or Met, preferably Met;
Xaa$_4$ is Trp or Tyr, preferably Trp;
Xaa$_5$ is Gln, Glu, or Lys;
Xaa$_6$ is Ala, Arg, Asp, Glu, Gly, His, Met, Phe, Pro, Ser, Thr, or Trp;
Xaa$_7$ is Met, Pro, or Ser, preferably Pro;
Xaa$_8$ is Ala, Arg, Asp, Gln, Glu, His, Ile, Leu, Lys, Met, Phe, Pro, Ser, Thr, Trp, Tyr, or Val;
Xaa$_9$ is His or Pro, preferably Pro;
Xaa$_{10}$ is Ala, Arg, Asn, Asp, Glu, Gly, His, Ile, Leu, Lys, Met, Pro, Ser, Thr, Trp, or Tyr; and
Xaa$_{11}$ is Ala, Asn, Asp, Gly, His, Leu, Phe, Pro, Ser, Trp, or Tyr.

In still another embodiment, the invention provides a non-naturally occurring, serum albumin binding moiety comprising a polypeptide comprising the amino acid sequence of:

Ala-Glu-Gly-Thr-Gly-Xaa$_0$-Xaa$_1$-Xaa$_2$-Xaa$_3$-Cys-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Cys-Xaa$_{14}$-Xaa$_{15}$-Xaa$_{16}$-Xaa$_{17}$-Pro-Glu (SEQ ID NO: 6), wherein
Xaa$_0$ is Ala or Asp;
Xaa$_1$ is Ala, Arg, Asp, Asn, Gly, His, Leu, Phe, Pro, Ser, Trp, Tyr;
Xaa$_2$ is Ala, Arg, Asp, Asn, Gly, His, Phe, Pro, Ser, or Trp;
Xaa$_3$ is Ala, Asn, Asp, Gln, Glu, Gly, His, Leu, Met, Phe, Ser, Thr, Trp, Tyr, or Val;
Xaa$_4$ is Ala, Asn, Asp, Gln, Glu, Gly, Ile, Leu, Lys, Phe, Pro, Ser, Thr, Trp, Tyr, or Val;
Xaa$_5$ is Ala, Arg, Asp, Glu, Gly, His, Ile, Leu, Lys, Met, Phe, Ser, Thr, Trp, Tyr, or Val;
Xaa$_6$ is Ala, Arg, Asp, Gln, Glu, Gly, Ile, Leu, Lys, Met, Pro, Ser, Thr, Trp, Tyr, or Val;
Xaa$_7$ is Ala, Arg, Asn, Asp, Ile, Leu, Phe, Pro, Ser, Trp, or Tyr;
Xaa$_8$ is Ala, Asp, Glu, Gly, Ile, Met, Phe, Pro, Thr, Trp, or Tyr;
Xaa$_9$ is Ala, Arg, Asn, Asp, Gln, Glu, His, Ile, Leu, Lys, Phe, Ser, Thr, Trp, or Tyr;
Xaa$_{10}$ is Ala, Arg, Asp, Glu, Gly, His, Met, Phe, Pro, Ser, Thr, or Trp;
Xaa$_{11}$ is Ala, Arg, Asp, Gln, Glu, His, Ile, Leu, Met, Phe, Pro, Ser, Thr, Trp, or Val;
Xaa$_{12}$ is Ala, Arg, Asp, Gln, Glu, His, Ile, Leu, Lys, Met, Phe, Pro, Ser, Thr, Trp, Tyr, or Val;
Xaa$_{13}$ is Ala, Asp, Gln, Glu, Gly, His, Ile, Leu, Lys, Phe, Pro, Ser, Thr, Trp, Tyr, or Val;
Xaa$_{14}$ is Ala, Arg, Asn, Asp, Gln, Gly, His, Ile, Leu, Lys, Met, Pro, Ser, Thr, Trp, or Tyr;
Xaa$_{15}$ is Ala, Arg, Asn, Asp, Gly, His, Leu, Phe, Pro, Ser, Trp, or Tyr;
Xaa$_{16}$ is Ala, Asn, Asp, Gly, His, Leu, Phe, Pro, Ser, Trp, or Tyr; and
Xaa$_{17}$ is Ala or Asp.

In a further embodiment, the invention provides a non-naturally occurring, serum albumin binding moiety comprising a linear polypeptide comprising an amino acid sequence selected from the group consisting of:
P T V V Q P K F H A F T H E D L L W I F (SEQ ID NO: 136),
L K S Q M V H A L P A A S L H D Q H E L (SEQ ID NO: 137), and
S Q V Q G T P D L Q F T V R D F I Y M F (SEQ ID NO: 138).

Preferred serum albumin binding moieties of the invention comprise non-naturally occurring polypeptides comprising the following amino acid sequences (depicted using the standard single letter abbreviations for the twenty common α-amino acids):
C T I F L C (SEQ ID NO: 7),
C E G K D M I D W V Y C (SEQ ID NO: 8),
C D R I A W Y P Q H L C (SEQ ID NO: 9),
C D R I A W Y P Q H A C (SEQ ID NO: 72),
C D R I A W Y P Q A L C (SEQ ID NO: 73),
C D R I A W Y P A H L C (SEQ ID NO: 74),
C D R I A W Y A Q H L C (SEQ ID NO: 75),
C D R I A W A P Q H L C (SEQ ID NO: 76),
C D R I A A Y P Q H L C (SEQ ID NO: 77),
C D R A A W Y P Q H L C (SEQ ID NO: 78),
C D A I A W Y P Q H L C (SEQ ID NO: 79),
C A R I A W Y P Q H L C (SEQ ID NO: 80),
C E P W M L R F G C (SEQ ID NO: 10),
C D Q W F C (SEQ ID NO: 11),
C N N A L C (SEQ ID NO: 12),
C D H F F C (SEQ ID NO: 13),
C W H F S C (SEQ ID NO: 14),
C V T R W A N R D Q Q C (SEQ ID NO: 15),
C V T D W A N R H Q H C (SEQ ID NO: 16),
C V K D W A N R R R G C (SEQ ID NO: 17),
C K F S W I R S P A F C (SEQ ID NO: 18),
C Q T T W P F T M M Q C (SEQ ID NO: 139),
C V T M W P F E Q I F C (SEQ ID NO: 140),
C F T Y Y P F T T F S C (SEQ ID NO: 141),
C W T K F P F D L V W C (SEQ ID NO: 142),
C V S Y W P H F V P V C (SEQ ID NO: 143),
C Y I S F P F D Q M Y C (SEQ ID NO: 144),
C S V Q Y P F E V V V C (SEQ ID NO: 145),
C W T Q Y P F D H S T C (SEQ ID NO: 146),
C I T W P F K R P W P C (SEQ ID NO: 147),
C I S W P F E M P F H C (SEQ ID NO: 148),
C I T W P F K R P W P C (SEQ ID NO: 149),
C I T Y P F H E M F P C (SEQ ID NO: 150),
C I T W P F Q T S Y P C (SEQ ID NO: 151),
C K F S W I R S P A F C (SEQ ID NO: 152),
C W I V D E D G T K W C (SEQ ID NO: 153),
C D S A Y W Q E I P A C (SEQ ID NO: 154),
C L W D P M L C (SEQ ID NO: 155),
C E H P Y W T E V D K C (SEQ ID NO: 156),
C D T P Y W R D L W Q C (SEQ ID NO: 157),
C Q L P Y M S T P E F C (SEQ ID NO: 158),
C G R G F D K E S I Y C (SEQ ID NO: 159),
C V T Y I G T W E T V C (SEQ ID NO: 160),
C T D T N W S W M F D C (SEQ ID NO: 161),
C T L E I G T W F V F C (SEQ ID NO: 162),
C K I A L F Q H F E V C (SEQ ID NO: 163),
C I K L Y G L G H M Y C (SEQ ID NO: 164),
C E M Q S I I P W W E C (SEQ ID NO: 165),
C V E K Y Y W D V L I C (SEQ ID NO: 166),
C P G R Y S M F P C (SEQ ID NO: 167),
C N V R W T D T P Y W C (SEQ ID NO: 168),
C T Y D P I A D L L F C (SEQ ID NO: 169),
C M D W P N H R D C (SEQ ID NO: 170),
C F P I H L T M F C (SEQ ID NO: 171),
C Q T S F T N Y W C (SEQ ID NO: 172),
C M E F G P D D C (SEQ ID NO: 173),
C S W D P I F C (SEQ ID NO: 174),
C A W D P L V C (SEQ ID NO: 175),
C H I Y D W F C (SEQ ID NO: 176),
C L W D P M I C (SEQ ID NO: 177),
C S P P G K T C (SEQ ID NO: 178),
C T F W Q Y W C (SEQ ID NO: 179),
C M F E L P F C (SEQ ID NO: 180),
C F S K P D Q C (SEQ ID NO: 181),
C F Y Q W W G C (SEQ ID NO: 182),
C T W D P I F C (SEQ ID NO: 183),
C C W L Y D C (SEQ ID NO: 184),
C D K Y G C (SEQ ID NO: 185), and
C S K D T C (SEQ ID NO: 186).

Additional preferred embodiments of the present invention are serum albumin binding polypeptides comprising an amino acid sequence selected from the group consisting of:
A D F C E G K D M I D W V Y C R L Y (SEQ ID NO: 58),
F W F C D R I A W Y P Q H L C E F L (SEQ ID NO: 59),
F W F C D R I A W Y P Q H L C E F A (SEQ ID NO: 81),
F W F C D R I A W Y P Q H L C E A L (SEQ ID NO: 82),
F W F C D R I A W Y P Q H L C A F L (SEQ ID NO: 83),
F W F C D R I A W Y P Q H A C E F L (SEQ ID NO: 84), F W F C D R I A W Y P Q A L C E F L (SEQ ID NO: 85),
F W F C D R I A W Y P A H L C E F L (SEQ ID NO: 86),
F W F C D R I A W Y A Q H L C E F L (SEQ ID NO: 87),
F W F C D R I A W A P Q H L C E F L (SEQ ID NO: 88),
F W F C D R I A A Y P Q H L C E F L (SEQ ID NO: 89),
F W F C D R A A W Y P Q H L C E F L (SEQ ID NO: 90),
F W F C D A I A W Y P Q H L C E F L (SEQ ID NO: 91),
F W F C A R I A W Y P Q H L C E F L (SEQ ID NO: 92),
F W A C D R I A W Y P Q H L C E F L (SEQ ID NO: 93),
F A F C D R I A W Y P Q H L C E F L (SEQ ID NO: 94),
A W F C D R I A W Y P Q H L C E F L (SEQ ID NO: 95),
D W D C V T R W A N R D Q Q C W G P (SEQ ID NO: 60),
D W D C V T R W A N R D Q Q C W A L (SEQ ID NO: 61),
D W D C V T D W A N R H Q H C W A L (SEQ ID NO: 62),
D W Q C V K D W A N R R R G C M A D (SEQ ID NO: 63),
R N M C K F S W I R S P A F C A R A (SEQ ID NO: 64),
L R D C Q T T W P F M M Q C P N N (SEQ ID NO: 187),
N R E C V T M W P F E Q I F C P W P (SEQ ID NO: 188),
L R S C F T Y Y P F T T F S C S P A (SEQ ID NO: 189),
L S H C W T K F P F D L V W C D S P (SEQ ID NO: 190),
L R M C V S Y W P H F V P V C E N P (SEQ ID NO: 191),
L R D C Y I S F P F D Q M Y C S H F (SEQ ID NO: 192),
F R H C S V Q Y P F E V V V C P A N (SEQ ID NO: 193),
L R N C W T Q Y P F D H S T C S P N (SEQ ID NO: 194),
D S M C I T W P F K R P W P C A N (SEQ ID NO: 195),
A F M C I S W P F E M P F H C S P D (SEQ ID NO: 196),
D S M C I T W P F K R P W P C A N P (SEQ ID NO: 197)
W D L C I T Y P F H E M F P C E D G (SEQ ID NO: 198),
G G E C I T W P F Q T S Y P C T N G (SEQ ID NO: 199),
R N M C K F S W I R S P A F C A R A (SEQ ID NO: 200),
F S L C W I V D E D G T K W C L P (SEQ ID NO: 201),
R W F C D S A Y W Q E I P A C A R D (SEQ ID NO: 202),
R W Y C L W D P M L C M S D (SEQ ID NO: 203),
A W Y C E H P Y W T E V D K C H S S (SEQ ID NO: 204),
S D F C D T P Y W R D L W Q C N S P (SEQ ID NO: 205),
L P W C Q L P Y M S T P E F C I R P (SEQ ID NO: 206),
Y H V C G R G F D K E S I Y C K F L (SEQ ID NO: 207),
S F C V T Y I G T W E T V C K R S (SEQ ID NO: 208),
N D G C T D T N W S W M F D C P P L (SEQ ID NO: 209),
W R D C T L E I G T W F V F C K G S (SEQ ID NO: 210),
S P Y C K I A L F Q H F E V C A A D (SEQ ID NO: 211),
R H W C I K L Y G L G H M Y C N R S (SEQ ID NO: 212),
D H A C E M Q S I I P W W E C Y P H (SEQ ID NO: 213),
P R S C V E K Y Y W D V L I C G F F (SEQ ID NO: 214),
F H T C P H G R Y S M F P C D Y W (SEQ ID NO: 215),
I H G W C N V R W T D T P Y W C A F S (SEQ ID NO: 216),
Y R V C T Y D P I A D L L F C P F N (SEQ ID NO: 217),
R S F C M D W P N H R D C D Y S (SEQ ID NO: 218),
F W D C F P I H L T M F C D R F (SEQ ID NO: 219),
Y L Y C Q T S F T N Y W C A F H H (SEQ ID NO: 220),
G L Y C M E F G P D D C A W H (SEQ ID NO: 221),
K N F C S W D P I F C G I H (SEQ ID NO: 222),
K W Y C A W D P L V C E I F (SEQ ID NO: 223),
W T T C H I Y D W F C S S S (SEQ ID NO: 224),
Q W Y C L W D P M I C G L I (SEQ ID NO: 225),
Q T N C S P P G K T C D K N (SEQ ID NO: 226),
A I C T F W Q Y W C L E P (SEQ ID NO: 227),
F E W C M F E L P F C S W P (SEQ ID NO: 228),
Q E G C F S K P D Q C K V M (SEQ ID NO: 229),
L E Y C F Y Q W W G C P H A (SEQ ID NO: 230),
Y Q F C T W D P I F C G W H (SEQ ID NO: 231),
L W D C W L Y D C E G N (SEQ ID NO: 232),
V H S C D K Y G C V N A (SEQ ID NO: 233),
F E H C S K D T C S G N (SEQ ID NO: 234),
V A W C T I F L C L D V (SEQ ID NO: 239),
F K I C D Q W F C L M P (SEQ ID NO: 240),
H V G C N N A L C M Q Y (SEQ ID NO: 241),
W K V C D H F F C L S P (SEQ ID NO: 242 ),
N H G C W H F S C I W D (SEQ ID NO: 243),
F R N C E P W M L R F G C N P R (SEQ ID NO: 244),
A D F C E G K D M I D W V Y C R L Y (SEQ ID NO: 245),
F F W F C D R I A W Y P Q H L C E F L D (SEQ ID NO: 246),
D W D C V T R W A N R D Q Q C W G P (SEQ ID NO: 247),
D W D C V T R W A N R D Q Q C W A L (SEQ ID NO: 248),
W D W D C V T D W A N R H Q H C W A L (SEQ ID NO: 249),
D W Q C V K D W A N R R R G C M A D (SEQ ID NO: 250),
R R N M C K F S W I R S P A F C A R A D P (SEQ ID NO: 251).

Particularly preferred embodiments are serum albumin binding polypeptides comprising an amino acid sequence selected from the group consisting of:
A E G T G D A D F C E G K D M I D W V Y C R L Y D P E (SEQ ID NO: 65),
A E G T G D F W F C D R I A W Y P Q H L C E F L D P E (SEQ ID NO: 66),
A E G T G D F W F C D R I A W Y P Q H L C E F L A P E (SEQ ID NO: 96),
A E G T G D F W F C D R I A W Y P Q H L C E F A D P E (SEQ ID NO: 97),
A E G T G D F W F C D R I A W Y P Q H L C E A L D P E (SEQ ID NO: 98),
A E G T G D F W F C D R I A W Y P Q H L C A F L D P E (SEQ ID NO: 99),
A E G T G D F W F C D R I A W Y P Q H A C E F L D P E (SEQ ID NO: 100), A E G T D F W F C D R I A W Y P Q A L C E F L D P E (SEQ ID NO: 101),
A E G T D F W F C D R I A W Y P A H L C E F L D P E (SEQ ID NO: 102),
A E G T D F W F C D R I A W Y A Q H L C E F L D P E (SEQ ID NO: 103),
A E G T D F W F C D R I A W A P Q H L C E F L D P E (SEQ ID NO: 104),
A E G T D F W F C D R I A A Y P Q H L C E F L D P E (SEQ ID NO: 105),
A E G T D F W F C D R A A W Y P Q H L C E F L D P E (SEQ ID )NO: 106),
A E G T D F W F C D A I A W Y P Q H L C E F L D P E (SEQ ID NO: 107),
A E G T D F W F C A R I A W Y P Q H L C E F L D P E (SEQ ID NO: 108),
A E G T D F W A C D R I A W Y P Q H L C E F L D P E (SEQ ID NO: 109),
A E G T D F A F C D R I A W Y P Q H L C E F L D P E (SEQ ID NO: 110),
A E G T D A W F C D R I A W Y P Q H L C E F L D P E (SEQ ID NO: 111),
A E G T G A F W F C D R I A W Y P Q H L C E F L D P E (SEQ ID NO: 112),
A E G T G D D W D C V T R W A N R D Q Q C W G P D P E (SEQ ID NO: 67),
A E G T G D D W D C V T R W A N R D Q Q C W A L D P E (SEQ ID NO: 68),
A E G T G D D W D C V T D W A N R H Q H C W A L D P E (SEQ ID NO: 69),
A E G T G D D W Q C V K D W A N R R R G C M A D D P E (SEQ ID NO: 70), and
A E G T G D R N M C K F S W I R S P A F C A R A D P E (SEQ ID NO: 71).

A particularly preferred embodiment is a serum albumin binding peptide that has the formula:
A c-A E G T G D F W F C D R I A W Y P Q H L C E F L D P E G G G K-NH$_2$ (SEQ ID NO: 19), which peptide is designated DX-236, wherein Ac indicates an N-terminal acetyl capping group and —NH$_2$ indicates a C-terminal amide capping group. DX-236 binds mammalian serum albumins and is useful under appropriate conditions as a "pan mammalian" serum albumin binding moiety. Additional preferred embodiments include the following:
Ac-A E G T G D F W F C D R I A W Y P Q H L C E F L A P E G G G K-NH$_2$,
Ac-A E G T G D F W F C D R I A W Y P Q H L C E F A D P E G G G K-NH$_2$,
Ac-A E G T G D F W F C D R I A W Y P Q H L C E A L D P E G G G K-NH$_2$,
Ac-A E G T G D F W F C D R I A W Y P Q H L C A F L D P E G G G K-NH$_2$,
Ac-A E G T G D F W F C D R I A W Y P Q H A C E F L D P E G G G K-NH$_2$,
Ac-A E G T G D F W F C D R I A W Y P Q A L C E F L D P E G G G K-NH$_2$,
Ac-A E G T G D F W F C D R I A W Y P A H L C E F L D P E G G G K-NH$_2$,
Ac-A E G T G D F W F C D R I A W Y A Q H L C E F L D P E G G G K-NH$_2$,
Ac-A E G T G D F W F C D R I A W A P Q H L C E F L D P E G G G K-NH$_2$,
Ac-A E G T G D F W F C D R I A A Y P Q H L C E F L D P E G G G K-NH$_2$,
Ac-A E G T G D F W F C D R A A W Y P Q H L C E F L D P E G G G K-NH$_2$,
Ac-A E G T G D F W F C D A I A W Y P Q H L C E F L D P E G G G K-NH$_2$,
Ac-A E G T G D F W F C A R I A W Y P Q H L C E F L D P E G G G K-NH$_2$,
Ac-A E G T G D F W A C D R I A W Y P Q H L C E F L D P E G G G K-NH$_2$,
Ac-A E G T G D F A F C D R I A W Y P Q H L C E F L D P E G G G K-NH$_2$,
Ac-A E G T G D A W F C D R I A W Y P Q H L C E F L D P E G G G K-NH$_2$, and
Ac-A E G T G A F W F C D R I A W Y P Q H L C E F L D P E G G G K-NH$_2$,
(SEQ ID NOs: 113 through 129, respectively).

Additional embodiments preferred embodiments include the following:
Ac-G D L R D C Q T T W P F T M M Q C P N N D P G G G K-NH$_2$,
Ac-G D N R E C V T M W P F E Q I F C P W P D P G G G K-NH$_2$,
Ac-G D L R S C F T Y Y P F T T F S C S P A D P G G G K-NH$_2$,
Ac-G D D S M C I T W P F K R P W P C A N D P G G G K-NH$_2$,
Ac-G D R N M C K F S W I R S P A F C A R A D P G G G K-NH$_2$,
Ac-G D F S L C W I V D E D G T K W C L P D P G G G K-NH$_2$,
Ac-G D R W F C D S A Y W Q E I P A C A R D D P G G G K-NH$_2$,
Ac-G D S D F C D T P Y W R D L W Q C N S P D P G G G K-NH$_2$,
Ac-G D S F C V T Y I G T W E T V C K R S D P G G G K-NH$_2$,
Ac-G D N D G C T D T N W S W M F D C P P L D P G G G K-NH$_2$,
Ac-G D S P Y C K I A L F Q H F E V C A A D D P G G G K-NH$_2$,
Ac-G D P R S C V E K Y Y W D V L I C G F F D P G G G K-NH$_2$,
Ac-G S R S F C M D W P N H R D C D Y S A P G G G K-NH$_2$,
Ac-A G K W Y C A W D P L V C E I F G T G G G K-NH$_2$,
Ac-A G W T T C H I Y D W F C S S S G T G G G K-NH$_2$,
Ac-A G L E Y C F Y Q W W G C P H A G T G G G K-NH$_2$,
Ac-A G Y Q F C T W D P I F C G W H G T G G G K-NH$_2$, and
Ac-G S L W D C W L Y D C E G N A P G G G K-NH$_2$, (SEQ ID NOs: 252 through 269, respectively).

Another particularly preferred embodiment of the invention is a serum albumin binding moiety that has the formula:
Ac-A E G T G D R N M C K F S W I R S P A F C A R A D P E-X—K—NH$_2$ (SEQ ID NO: 20), which binding moiety is designated peptide compound DX-321, wherein Ac indicates an N-terminal acetyl capping group, X indicates a peptide linked 6-aminohexanoic acid group, and —NH$_2$ indicates a C-terminal amide capping group. DX-321 preferentially binds human serum albumin (HSA) over other species of serum albumin under appropriate conditions. DX-321 is useful as a reagent to specifically detect or isolate HSA or to specifically link another molecule to HSA.

Serum albumin binding moieties of the invention may comprise a serum albumin binding polypeptide described herein, a phage or other replicable genetic package displaying a serum albumin binding polypeptide described herein, and molecules that comprise a serum albumin binding polypeptide described herein further linked (covalently or non-covalently) to other molecules (such as other polypeptides, detectable molecular tags, radionuclides, etc.).

The invention also provides methods of using a serum albumin binding moiety to detect or isolate a serum albumin in a solution. For such methods, a serum albumin binding moiety of the invention may be used in a variety of formats, including but not limited to, immobilized on a solid surface, such as adsorbed on the surface of a well of a multi-well assay plate, immobilized by conjugation to the surface of chromatography matrix material, such as conjugated to N-hydroxysuccinimide (NHS)-SEPHAROSE® chromatography particles, or suspended or dispersed as a free, unconjugated moiety in a solution, e.g., of whole blood or a fraction thereof, which contains a serum albumin of interest.

In a preferred embodiment, the invention provides a method of isolating a serum albumin from a solution comprising the steps of providing a serum albumin binding moiety of the invention immobilized on a solid surface; contacting the immobilized binding moiety with the solution containing a serum albumin to permit the serum albumin in the solution to form a binding complex with the immobilized binding moiety; separating the unbound portion of the solution from the immobilized binding moiety; and, optionally, eluting or separating the serum albumin from the immobilized binding moiety. Preferably, the immobilized binding moiety binds serum albumin in the presence of a buffer having a relatively mild acidic pH, such as 3 mM phosphate buffer, pH 6.2. According to the invention, the bound serum albumin may then be released from the immobilized binding moiety in a purified form by contacting or washing the immobilized peptide binding moiety with a buffer having a stronger acidic pH, such as pH 2, or a basic pH, such as pH 9.

The serum albumin binding moieties of the invention may also be used to label or identify a serum albumin molecule in a solution. In a preferred embodiment, serum albumin is detected in a solution comprising the steps of providing a serum albumin binding moiety, which is linked to a detectable label or tag molecule; allowing the binding moiety to form a complex with a serum albumin molecule in the solution; and detecting the presence of the label or tag linked. Preferably, such detection assays are sensitive enough for quantitative determination of serum albumin in a sample, i.e., where the intensity of the tag or label detected is directly proportional to the amount of serum albumin bound in the solution.

In another method of the invention, serum albumin binding moieties are used in blood pool imaging of an individual, such as used in diagnosing blocked blood vessels, hemorrhage of damaged blood vessels, and internal bleeding. In a preferred embodiment, the method comprises administering to an individual, a serum albumin binding moiety linked to a detectable label. In a more preferred embodiment, the label is detectable by magnetic resonance imaging (MRI) and the label is a technetium ($Tc^{99}$)-containing label.

In yet another embodiment, the invention provides methods for increasing the serum half-life of a therapeutic or diagnostic compound of interest comprising linking the therapeutic or diagnostic compound to a serum albumin binding moiety of the invention and administering the compound/serum albumin binding moiety to an individual. The compound/binding moiety conjugate in the blood will associate with circulating serum albumin molecule(s) and will remain in the serum longer than if the compound were administered in the absence of a serum albumin binding moiety. The albumin binding moiety can be selected for its particular affinity for serum albumin, so as to tailor the behavior of the conjugate in circulation to the particular therapeutic or diagnostic need for which the conjugate is employed.

In yet another embodiment, the invention provides a method of isolating serum albumin fusion proteins, in which a serum albumin has been fused in frame to another polypeptide, comprising the steps of contacting a solution containing a serum albumin fusion protein with a serum albumin binding moiety described herein to form a complex between the serum albumin fusion protein and the serum albumin binding moiety; separating unbound components of the solution from the complex; and, optionally, eluting or separating the serum albumin fusion protein from the binding moiety. In a particularly preferred embodiment, the serum albumin fusion protein comprises HSA fused to another polypeptide, and the serum albumin binding moiety comprises compound DX-236 (SEQ ID NO: 19) or an alanine variant thereof (see, e.g., SEQ ID NOs: 113–129).

In a further embodiment albumin binding polypeptides disclosed herein may be used to assess blood flow in an individual. In this method, a detably labeled HSA binding polypeptide according to the invention is administered to an individual, the labeled polypeptide attaches to serum albumin, and the circulation of the serum protein can be monitored and tracked through the circulatory system of the individual. Such methods for assessing blood flow are particularly useful, for instance, in determining the success of balloon angioplasty, plaque-removal or bypass surgery, or to monitor reperfusion after ischemia, or any instance where assaying the ability of blood to circulate through a treated vessel or to reach a site or organ previously denied blood circulation is important.

These and other aspects of the invention will be described in more detail below.

DETAILED DESCRIPTION OF THE INVENTION

Figure 1:
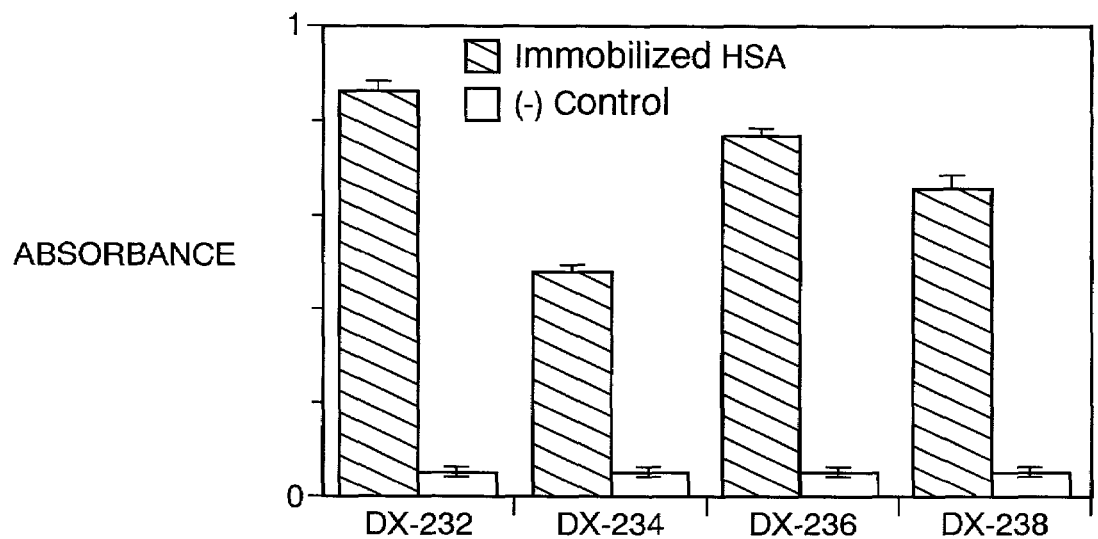
FIG. 1 shows binding (absorbance at 620 nm) to human serum albumin (HSA) by phage isolates displaying binding peptides DX-232, DX-234, DX-236, and DX-238 in an enzyme linked immunosorbent assay (ELISA). Phage were selected as described below from a pool of three phage libraries (TN6/6, TN10/9, TN12/1). Phage were tested for ability to bind to HSA an in ELISA format using caprylate-bound HSA, which had been passively immobilized on the surface of wells of a microtiter assay plate. Binding of phage to immobilized HSA was detected by adding HRP-conjugated anti-M13 antibody. Following addition of TMB substrate, the absorbance at 620 nm was read with an automated plate reader. Phage bound to HSA is shown by diagonal striped bars; control wells (no HSA) is shown by open bars.

This invention provides polypeptides that specifically bind one or more mammalian serum albumin proteins and serum albumin-like polypeptides, i.e., albumin fragments that contain a binding site of full-length serum albumin proteins. The polypeptides of the invention were first isolated by screening libraries of recombinant, filamentous phage that display a population of non-naturally occurring, variegated polypeptides, which polypeptides contain a disulfide-constrained cyclic structure.

Serum albumin binding polypeptides of the invention may be identified by their ability to specifically bind to a serum albumin, or a fragment thereof, under selected conditions, to the exclusion of other polypeptides that do not possess a functional serum albumin binding site.

The peptide compounds of the invention are useful in methods of detecting or isolating serum albumin of one or more mammalian species present in a solution such as whole blood, a blood fraction, and other solutions comprising serum albumin.

In order that the invention may be more fully understood, the following terms are defined:

In the following sections, the term "recombinant" is used to describe non-naturally altered or manipulated nucleic acids, host cells transfected with exogenous nucleic acids, or polypeptides expressed non-naturally, through manipulation of isolated nucleic acid, especially DNA and transformation of host cells. Recombinant is a term that specifically encompasses nucleic acid molecules that have been constructed in vitro using genetic engineering techniques, and use of the term "recombinant" as an adjective to describe a molecule, construct, vector, cell, peptide, or polynucleotide specifically excludes naturally occurring molecules, constructs, vectors, cells, polypeptides or polynucleotides.

The term "bacteriophage" or simply "phage" is defined as a bacterial virus containing a nucleic acid core and a protective shell comprising an aggregation of a number of the same or different protein molecules. Unless otherwise noted, the terms "bacteriophage" and "phage" also encompass "phagemids", i.e., bacteriophage the genome of which includes a plasmid that can be excised by coinfection of a host with a helper phage. A particular phage useful in the isolation of representative serum albumin binding peptides of the invention via phage display technology is a recombinant, single-stranded DNA, filamentous M13 phage.

The term "binding" refers to the determination by standard techniques that a binding moiety recognizes and binds reversibly to a given target. Such standard techniques to detect or measure serum albumin binding include ELISA, equilibrium dialysis, gel filtration, and the monitoring of spectroscopic changes that result from binding, e.g., using fluorescence anisotropy, either by direct binding measurements or competition assays with another binder.

The terms "binding polypeptide" as used herein refers to any molecule, peptide, or peptidomimetic capable of forming a binding complex with another molecule, peptide, peptidomimetic, or transformant. The terms "serum albumin binding moiety", "serum albumin binder", and "serum albumin ligand" are broader terms, used interchangeably, that refer to a molecule comprising a serum albumin binding polypeptide, a phage displaying a binding polypeptide, or a transformed cell expressing a binding polypeptide described herein. A "serum albumin binding moiety" binds and forms a complex with a serum albumin or a serum albumin-like peptide. A "serum albumin binding moiety" also encompasses fragments of the binding polypeptides described herein which specifically bind a serum albumin, modifications of such binding polypeptides made by incorporating the polypeptides (or albumin-binding fragments thereof) in larger polypeptides while still retaining the ability to bind a serum albumin, and derivatives of the binding polypeptides made by conservative amino acid substitutions at any position, so long as substitution does not eliminate the ability to specifically bind to a serum albumin. Specific examples of serum albumin binding moieties of the invention are the polypeptides comprising the amino acid sequences mentioned above (e.g., SEQ ID NOS: 1–20) and phage displaying such serum albumin binding polypeptides.

The term "specificity" refers to a binding moiety having a higher binding affinity for one target over another. The term "serum albumin specificity" refers to a binding moiety having a higher affinity for serum albumin as compared with other proteins, e.g., other serum proteins (e.g., fibrinogen) or ovalbumin. Preferred serum albumin binding moieties described herein will have at least a 10-fold greater affinity for serum albumin than other serum proteins (e.g., fibrinogen, immunoglobulins).

The term "polypeptide" refers to a polymer comprising two or more amino acid residues linked with amide bonds, and the term "peptide" is used herein to refer to relatively short polypeptides, e.g., having fewer than about 30 amino acids. The term "polypeptide" also encompasses the term "protein".

A "disulfide stabilized cyclic polypeptide", "disulfide constrained cyclic polypeptide", "cyclic polypeptide", or simply, "peptide loop" are used interchangeably to refer to a polypeptide having at least one spaced pair of cysteine residues along its length, which cysteine pair is capable of forming a stable cysteine-cysteine disulfide bond at physiological pH, such that the polypeptide secondary structure includes a cyclic peptide structure. The most preferred embodiments of the present invention are peptides having such disulfide constrained cyclic or loop structures including cyclic peptides of 6, 10, or 12 amino acids in length (including the two disulfide-forming cysteine residues).

A "serum albumin-like polypeptide" is any polypeptide comprising at least a fragment of a serum albumin protein, which fragment is capable of being recognized and bound by a serum albumin binding moiety of this invention. Accordingly, "serum albumin-like polypeptide" is a broad term that includes any serum albumin, fragment thereof, mutant form thereof, and any other polypeptide, whether recombinant, non-naturally occurring, or naturally occurring, that is bound by a serum albumin binding moiety of the invention. In addition, the "serum albumin-like polypeptide" includes serum albumin fusion proteins in which a serum albumin or fragment thereof is fused in frame with another polypeptide. In the context of screening for serum albumin binding or using serum albumin binding moieties according to this invention, a serum albumin or a serum albumin-like polypeptide will often be referred to as a "serum albumin target".

The term "detectably labeled" is to be understood as describing linking a serum albumin binding moiety of the invention to a compound, or "label", such as a dye (such as fluorescein); a radionuclide, such as $^{131}I$ or a technetium ($Tc^{99}$)-containing compound; an enzyme (such as horseradish peroxidase); or a detectable metal (such as a paramagnetic ion), wherein the label thereafter provides a signal that can be detected by some appropriate means. The term "detectably labeled" also includes incorporating into a molecule detectable radioactive atoms (such as $^{32}P$, $^{35}S$, or $^{14}C$) in place of a non-radioactive isotope of the same element. "Detectably labeled" also refers to any molecule that is linked or bound to one of a pair of binding partners, whereby detection of the linked (i.e., labeled) molecule is made when the binding partners form a complex. Many such pairs of binding partners are used in standard detection systems known in the art, such binding partners include, without limitation, biotin and streptavidin (either of which may also be conjugated to an enzyme, such as HRP or β-galactosidase, which in turn can be used in a reaction to generate a detectable signal), antibody and epitope binding partners (including epitopes present on the molecule to be detected), and enzyme and substrate binding partners.

In the context of the present invention, the serum albumin binding moieties disclosed herein may be advantageously linked to other compounds, such as diagnostic reagents, therapeutic polypeptides or other drugs, for example to give such compounds improved affinity for serum albumin. In this context, the term "linked" is a broad term encompassing any suitable means of attaching or conjugating the compound of interest to a serum albumin binding moiety of this invention. Many suitable linking means are known in the art and include but are not limited to covalent conjugation, chemical cross-linking via heterobifunctional or homobifunctional cross-linking agents, designing of fusion proteins by linking encoding polynucleotides for the fusion partners (i.e., the albumin binding moiety and a polypeptide of interest) together in-frame for expression of the fused polypeptide, affinity linking such as biotinylation (i.e., for linking to a streptavidin-bearing substrate), ionic links, or any other means by which two or more separate entities may be bound or aggregated to form a single entity or complex.

Phage Display Libraries Used for Serum Albumin Binding Peptides

Specific serum albumin binding polypeptides according to the present invention were isolated initially by screening phage display libraries, that is, populations of recombinant bacteriophage transformed to express on their surface an exogenous cyclic peptide. In order to isolate new polypeptide binding moieties for a particular target, such as serum albumin, screening of large peptide libraries, for example using phage display techniques, is especially advantageous, in that very large numbers (e.g., $5 \times 10^9$) of potential binders can be tested, and successful binders isolated in a short period of time.

Display libraries exhibiting variegated heterologous peptides on the surface of recombinant phage or other genetic packages (bacteria, yeast, other host cells) may be prepared in any of several ways known in the art. See, e.g., Kay et al., *Phage Display of Peptides and Proteins: A Laboratory Manual* (Academic Press, Inc., San Diego 1996) and U.S. Pat. No. 5,223,409 (Ladner et al.), both incorporated herein by reference.

In isolating the specific peptides according to this invention, six different phage libraries were screened, each displaying a short, variegated exogenous peptide on the surface of M13 phage. The peptide display of five of the libraries was based on a parental domain having a segment of 4, 6, 7, 8, or 10 amino acids, respectively, flanked by cysteine residues. The pairs of cysteines are believed to form stable disulfide bonds, yielding a cyclic display peptide. The cyclic peptides are displayed at the amino terminus of protein III on the surface of the phage. The libraries were designated TN6/6, TN8/9, TN9/4, TN10/9, and TN12/1. A phage library with a 20-amino acid linear display was also screened; this library was designated Lin20.

The TN6/6 library used to obtain peptide binding moieties of the invention was constructed to display a single cyclic peptide contained in a 12-amino acid variegated template. The TN6/6 library utilized a template sequence of $Xaa_1$-$Xaa_2$-$Xaa_3$-$Cys_4$-$Xaa_5$-$Xaa_6$-$Xaa_7$-$Xaa_8$-$Cys_9$-$Xaa_{10}$-$Xaa_{11}$-$Xaa_{12}$ (SEQ ID NO: 21), where each variable amino acid position in the amino acid sequence of the template is indicated by a subscript integer. Each variable amino acid position (Xaa) in the template was varied, independently, to permit the following substitutions: residues $Xaa_1$ and $Xaa_{12}$ were varied to contain any of the following 14 amino acids: Ala, Asp, Phe, Gly, His, Leu, Asn, Pro, Gln, Arg, Ser, Val, Trp, and Tyr; and residues $Xaa_2$, $Xaa_3$ $Xaa_5$, $Xaa_6$, $Xaa_7$, $Xaa_8$, $Xaa_{10}$, and $Xaa_{11}$ were independently varied to contain any of the common α-amino acids, except cysteine (Cys). The number of potential designed sequences is $3.3 \times 10^{12}$; $2.0 \times 10^8$ independent transformants were included in the library.

The TN8/9 library was constructed to display a single microprotein binding loop contained in a 14-amino acid template. The TN8/9 library utilized a template sequence of $Xaa_1$-$Xaa_2$-$Xaa_3$-Cys-$Xaa_5$-$Xaa_6$-$Xaa_7$-$Xaa_8$-$Xaa_9$-$Xaa_{10}$-Cys-$Xaa_{12}$-$Xaa_{13}$-$Xaa_{14}$ (SEQ ID NO: 235). The amino acids at position 1, 2, 3, 5, 6, 7, 8, 9, 10, 12, 13, and 14 in the template were varied to permit any amino acid except cysteine (Cys).

The TN9/4 library was constructed to display a single microprotein binding loop contained in a 15-amino acid template. The TN9/4 library utilized a template sequence $Xaa_1$-$Xaa_2$-$Xaa_3$-Cys-$Xaa_5$-$Xaa_6$-$Xaa_7$-$Xaa_8$-$Xaa_9$-$Xaa_{10}$-$Xaa_{11}$-Cys-$Xaa_{13}$-$Xaa_{14}$$Xaa_{15}$ (SEQ ID NO: 236). The amino acids at position 1, 2, 3, 5, 6, 7, 8, 9, 10, 11, 13, 14 and 15 in the template were varied to permit any amino acid except cysteine (Cys).

The TN10/9 library was constructed to display a single cyclic peptide contained in a 16-amino acid variegated template. The TN10/9 library utilized a template sequence $Xaa_1$-$Xaa_2$-$Xaa_3$-$Cys_4$$Xaa_5$-$Xaa_6$-$Xaa_7$-$Xaa_8$-$Xaa_9$-$Xaa_{10}$-

$Xaa_{11}$-$Xaa_{12}$-$Cys_{13}$-$Xaa_{14}$$Xaa_{15}$-$Xaa_{16}$ (SEQ ID NO: 22), where each variable amino acid position in the amino acid sequence of the template is indicated by a subscript integer. Each variable amino acid position (Xaa) was varied independently to permit the following substitutions. The amino acid positions $Xaa_1$, $Xaa_2$, $Xaa_{15}$ and $Xaa_{16}$ of the template were varied, independently, to permit each of the amino acids selected from a group of ten amino acids consisting of Asp, Phe, His, Leu, Asn, Pro, Arg, Ser, Trp, and Tyr; the amino acids at amino acid positions $Xaa_3$ and $Xaa_{14}$ in the template were varied, independently, to permit each amino acid selected from the group of fourteen amino acids consisting of Ala, Asp, Glu, Phe, Gly, His, Leu, Asn, Pro, Arg, Ser, Val, Trp, and Tyr; the amino acids at amino acid positions $Xaa_5$, $Xaa_6$, $Xaa_7$, $Xaa_8$, $Xaa_9$, $Xaa_{10}$, $Xaa_{11}$ and $Xaa_{12}$ (i.e., between the invariant cysteine residues at positions 4 and 13 in the template) were varied, independently, to permit each of the common α-amino acids, except cysteine. The number of potential designed sequences is $3.0 \times 10^{16}$; and about $2.5 \times 10^8$ independent transformants were included in the library.

The TN12/1 library was constructed to display a single cyclic peptide contained in an 18-amino acid template. The TN12/1 library utilized a template sequence $Xaa_1$-$Xaa_2$-$Xaa_3$-$Cys_4$$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Cys_{15}$-$Xaa_{16}$-$Xaa_{17}$-$Xaa_{18}$ (SEQ ID NO: 23), where each variable amino acid position in the amino acid sequence of the template is indicated by a subscript integer. The amino acid positions $Xaa_1$, $Xaa_2$, $Xaa_{17}$ and $Xaa_{18}$ of the template were varied, independently, to permit each amino acid selected from the group of 12 amino acids consisting of Ala, Asp, Phe, Gly, His, Leu, Asn, Pro, Arg, Ser, Trp, and Tyr. The amino acid positions $Xaa_3$, $Xaa_5$, $Xaa_6$, $Xaa_7$, $Xaa_8$, $Xaa_9$, $Xaa_{10}$, $Xaa_{11}$, $Xaa_{12}$, $Xaa_{13}$, $Xaa_{14}$, $Xaa_{16}$, of the template were varied, independently, to permit each of the common a-amino acids, except cysteine.

The Lin20 library was constructed to display a single linear peptide in a 20-amino acid template. The amino acids at each position in the template were varied to permit any amino acid except cysteine (Cys).

The small serum albumin binding peptides described herein offer several advantages over large proteins: First, the mass per binding site is reduced, e.g., such highly stable and low molecular weight polypeptide domains can show much higher binding per gram than do antibodies (approximately 150 kDa) or single-chain antibodies (approximately 30 kDa). Second, the possibility of non-specific binding is reduced because there is less surface available. Third, small proteins or polypeptides can (because they are chemically synthesizable) be engineered to have unique tethering sites such as terminal polylysine segments in a way that is impracticable for larger proteins or antibodies. Fourthly, small peptides can be combined into homo- or hetero-multimers to give either hybrid binding or avidity effects.

As indicated previously, the techniques discussed in Kay et al., *Phage Display of Peptides and Proteins: A Laboratory Manual* (Academic Press, Inc., San Diego 1996) and U.S. Pat. No. 5,223,409 are particularly useful in preparing a library of potential binders corresponding to the selected parental template. The libraries described above were prepared according to such techniques, and they were screened for binding peptides against a human serum albumin (HSA) target, either immobilized on a solid surface or free in solution.

Screening Phage Display Libraries for Serum Albumin Binding Peptides

In a typical screen, a phage library is contacted with and allowed to bind the target, in this case HSA or a particular fragment or subcomponent thereof. To facilitate separation of binders and non-binders in the screening process, it is often convenient to immobilize the target on a solid support, although it is also possible to first permit binding to the target in solution and then segregate binders from non-binders (see Examples below). By way of illustration, when incubated in the presence of the target, phage bearing a target-binding moiety form a complex with the target, for example, immobilized on a solid support whereas non-binding phage remain in solution and may be washed away with buffer. Bound phage may then be liberated from the target by a number of means, such as changing the buffer to a relatively high acidic or basic pH (e.g., pH 2 or pH 10), changing the ionic strength of the buffer, adding denaturants, or other known means.

For example, HSA can be adsorbed (by passive immobilization) to a solid surface, such as the plastic surface of wells in a multi-well assay plate, and then an aliquot of a phage display library was added to a well under appropriate conditions that maintain the structure of the immobilized HSA and the phage, such as pH 6–7. Phage in the libraries that display peptide loop structures that bind the immobilized HSA will be retained bound to the HSA adhering to the surface of the well and non-binding phage can be removed. Phage bound to the immobilized HSA may then be eluted by washing with a buffer solution having a relatively strong acid pH (e.g., pH 2) or an alkaline pH (e.g., pH 8–9). The solutions of recovered phage that are eluted from the HSA are then neutralized and may, if desired, be pooled as an enriched mixed library population of phage displaying serum albumin binding peptides. Alternatively the eluted phage from each library may be kept separate as a library-specific enriched population of HSA binders. Enriched populations of phage displaying serum albumin binding peptides may then be grown up by standard methods for further rounds of screening and/or for analysis of peptide displayed on the phage and/or for sequencing the DNA encoding the displayed binding peptide.

One of many possible alternative screening protocols uses HSA target molecules that are biotinylated and that can be captured by binding to streptavidin, for example, coated on particles. As is described in an example below, phage displaying HSA binding peptides were selected from a library in such a protocol in which phage displaying HSA binding peptides were bound to a caprylate-biotinylated-HSA in solution at pH 7.4 in phosphate buffered saline (PBS) supplemented with 0.1% TWEEN 20® nonionic detergent and also 0.1% sodium caprylate, which is known to stabilize HSA against temperature-induced denaturation and proteolytic attack. The caprylate-biotinylated-HSA!phage complexes in solution were then captured on streptavidin-coated magnetic beads. Phage were subsequently eluted from the beads for further study.

Recovered phage may then be amplified by infection of bacterial cells, and the screening process may be repeated with the new pool of phage that is now depleted in non-HSA binders and enriched in HSA binders. The recovery of even a few binding phage is sufficient to carry the process to completion. After a few rounds of selection, the gene sequences encoding the binding moieties derived from selected phage clones in the binding pool are determined by conventional methods, revealing the peptide sequence that imparts binding affinity of the phage to the target. An increase in the number of phage recovered after each round of selection and the recovery of closely related sequences indicate that the screening is converging on sequences of the library having a desired characteristic.

After a set of binding polypeptides is identified, the sequence information may be used to design other, secondary libraries, biased for members having additional desired properties.

Serum Albumin Binding Polypeptides and Moieties

After analysis of the nucleotide sequence of DNA isolated from the library screenings, families of particular serum albumin binding peptides were defined.

By analysis of the TN6/6 variegated template sequences, a family of serum albumin binding polypeptides is defined comprising polypeptides including the amino acid sequence of formula I:

I. $Xaa_1$-$Xaa_2$-$Xaa_3$-Cys-$Xaa_4$-$Xaa_5$-$Xaa_6$-$Xaa_7$-Cys-$Xaa_8$-$Xaa_9$-$Xaa_{10}$ (SEQ ID NO: 2), wherein $Xaa_1$ is Asn, His, Leu, Phe, Trp, or Val; $Xaa_2$ is Ala, Glu, His, Lys, Trp, or Val; $Xaa_3$ is Asp, Gly, Ile, His, Ser, Trp, or Val; $Xaa_4$ is Asp, Asn, Ser, Thr, or Trp; $Xaa_5$ is Asn, Gln, His, Ile, Leu, or Lys; $Xaa_6$ is Ala, Asp, Phe, Trp, or Tyr; $Xaa_7$ is Asp, Gly, Leu, Phe, Ser, or Thr; $Xaa_8$ is Glu, Ile, Leu, Met, Ser, or Val; $Xaa_9$ is Asn, Asp, Glu, Gly, Met, Ser, or Trp; and $Xaa_{10}$ is Ala, Asn, Asp, Pro, Tyr, or Val.

Analysis of the TN8/9 template sequences defines a family of serum albumin binding polypeptides comprising polypeptides including the amino acid sequence of formula II:

II. $Xaa_1$-$Xaa_2$-$Xaa_3$-Cys-$Xaa_4$-$Xaa_5$-$Xaa_6$-$Xaa_7$-$Xaa_8$-$Xaa_9$-Cys-$Xaa_{10}$-$Xaa_{11}$-$Xaa_{12}$ (SEQ ID NO: 131), wherein $Xaa_1$ is Ala, Gln, Leu, Lys, Phe, Trp, or Tyr; $Xaa_2$ is Asn, Gln, Glu, Ile, Thr, or Trp; $Xaa_3$ is Asn, Gly, Phe, Thr, Trp, or Tyr; $Xaa_4$ is Ala, Leu, His, Met, Phe, Ser, or Thr; $Xaa_5$ is Ile, Phe, Pro, Ser, Trp, or Tyr; $Xaa_6$ is Asp, Gln, Glu, Lys, Pro, Trp, or Tyr; $Xaa_7$ is Asp, Gln, Gly, Leu, Pro, or Trp; $Xaa_8$ is Asp, Ile, Leu, Lys, Met, Pro, Trp, or Tyr; $Xaa_9$ is Gln, Gly, Ile, Phe, Thr, Trp, or Val; $Xaa_{10}$ is Asp, Glu, Gly, Leu, Lys, Pro, or Ser; $Xaa_{11}$ is Glu, His, Ile, Leu, Lys, Ser, Trp, or Val; and $Xaa_{12}$ is Ala, Asn, His, Ile, Met, Phe, Pro, or Ser.

Analysis of the TN10/9 template sequences defines a family of serum albumin binding polypeptides comprising polypeptides including the amino acid sequence of formula III: $Xaa_1$-$Xaa_2$-$Xaa_3$-Cys-$Xaa_4$-$Xaa_5$-$Xaa_6$-$Xaa_7$-$Xaa_8$-$Xaa_9$-$Xaa_{10}$-$Xaa_{11}$-Cys-$Xaa_{12}$-$Xaa_{13}$-$Xaa_{14}$ (SEQ ID NO: 134), wherein $Xaa_1$ is Arg, Phe, or Tyr; $Xaa_2$ is Arg, Leu, Ser, or Trp; $Xaa_3$ is Asn, Asp, Phe, or Tyr; $Xaa_4$ is Gln, Glu, Phe, or Met; $Xaa_5$ is Asp, Pro, or Thr; $Xaa_6$ is Ile, Ser, or Trp; $Xaa_7$ is His, Met, Phe or Pro; $Xaa_8$ is Asn, Leu, or Thr; $Xaa_9$ is Arg, Asn, His, or Thr; $Xaa_{10}$ is Arg, Met, Phe, or Tyr; $Xaa_{11}$ is Asp, Gly, Phe, or Trp; $Xaa_{12}$ is Ala, Asn, or Asp; $Xaa_{13}$ is Arg, Phe, Pro, or Tyr; and $Xaa_{14}$ is Arg, His, Phe, or Ser.

Analysis of the TN12/1 template sequences defines a family of serum albumin binding polypeptides comprising polypeptides including the amino acid sequence of formula IV:

IV. $Xaa_1$-$Xaa_2$-$Xaa_3$-Cys-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-Cys-$Xaa_{14}$-$Xaa_{15}$-$Xaa_{16}$ (SEQ ID NO: 5), wherein $Xaa_1$ is Ala, Arg, Asp, Asn, Gly, His, Leu, Phe, Pro, Ser, Trp, Tyr; $Xaa_2$ is Ala, Arg, Asp, Asn, Gly, His, Phe, Pro, Ser, or Trp; $Xaa_3$ is Ala, Asn, Asp, Gln, Gly, His, Leu, Met, Phe, Ser, Thr, Trp, Tyr, or Val; $Xaa_4$ is Ala, Asn, Asp, Gln, Glu, Gly, Ile, Leu, Lys, Phe, Pro, Ser, Thr, Trp, Tyr, or Val; $Xaa_5$ is Ala, Arg, Asp, Glu, Gly, His, Ile, Leu, Lys, Met, Phe, Ser, Thr, Trp, Tyr, or Val; $Xaa_6$ is Ala, Arg, Asp, Gln, Glu, Gly, Ile, Leu, Lys, Met, Pro, Ser, Thr, Trp, Tyr, or Val; $Xaa_7$ is Ala, Arg, Asn, Asp, Ile, Leu, Phe, Pro, Ser, Trp, or Tyr; $Xaa_8$ is Ala, Asp, Glu, Gly, Ile, Met, Phe, Pro, Thr, Trp, or Tyr; $Xaa_9$ is Ala, Arg, Asn, Asp, Gln, Glu, His, Ile, Leu, Lys, Phe, Ser, Thr, Trp, or Tyr; $Xaa_{10}$ is Ala, Arg, Asp, Glu, Gly, His, Met, Phe, Pro, Ser, Thr, or Trp; $Xaa_{11}$ is Ala, Arg, Asp, Gln, Glu, His, Ile, Leu, Met, Phe, Pro, Ser, Thr, Trp, or Val; $Xaa_{12}$ is Ala, Arg, Asp, Glu, Gln, His, Ile, Leu, Lys, Met, Phe, Pro, Ser, Thr, Trp, Tyr, or Val; $Xaa_{13}$ is Ala, Asp, Gln, Glu, Gly, His, Ile, Leu, Lys, Phe, Pro, Ser, Thr, Trp, Tyr, or Val; $Xaa_{14}$ is Ala, Arg, Asn, Asp, Glu, Gly, His, Ile, Leu, Lys, Met, Pro, Ser, Thr, Trp, or Tyr; $Xaa_{15}$ is Ala, Arg, Asn, Asp, Gly, His, Leu, Phe, Pro, Ser, Trp, or Tyr; and $Xaa_{16}$ is Ala, Asn, Asp, Gly, His, Leu, Phe, Pro, Ser, Trp, or Tyr.

The cysteine residues of the displayed heterologous peptide structures are believed to form a disulfide bond, which causes the peptide to exhibit a stable cyclic structure under non-reducing conditions. Thus, analysis of the isolate families from the TN6/6, TN8/9, TN10/9, and TN12/1 libraries defines particular serum albumin binding moieties comprising cysteine-bracketed polypeptides including one of the following amino acid sequences V, VI, VII or VIII:

V. Cys-$Xaa_1$-$Xaa_2$-$Xaa_3$-$Xaa_4$-Cys (SEQ ID NO: 1), wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr; or VI. Cys-$Xaa_1$-$Xaa_2$-$Xaa_3$-$Xaa_4$-$Xaa_5$-$Xaa_6$-Cys (SEQ ID NO: 130)

wherein $Xaa_1$ is Ala, Leu, His, Met, Phe, Ser, or Thr; $Xaa_2$ is Ile, Phe, Pro, Ser, Trp, or Tyr; $Xaa_3$ is Asp, Gln, Glu, Lys, Pro, Trp, or Tyr; $Xaa_4$ is Asp, Gln, Gly, Leu, Pro, or Trp; $Xaa_5$ is Asp, Ile, Leu, Lys, Met, Pro, Trp, or Tyr; $Xaa_6$ is Gln, Gly, Ile, Phe, Thr, Trp, or Val; or VII. Cys-$Xaa_1$-$Xaa_2$-$Xaa_3$-$Xaa_4$-$Xaa_5$-$Xaa_6$-$Xaa_7$-$Xaa_8$-Cys (SEQ ID NO: 133), wherein $Xaa_1$ is Gln, Glu, Phe, or Met; $Xaa_2$ is Asp, Pro, or Thr; $Xaa_3$ is Ile, Ser, or Trp; $Xaa_4$ is His, Met, Phe or Pro; $Xaa_5$ is Asn, Leu, or Thr; $Xaa_6$ is Arg, Asn, His, or Thr; $Xaa_7$ is Arg, Met, Phe, or Tyr; $Xaa_8$ is Asp, Gly, Phe, or Trp.

VIII. Cys-$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-Cys (SEQ ID NO: 4), wherein $Xaa_1$ is Ala, Asn, Asp, Gln, Glu, Gly, Ile, Leu, Lys, Phe, Pro, Ser, Thr, Trp, Tyr, or Val; $Xaa_2$ is Ala, Arg, Asp, Glu, Gly, His, Ile, Leu, Lys, Met, Phe, Ser, Thr, Trp, Tyr, or Val; $Xaa_3$ is Ala, Arg, Asp, Gln, Glu, Gly, Ile, Leu, Lys, Met, Pro, Ser, Thr, Trp, Tyr, or Val; $Xaa_4$ is Ala, Arg, Asn, Asp, Ile, Leu, Phe, Pro, Ser, Trp, or Tyr; $Xaa_5$ is Ala, Asp, Glu, Gly, Ile, Met, Phe, Pro, Thr, Trp, or Tyr; Xaac is Ala, Arg, Asn, Asp, Gln, Glu, His, Ile, Leu, Lys, Phe, Ser, Thr, Trp, or Tyr; $Xaa_7$ is Ala, Arg, Asp, Glu, Gly, His, Met, Phe, Pro, Ser, Thr, or Trp; $Xaa_8$ is Ala, Arg, Asp, Gln, Glu, His, Ile, Leu, Met, Phe, Pro, Ser, Thr, Trp, or Val; $Xaa_9$ is Ala, Arg, Asp, Gln, Glu, His, Ile, Leu, Lys, Met, Phe, Pro, Ser, Thr, Trp, Tyr, or Val; $Xaa_{10}$ is Ala, Asp, Gln, Glu, Gly, His, Ile, Leu, Lys, Phe, Pro, Ser, Thr, Tyr, or Val.

Additional alanine mutants of a serum albumin binding polypeptide isolated from the TN12/1 library demonstrated that alanine should also be added to the possible values for the variable amino acid positions in formulas IV and VIII, above (see, Example 2, infra).

Polypeptides according to the invention may be prepared in a variety of ways:

Direct synthesis of the polypeptides of the invention may be accomplished using conventional techniques, including solid-phase peptide synthesis, solution-phase synthesis, etc. Solid-phase synthesis is preferred. See Stewart et al., *Solid-Phase Peptide Synthesis* (1989), W. H. Freeman Co., San Francisco; Merrifield, *J. A.m. Chem. Soc.*, 85:2149-2154 (1963); Bodanszky and Bodanszky, *The Practice of Peptide Synthesis*(Springer-Verlag, New York 1984), incorporated herein by reference.

Polypeptides according to the invention may also be prepared commercially by companies providing peptide synthesis as a service (e.g., BACHEM Bioscience, Inc., King of Prussia, Pa; Quality Controlled Biochemicals, Inc., Hopkinton, Mass.).

Automated peptide synthesis machines, such as those manufactured by Perkin-Elmer Applied Biosystems, also are available.

For producing binding polypeptides using recombinant DNA methods, a variety of expression vector systems are currently available which permit the insertion and expression of a polynucleotide sequence encoding a polypeptide. Such vectors include, for example, eukaryotic and prokaryotic expression plasmids, recombinant bacteriophage, recombinant eukaryotic viral vectors, artificial chromosomes, and the like, which also contain the transcription and translation control signals necessary for expression of the polypeptide in an appropriate host cell. In this approach, a polynucleotide sequence encoding a serum albumin binding peptide of the invention is synthesized, e.g., using an automated DNA synthesizer, and inserted using standard methods into a selected expression vector. The resulting recombinant expression vector containing the inserted polynucleotide is then inserted into an appropriate host cell, e.g., using transformation, electroporation, microprojectiles, liposome-mediated transformation, transfection, and the like. Host cells containing the recombinant expression vector are then incubated in appropriate conditions to permit expression of the serum albumin binding peptide, which may then be purified away from host cell proteins.

Although recombinant DNA methods are well developed for expressing heterologous polypeptides and proteins, the relatively small size of the serum albumin binding polypeptides of the invention favors the use of automated peptide synthesis as the more preferred method of producing the peptides. In addition, in vitro peptide synthesis methods permit modifications to be made on the binding peptide, such as the addition of an amino and/or a carboxy terminal capping group, which can protect the binding peptide from degradation or undesired reaction with other molecules, and/or which can provide additional groups that add to the versatility of the peptides, such as incorporating a functional group that permits coupling to an activated affinity resin, such as activated N-hydroxysuccinimide (NHS)-SEPHAROSE® affinity chromatography resin particles. Binding peptides produced by standard automated peptide synthesis procedures can be easily purified, e.g., using standard reverse phase high performance liquid chromatography (HPLC), in useful amounts.

The binding properties of a serum albumin binding moiety of the invention, either as purified binding peptides or phage displaying binding peptides, can be readily assessed using various assay formats known in the art. Such methods include fluorescence anisotropy, which provides a convenient and accurate method of determining a dissociation constant ($K_D$) of a binding moiety for a serum albumin from one or more different species. In one such procedure, a binding moiety described herein is labeled with fluorescein. The fluorescein-labeled binding moiety may then be mixed in wells of a multi-well assay plate with various concentrations of a particular species of serum albumin. Fluorescence anisotropy measurements are then carried out using a fluorescence polarization plate reader (see, Examples).

Another format to detect or measure binding to a serum albumin in a solution uses a setup based on standard enzyme linked immunosorbent assays (ELISAs) in which a target serum albumin is immobilized on the surface of the wells of a multi-well assay plate, and a solution comprising a serum albumin binding moiety (polypeptide or phage) is added to the wells. The binding moiety will, under appropriate conditions, bind to the immobilized serum albumin, and unbound components of the solution may then be removed from the well. The presence of any binding moiety retained in the wells can then be detected with a labeled antibody (or other labeled molecule) that will bind to the binding moiety. The label on the antibody is preferably an enzyme, such as HRP, which is capable of generating a detectable signal in the presence of an appropriate substrate (TMB in the case of HRP). The intensity of the signal is proportional to the amount of binding moiety bound to the serum albumin.

A serum albumin binding moiety described herein may be linked (covalently or non-covalently) to various molecules and particles (i.e., in addition to binding to a serum albumin), including but not limited to the surface of finely divided chromatography resin particles, the surface of magnetic particles or microspheres, radionuclides, magnetic resonance imaging compounds, other polypeptides, enzymes, proteins present on of the surface cells, streptavidin, biotin, antibodies, and therapeutic compounds. A variety of methods for linking two molecules together are known in the art. Such linkages are preferably covalent linkages, although in some arrangements, a serum albumin binding moiety of the invention may be linked to another molecule by hydrophobic or ionic linkages, or even some combination of various types of bonds. Covalent linkages useful in linking a serum albumin binding moiety described herein to another molecule include, but are not limited, to peptide linkages, disulfide linkages, ester linkages, and ether linkages. For example, an amino group of the side chain of a lysine residue present in a serum albumin binding moiety of the invention may be used to covalently link the binding moiety to another protein, surface, or particle via condensation to form a peptide bond. If a serum albumin binding polypeptide of the invention is to be linked to another polypeptide of known amino acid sequence, then a fusion polypeptide comprising the two constituent molecules may be synthesized directly using an automated peptide synthesizer or using any of the various standard recombinant DNA methods known in the art for producing fusion proteins.

Covalent linking of a serum albumin binding polypeptide or moiety of the invention to another molecule may also be achieved using any of a variety of coupling agents and protocols known in the art. Such coupling agents include, but are not limited to, non-specific coupling agents, such as glutaraldehyde; heterobifunctional coupling agents, which can link two different molecules using a different chemical reaction for each component molecule; and homobifunctional coupling agents, which can link two different molecules using the same chemical reaction for each component molecule.

Serum albumin binding moieties of the invention may also be immobilized to the surface of a solid support material. Such solid support materials include, but are not limited to, paper, glass, plastic, wood, nylon, rubber, metal, acrylamide, cellulose, agarose, and combinations thereof. Such solid surfaces may be found in a variety of compositions, including but not limited to, wells of a multi-well assay plate, magnetic particles or beads, chromatographic resin particles, and various tubes and containers for assays and storage. A serum albumin binding moiety may be linked to such surfaces by any of the possible types of known chemical bonds, such as covalent linkage, hydrophobic interaction, ionic linkage, and combinations thereof. For example, in some cases, a serum albumin binding polypeptide or moiety may simply adhere to a solid surface, such as the surface of wells of a multi-well assay plate. Alternatively, a serum albumin binding moiety may be immobilized to a solid surface using a linker molecule that tethers the binding moiety from the surface of the solid support material. In still another arrangement, the streptavidin-biotin partners may be employed to immobilize a binding moiety to the surface of solid support material (see, Examples).

When immobilized on solid supports such as magnetic beads, filters, or chromatography media, the binding moieties of the present invention provide useful separation media for the recovery of serum albumin or serum albumin-like polypeptides, including serum albumin fusion proteins, from solutions including whole blood, blood fractions, and conditioned media containing recombinant serum albumin or serum albumin-like polypeptides.

Whatever means is used to link a binding moiety described herein to another molecule, the desired final product is preferably a compound in which there has been no significant loss of the desired characteristics of each of the component molecules: in the case of the serum albumin binding moiety component, there is preferably no significant reduction in the ability to bind serum albumin. More preferably, linkage of a binding moiety described herein with another molecule results in enhanced properties, such as enhanced detectability, increased serum half-life, enhanced solubility, or enhanced therapeutic efficacy.

Uses for Serum Albumin Binding Moieties of the Invention

For detection of serum albumin in a solution, such as blood or conditioned media suspected of containing it, a serum albumin binding moiety described herein may be detectably labeled, e.g., radiolabeled or enzymatically labeled, using standard methods, then contacted with the solution in which the binding moiety binds and forms a complex with the serum albumin. Thereafter, formation of the binding moiety/serum albumin complex may be detected by any of a variety of standard methods. For example, a recombinant phage displaying a serum albumin binding polypeptide on its surface, may form a complex with serum albumin that is detectable as a sediment in a reaction tube, which may be detected visually after settling or centrifugation. As another example, a sandwich-type assay may be used in which a serum albumin binding moiety described herein is immobilized on a solid support such as the wall of a plastic tube, the surface of a well in a multi-well assay plate, or a chromatographic matrix particle. A solution suspected of containing a serum albumin is then contacted with the immobilized binding moiety, and non-binding components of the solution are removed or washed away. Any serum albumin bound to the immobilized serum binding moiety is detected using a suitable detection reagent, such as a monoclonal antibody recognizing the serum albumin target, which reagent is detectable by some conventional means known in the art, such as a radiolabel or conjugated enzyme that produces a detectable signal.

The serum albumin binding moieties according to this invention are also useful for isolating serum albumin from a solution by affinity chromatography. For example, a serum albumin binding moiety of the invention may be linked by methods available in the art to the surface of a finely divided chromatography matrix resin, such as N-hydroxysuccinimide (NIIS)-SEPHAROSE® affinity resin particles, to make a serum albumin-specific affinity chromatography resin. The immobilized binding moiety can then be loaded or contacted with a feed stream under conditions favorable to formation of binding moiety/serum albumin complexes. Non-binding components can be removed or washed away, then the serum albumin can be eluted by introducing solution conditions favoring dissociation of the binding complex.

Alternatively, a serum albumin may be isolated or detected by combining a solution containing the serum albumin with a serum albumin binding moiety described herein, then isolating complexes of the serum albumin and the serum albumin binding moiety. For this type of separation, many methods are known for which a serum albumin binding moiety may be employed as the binding reagent. For example, a serum albumin binding moiety of the invention can be immobilized on a solid support, then separated from the feed stream along with any serum albumin bound to the binding moiety by filtration. Alternatively, a binding moiety described herein may be modified with its own affinity tag, such as a polyHis tail, which can be used to capture (bind) the binding moiety after complexes have formed using metal affinity chromatography. Once separated, the serum albumin target can be released from the binding molecule under suitable elution conditions and recovered in pure form. Any other affinity tag and its binding partner (e.g., biotin/streptavidin, Fc/protein A, and the like) may be used in this way to make an albumin binding moiety according to the invention capable of being captured or immobilized as described above.

It should be noted that although precise binding conditions were preselected in obtaining the serum albumin binding moieties disclosed herein, subsequent use in affinity purification may reveal more optimal binding and release conditions under which the same isolated affinity ligand will operate. Thus, it is not critical that the binding moiety, after isolation according to this invention, be always employed only at the binding and release conditions that led to its separation from the library.

It is also understood that methods of detecting and isolating serum albumin, as described herein, may also be used to detect and isolate serum albumin-like polypeptides, especially serum albumin fusion proteins comprising a serum albumin or portion thereof linked to another polypeptide (see, e.g., regarding HSA fusion proteins described in Hollon, *Nature Biotechnology*, 18: 1238–1239 (2000); Yeh et al., *Proc. Natl. Acad. Sci. USA*, 89(5): 1904–1908 (1992)).

Since serum albumin is the most abundant protein marker in blood, serum albumin binding moieties described herein may be used as reagents to localize and image blood in an individual. Such "blood pool imaging" methods typically will use magnetic resonance imaging (MRI) to obtain images of the blood in various tissues, e.g., to detect circulation or lack of it in blood vessels or to detect reperfusion of organs to which blood flow was previously blocked. See, e.g., WO 97/30734. According to the invention, a serum albumin binding moiety is linked by standard methods to a detectable label. The labeled binding moiety is then administered to an individual, who is scanned with the appropriate detection apparatus to obtain an image of the blood in the tissue. Such blood pool imaging is particularly useful in imaging circulating blood, blockages in circulatory blood (ischemia), and in locating sites of internal bleeding in the tissues of an individual or deep vein thrombosis. See, e.g., Seabold, *Semin. Nucl. Med.*, 31(2):124–128 (2001); Saeed et al., *J. Mag. Res. Imaging*, 12(6):890–898 (2000).

It is understood that using the detection or isolation methods described herein, serum albumin (or serum albumin-like protein) may be detected in or isolated from any of a variety of solutions that may contain serum albumin. Such solutions include, but are not limited to, blood and blood fractions, extracts of eukaryotic cells that express serum albumin, extracts of recombinant prokaryotic cells that express a serum albumin, and various solutions or cell extracts from transgenic animals that have been genetically engineered to express a serum arm albumin, such as egg white from a transgenic chicken (or other poultry).

Another use for the binding moieties of the invention is to increase the half-life and overall stability of a therapeutic or diagnostic compound that is administered to or enters the circulatory system of an individual. See, e.g., U.S. Pat. No. 5,116,944; EP-A2-395 918; WO 91/01743. In such methods, a serum albumin binding moiety described herein is used to link a therapeutic or diagnostic compound to a serum albumin found in the blood of an individual who will receive the therapeutic or diagnostic compound. In this embodiment, a serum albumin binding moiety of the invention is linked, covalently or non-covalently (see above), to a selected therapeutic or diagnostic compound at a site that keeps the serum albumin binding site of the moiety intact and still capable of binding to a serum albumin, without compromising the desired diagnostic or therapeutic activity. In this way, the binding moiety serves as a linker molecule to link the diagnostic/therapeutic compound of interest to a serum albumin circulating in the blood. Linking a diagnostic or therapeutic compound to circulating serum albumin using a serum albumin binding moiety of the invention is expected to be particularly useful in increasing the circulating half-life and/or overall stability of compounds that are normally subject to an undesirably rapid rate of degradation or clearance from circulation. Increasing the half-life or overall stability of a compound in the circulatory system is likely to reduce the number and/or size of doses that must be administered to an individual to obtain a desired effect. Any suitable diagnostic compound may be linked to serum albumin in this manner, including, especially detectable labels, which may be dyes dye (such as fluorescein); radiolabels such as $^{131}$I or a technetium ($Tc^{99}$)-containing compound; enzymes (such as horseradish peroxidase); or a detectable metal (such as a paramagnetic ion). Any suitable therapeutic compound may be linked to serum albumin in this manner, including drugs, biopharmaceuticals, and any polypeptide of interest. Examples of such therapeutics suitable for linking to serum albumin include but are not limited to receptor agonists or antagonists, specific binding compounds, enzyme inhibitors, metal chelators, molecular scavengers such as vitamin E, and the like. Of particular interest for this use are thrombin inhibitors, thrombolytics (such as tPA and urokinase), renin inhibitors, Ace inhibitors, selectin ligands, inhibitors of the coagulation cascade, complement regulatory molecules (such as DAF, CR1, CR2, C4bp, factor H), serine proteases, GPIIb/IIIa antagonists, CRF antagonists, and the like.

Isolation and characterization of serum albumin binding moieties in accordance with this invention will be further illustrated below. The specific parameters included in the following examples are intended to illustrate the practice of the invention, and they are not presented to in any way limit the scope of the invention.

EXAMPLES

Example 1

Selection of Human Serum Albumin Binding Polypeptides

Reagents

Human serum (type AB) was purchased from Sigma Chemical Company (St. Louis, Mo.). Affinity purified monomeric human serum albumin (HSA) was purchased from ICN. All other mammalian albumins were purchased as Fraction V purified material from Sigma Chemical Company. N-Hydroxysuccinimide (NHS) activated SEPHAROSE® chromatography resin was purchased from Amersham-Pharmacia Biotech (Piscataway, N.J.). All chromatographic columns were purchased from OMNIFIT.TM. Inc. (Rockville Center, N.Y.). All other chemicals were of the highest grade available. Level 1 Sera-Mag streptavidin magnetic beads were purchased from Seradyn (Indianapolis, md.). NHS-LC-LC-Biotin was purchased from Pierce Chemical Company (Rockland, Ill.) for the biotinylation of HSA.

HSA Selection Protocol for Passively Immobilized HSA Screening

Three phage libraries (TN6/6, TN10/9, and TN12/1) were selected against caprylate-bound HSA (10 μg/ml at 100 μl/well) in Immulon 2HB 96-well plates (DYNEX Technologies, Inc.). For each library, two wells were coated with caprylate-bound HSA (10 μg/ml at 100 μl/well) in PBS at 4° C. overnight. The next day, HSA was removed and these wells were then blocked with PBS/0.1% caprylate/0.1% TWEEN-20® nonionic detergent (PBSCT) for two hours at room temperature. The wells were washed in PBSCT six times. Next, each phage library was diluted in PBSCT to $10^9$ pfu/μl. An aliquot (100 μl) of a given diluted phage library was added to each HSA-coated well, so that there were $10^{11}$ total phage per well. Phage were incubated in the wells at room temperature for 2 hours and then washed six times with PBSCT. Bound phage were eluted by adding to each well 100 μl of CBS (50 mM sodium citrate, 150 mM sodium chloride, pH 2) for 5 minutes. The eluted phage in the wells were then neutralized with 250 μl of 2 M Tris, pH 8. All wells were pooled for a 1.5 ml total volume. Pooled phage were mixed with XL1-Blue MRF' *Esherichia coli* cells, which had been chilled on ice after growing to mid-logarithmic phase. The phage-infected cells were then plated out onto a large square plate (243 mm×243 mm×18 mm NUNC Bio-Assay plates containing NZCYM agar supplemented with 100 μg/ml ampicillin) at a density of about $1×10^4$ colonies/plate and grown overnight at 37° C. Colonies were picked robotically (BioRobotics BioPick, Cambridge, UK) into 96-well flat-bottom plates (Greiner Labortechnik, Germany) containing 100 μl/well of TE buffer (pH 8.5). From these plates, ten 96-well overnight culture plates for ELISA work were prepared.

Enzyme Linked Inmunosorbent Assay (ELISA)

For analysis of caprylate-HSA as a target, Immulon 2HB plates were prepared by the addition of 340 μl/well of caprylate-HSA at 5.6 μg/ml. The plates were incubated overnight at 4° C. The HSA-coated plates were then washed robotically with PBSCT six times (BioTek 404, BioTek Instruments). To account for plate binders, empty plates were also washed. An equal volume of each phage clone isolate was added to a plate well containing 70 µl PBSCT in both the target plate and the control plate. Plates were incubated for one hour at room temperature. The plates were washed seven times with PBSCT using the BioTek 404 apparatus. A 1:10,000 dilution of Pharmacia HRP-αM13 antibody conjugate in PBSCT was added to each well, at 100 µl/well. Plates were incubated for one hour. After incubation, plates were washed six times with PBSCT using the BioTek 404 apparatus. Following the wash, 100 µl of a 1:1 solution of the two-component TMB substrate solution was added to each well, and the plates incubated for 30 minutes. The plates were then read at 620 nm with an automatic BioTek plate reader.

HSA Selection and ELISA Protocols for Soluble Capture Screening

TN6/6 and TN12/1 phage libraries were screened against caprylate-biotinylated-HSA in solution. For this procedure, Level 1 Sera-Mag streptavidin magnetic beads(Seradyn, Indianapolis, Ind.) were washed five times in PBSCT. The phage were first processed to remove phage that would bind directly to the streptavidin coated magnetic beads in the absence of caprylate-biotinylated HSA. Approximately $3-4 \times 10^{11}$ plaque forming units (pfu) from a library per 100 µl of PBSCT were introduced to an aliquot (100 µl) of PBSCT-washed beads in a microfuge tube. The beads were then kept suspended by placing the microfuge tube containing the bead-phage mixture on a Labquake shaker (Labindustries, Berkeley, Calif.). After 10 minutes, the beads were pelleted at 14,000×g, and the supernatant liquid containing phage was transferred to a fresh tube containing another aliquot of PBSCT washed beads. A total of five such 10 minute exposures of phage to aliquots of beads were used.

The processed phage solution (100 µl) was made 1 µM in caprylate-biotinylated-HSA by the addition of 2 µl of a stock solution of biotinylated HSA. After 1 hour, the mixture was added to an aliquot (100 µl) of Level 5 Sera-Mag streptavidin magnetic beads, which had previously been washed five times with PBSCT. The tube was placed on a Labquake shaker for five minutes to allow capture of caprylate-biotinylated-HSA phage complex onto the beads. Caprylate-biotinylated-HSA is captured on the beads as well. Beads were then washed as rapidly as possible with 5×1 ml PBSCT+0.1 mM biotin using a magnetic stand (Promega, Madison, Wis.) to separate the beads from the PBCT+0.1 mM biotin, which was discarded. Phage that remained bound to the beads after the washing were eluted with 2×250 µl aliquots of PBS, pH 2, over the course of 15 minutes. The eluates containing phage were neutralized with 100 µl of 2 M Tris, pH 8. Eluates were mixed with aliquots of XL1-Blue MRF' E. coli cells, which had been chilled on ice after growing to mid-logarithmic phase. After approximately 15 minutes at room temperature, a phage/cell mixture was spread onto a Bio-Assay Dish (243 mm×243 mm×18 mm, Nalge Nunc) containing 250 ml of NZCYM agar supplemented with 50 µg/ml of ampicillin. The plate was incubated overnight at 37° C. The next day, phage were harvested from the plate.

Binding to caprylate-HSA was assayed for the selected phage using ELISA basically as describe above, except that wells of the multi-well assay plates were first coated with streptavidin and then caprylate-biotinylated-HSA was added to immobilize HSA on the surface of the wells. Control wells were only coated with streptavidin with no added caprylate-biotinylated-HSA.

DNA Sequencing

DNA from isolated phage displaying a peptide of interest were isolated and sequenced using a commercially available kit for polymerase chain reaction (PCR) sequencing of M13 phage (TWO BIG DYE™, Applied Biosystems, Foster City, Calif.). Briefly, overnight phage cultures were diluted 100-fold with distilled water and amplified by PCR using 3PCRUP and 3PCRDN primers. The amplified products were then diluted 1:20 with twice distilled water, and 3 µg aliquots of the PCR amplified nucleic acid products were sequenced basically following the manufacturer's suggested procedure. The sequence reactions were set up in 10 µl volumes using the PCRB3DN and 3Seq-80 primer molecules. The sequencing reaction products were run on an automated Applied Biosystems 3700 fluorescence sequencing machine and sequence data collected.

Peptide Synthesis and Fluorescein Labeling

Once phage isolate DNA sequences were determined, corresponding peptides were commercially synthesized by solid phase synthesis using standard 9-fluorenylmethoxycarbonyl (FMOC) protocols (Bachem Bioscience, King of Prussia, Pa.) and were purified by reverse-phase chromatography. Masses were confirmed by electrospray mass spectrometry, and peptides were quantified by ultraviolet absorbance at 280 nm. Unvaried phage-derived amino acid sequences Ala-Glu-Gly-Thr-Gly-Ser (amino acids 1–6 of SEQ ID NO: 3) and Asp (or Ala)-Pro-Glu flanking each selected amino acid sequence were retained, and the synthesized polypeptides were N-terminally acetylated. A C-terminal group was added to each polypeptide, i.e., either a -Gly-Gly-Gly-Lys-NH$_2$ (SEQ ID NO: 24) linker or a (6-aminohexanoic acid)-Lys-NH$_2$ carboxy terminal capping group. For those selected peptides with internal lysine residues, the internal lysine was protected with 1-(4,4-dimethyl-2,6-dioxocyclohex-1-ylidene)-3-methylbutyl (ivDde) (Chan, Tetrahedron Lett., 39: 1603–1606 (1998)). This protecting group allows selective coupling on the C-terminal lysine, is not removed during peptide cleavage, and can be removed after derivatization on the C-terminal lysine using 2% hydrazine in dimethylformamide (DMF) or 0.5 M hydroxylamine, pH 8.

Fluorescence Anisotropy Measurements

Affinity determinations were made by first labeling polypeptides on the C-terminal end with NHS-fluorescein. Fluorescence anisotropy measurements were performed in 384-well microplates in a volume of 10 µl in binding buffer using a Tecan Polarion fluorescence polarization plate reader. The concentration of fluorescein labeled peptide was held constant (20 nM), and the concentration of HSA was varied. For pH 6.2, 7.1, and 7.4 binding conditions, a 3 mM phosphate, 0.01% TWEEN-20® buffer was used. For pH 9.1 binding conditions, a 3 mM sodium bicarbonate buffer, 0.01% TWEEN-20® nonionic detergent buffer was used. Once NaCl was added to any of these buffers, their pH was adjusted again to achieve the original pH. The binding mixtures were equilibrated for 10 minutes in the microplate at 300° C. prior to performing the measurement. The observed change in anisotropy was fit to the equation below via nonlinear regression to obtain the apparent $K_D$. This equation assumes that the peptide and HSA form a reversible complex with 1:1 stoichiometry.

$$r_{obs} = r_{free} + (r_{bound} - r_{free}) \frac{(K_D + HSA + P) - \sqrt{(K_D + HSA + P)^2 - 4 \cdot HSA \cdot P}}{2 \cdot P}$$

where $r_{obs}$ is the observed anisotropy, $r_{free}$ is the anisotropy of the free peptide, $r_{bound}$ is the anisotropy of the bound peptide, $K_D$ is the apparent dissociation constant, HSA is the total HSA concentration, and P is the total fluorescein-labeled peptide concentration.

Peptide Mobilization on NZHS-SEPHAROSE® Resin

For producing immobilized peptide test columns, 5 micromoles of each peptide were dissolved in DMSO in a minimal volume and then added to 1 ml of NHS-SEPHAROSE® affinity chromatography resin (Amersham Pharmacia Biotech, Piscataway, N.J.), which had been washed once with dimethyl sulfoxide (DMSO). The immobilization reaction was initiated by the addition of diisopropylethylamine to 2% (vol/vol). After 4 hours of slow mixing on a shaker table at room temperature, the reaction was quenched by the addition of an equal volume of 0.5 M hydroxylamine, pH 8, in water. For those peptides with ivDde-protected internal lysines, the hydroxylamine quench treatment also removed the ivDde-protecting group. To allow for complete protecting group removal, the quenched reaction was allowed to incubate overnight at room temperature. Once quenched and deprotected, the immobilized peptide-SEPHAROSE® resin was washed at least 3 times with water to remove solvent and unbound peptide. Non-specifically bound peptide was eluted off the resin by washing the resin at least three times in 30 mM phosphoric acid, pH 2. Since the NHS-SEPHAROSE® resin surface becomes negatively charged after hydrolysis, an acidic wash neutralizes the surface and removes any peptides bound non-covalently to the surface via electrostatic interactions. After washing, the resin was resuspended in water as a 50% v/v mixture. A 50 .mu.g aliquot was used to determine the ligand density on the resin by quantitative amino acid analysis. Finally, the resin slurry was packed into 0.35 ml OMNIFIT™ glass columns (3 mm.times.50 mm) for analytical testing.

For larger preparative columns, the amounts of peptide and SEPHAROSE® were scaled up proportionally, and the final peptide SEPHAROSE® batches were packed into larger 10 ml Omnifit columns (10 mm diameter).

HSA Column Testing

For analytical affinity column testing, albumin was dissolved at 1 mg/ml concentration in 3 mM sodium phosphate, pH 6.2, 0.0 1% TWEEN-20® non-ionic detergent (equilibration buffer). One milliliter of albumin solution was passed through each column (0.35 ml) previously equilibrated in equilibration buffer. The columns were washed with the same equilibration buffer and then eluted with 100mM Tris, pH 9.1 (flowrate, 0.5 ml/min for all steps). The column chromatography was carried out using a BIO-RAD BIOLOGIC.TM. monitoring system (Hercules, Calif.) throughout this testing with absorbance monitoring at 280 nm.

For preparative DX-236-SEPHAROSE® affinity column (10 ml) testing, human serum was dialyzed against 3 mM phosphate, pH 6.2, 20 mM NaCl, 0.01% TWEEN-20® non-ionic detergent (equilibration buffer). One hundred microliters (100 .mu.l) of dialyzed serum were injected onto the preparative DX-236-SEPHAROSE® chromatography column, which was previously equilibrated with buffer. The column was washed with the same buffer, followed by a gradient between 20 and 44 mM NaCl, and finally the HSA was eluted with 100 mM Tris, pH 9.1. For all steps, the flowrates were 5 ml/min.

For Cibacron Blue SEPHAROSE® affinity chromatography testing (Amersham Pharmacia Biotech, Inc., Piscataway, N.J.), human serum was dialyzed into PBS, pH 7, 0.01% TWEEN-20® non-ionic detergent (equilibration buffer). One hundred microliters (100 .mu.l) of dialyzed serum was injected on a 1 ml Cibacron Blue SEPHAROSE® column, which was previously equilibrated with equilibration buffer. The column was washed with the same equilibration buffer and then HSA was eluted with PBS, 1 M NaCl, pH 7. For all steps, the flowrates were 1 ml/minute.

Isolation of HSA Binding Peptides

Selection of HSA binding polypeptides from a series of phage display libraries was performed using immobilized HSA targets. Both passive immobilization on polystyrene plates and active immobilization using biotinylated albumin target on streptavidin beads or plates were used in the selections. Once the libraries were selected against the target in multiple rounds, single phage isolates were picked from plates and assayed for target binding in ELISA format. The ELISA positive isolates were sequenced, and corresponding synthetic peptides were prepared for affinity determination using fluorescence anisotropy. Those peptides that bound well to HSA were immobilized on SEPHAROSE® chromatography resin and tested for HSA binding.

In the first phage library selection, a pool of phage libraries displaying peptides of various sizes were incubated against passively immobilized HSA on polystyrene microtiter plates. This pool consisted of an equal mixture of three phage libraries (TN6/6, TN10/9, and TN12/1) displaying variegated peptides having cyclic segments of six, ten and twelve amino acids, respectively.

The TN6/6 library was constructed to display a single microprotein binding loop contained in a 12-amino acid template. The TN6/6 library utilized a template sequence of $Xaa_1$-$Xaa_2$-$Xaa_3$-Cys-$Xaa_5$-$Xaa_6$-$Xaa_7$-$Xaa_8$-Cys-$Xaa_{10}$-$Xaa_{11}$-$Xaa_{12}$ (SEQ ID NO: 237). The amino acids at positions 2, 3, 5, 6, 7, 8, 10, and 11 of the template were varied to permit any amino acid except cysteine (Cys). The amino acids at positions 1 and 12 of the template were varied to permit any amino acid except cysteine (Cys), glutamic acid (Glu), isoleucine (Ile), Lysine (Lys), methionine (Met), and threonine (Thr).

The TN10/9 library was constructed to display a single microprotein binding loop contained in a 16-amino acid template. The TN10/9 library utilized a template sequence $Xaa_1$-$Xaa_2$-$Xaa_3$-Cys-$Xaa_5$-$Xaa_6$-$Xaa_7$-$Xaa_8$-$Xaa_9$-$Xaa_{10}$-$Xaa_{11}$-$Xaa_{12}$-Cys-$Xaa_{14}$-$Xaa_{15}$-$Xaa_{16}$ (SEQ ID NO: 238). The amino acids at positions 1, 2, 15, and 16 in the template were varied to permit any amino acid selected from a group of 10 amino acids: D, F, H, L, N, P, R, S, W, or Y). The amino acids at positions 3 and 14 in the template were varied to permit any amino acid selected from a group of 14 amino acids: A, D, F, G, H, L, N, P, Q, R, S, V, W, or Y). The amino acids at positions 5, 6, 7, 8, 9, 10, 11, and 12 in the template were varied to permit any amino acid except cysteine (Cys).

The TN12/1 library was constructed to display a single microprotein binding loop contained in an 18-amino acid template. The TN12/1 library utilized a template sequence $Xaa_1$-$Xaa_2$-$Xaa_3$-Cys-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-Cys-$Xaa_{16}$-$Xaa_{17}$-$Xaa_{18}$ (SEQ ID NO: 42). The amino acids at position 1, 2, 17, and 18 in the template were varied to permit any amino acid selected from a group of 12 amino acids: A, D, F, G, H, L, N, P, R, S, W, or Y). The amino acids at positions 3, 5, 6, 7, 8, 9, 10, 11, 12, 13, 14, and 16 were varied to permit any amino acid except cysteine (Cys).

The phage display libraries were created by making a designed series of mutations or variations within a coding sequence for the polypeptide template, each mutant sequence encoding a peptide analogue corresponding in overall structure to the template except having one or more amino acid variations in the sequence of the template. The novel variegated (mutated) DNA provides sequence diversity, and each transformant phage displays one variant of the initial template amino acid sequence encoded by the DNA, leading to a phage population (library) displaying a vast number of different but structurally related amino acid sequences.

Phage libraries were incubated with HSA in PBS, 0.1% sodium caprylate, 0.1% TWEEN-20® detergent, pH 7.4. Caprylate is known to stabilize HSA against temperature-induced denaturation and proteolytic digestion, most likely by promoting a tightening of the C-terminal domain. Consequently, sodium caprylate was added to the incubation buffer to drive the structure into a more homogenous population (Arakawa et al., *Biochim. Biophys. Acta*, 1479: 32–36 (2000); Ross et al., *Vox Sang,* 47: 19–27 (1984); Shrake et al., *Vox Sang,* 47: 7–18 (1984)). FDA-approved HSA preparations, sodium caprylate and/or sodium acetyl-L-tryptophanate are often added just prior to pasteurization to stabilize the preparation. Sodium caprylate also promotes release of HSA-bound metabolites from serum-purified albumin (Cheruvallath et al., *Pharm. Res.,* 13: 173–178 (1996); Kragh-Hansen, *Biochem. J,* 273: 641–644 (1991)). An affinity column that was not inhibited by sodium caprylate would enable its addition prior to purification for enhanced stabilization against proteases and heat-induced denaturation.

The first selection resulted in several phage isolates that showed positive HSA binding by ELISA (see,e.g., FIG. 1). Sequencing of the display polypeptides from the first round of phage isolates revealed the following HSA binding polypeptides:

VAWCTIFLCLDV (SEQ ID NO: 239)
FKICDQWFCLMP (SEQ ID NO: 240)
HVGCNNALCMQY (SEQ ID NO: 241)
WKVCDHFFCLSP (SEQ ID NO: 242)
NHGCWHFSCIWD (SEQ ID NO: 243)
FRNCEPWMLRFGCNPR (SEQ ID NO: 244)
ADFCEGKDMIDWVYCRLY (SEQ ID NO: 245)
FWFCDRIAWYPQHLCEFLD (SEQ ID NO: 246)
DWDCVTRWANRDQQCWGP (SEQ ID NO: 247)
DWDCVTRWANRDQQCWAL (SEQ ID NO: 248)
DWDCVTDWANRHOHCWAL (SEQ ID NO: 249)
DWQCVKDWANRRRGCMAD (SEQ ID NO: 250)
RNMCKFSWIRSPAFCARADP (SEQ ID NO: 251)

In the foregoing amin acid sequences, the putative disulfide-constrained cyclic peptide, which identifies the library from which the isolates were selected, is underscored.

From the ELISA -type assays, phage isolate 232 showed the highest ELISA signal (see FIG. 1). The polypeptides from the phage isolates were synthesized as described above for further testing and determination of a dissociation constant ($K_D$) for HSA under various conditions. The binding data and the sequences of the synthetic polypeptides are shown in Table 1, below.

TABLE 1

Dissociation Constants (µM) of HSA Binding Peptides Under Various Conditions

| | | pH | | | | | |
|---|---|---|---|---|---|---|---|
| | | 6.2 | 6.2 | 7.1 | 7.4 | 7.4 | 9.1 |
| | | | | NaCl (±0.14 M) | | | |
| | | − | + | − | + | + | + |
| | | | | Caprylate (±0.1%) | | | |
| Peptide | Sequence | − | − | − | − | + | − |
| DX-232 | Ac-AEGTGSVAWCTIFLCLDVAPEGGGK—NH₂ (SEQ ID NO:25) | 0.22 | 0.5 | N.A. | 0.18 | 1.05 | N.A. |
| DX-295 | Ac-AEGTGSFKICDQWFCLMPAPE-X-K—NH₂ (SEQ ID NO:26) | 1.8 | >100 | N.A. | 86 | 210 | N.A. |
| DX-296 | Ac-AEGTGSHVGCNNALCMQYAPE-X-K—NH₂ (SEQ ID NO:27) | 17 | >100 | N.A. | 76 | >200 | N.A. |
| DX-297 | Ac-AEGTGSWKVCDHFFCLSPAPE-X-K—NH₂ (SEQ ID NO:28) | 18 | >200 | N.A. | >200 | >200 | N.A. |
| DX-298 | Ac-AEGTGSNHGCWHFSCIWDAPE-X-K—NH₂ (SEQ ID NO:29) | 1.9 | >200 | 22 | 127 | 73 | >200 |
| DX-238 | Ac-AEGTGSFRNCEPWMLRFGCNPRAPE-GGGK—NH₂ (SEQ ID NO:30) | 4.8 | 61 | N.A. | 79 | 110 | N.A. |
| DX-234 | Ac-AEGTGDADFCEGKDMIDWVYCRLY-DPEGGGK—NH₂ (SEQ ID NO:31) | 2.5 | 85 | N.A. | 109 | 118 | N.A. |
| DX-236 | Ac-AEGTGDFWFCDRIAWYPQHLCEFL-DPEGGGK—NH₂ (SEQ ID NO:32) | 1.9 | 8.7 | 5.6 | 11 | 26.8 | 99 |
| DX-313 | Ac-AEGTGDDWDCVTRWANRDQQCWG-PDPE-X-K—NH₂ (SEQ ID NO:33) | 9.5 | 80 | 37 | >200 | 121 | 90 |

TABLE 1-continued

Dissociation Constants (μM) of HSA Binding Peptides Under Various Conditions

| | | pH | | | | | |
|---|---|---|---|---|---|---|---|
| | | 6.2 | 6.2 | 7.1 | 7.4 | 7.4 | 9.1 |
| | | | | NaCl (±0.14 M) | | | |
| | | − | + | − | + | + | + |
| | | | | Caprylate (±0.1%) | | | |
| Peptide | Sequence | − | − | − | − | + | − |
| DX-315 | Ac-AEGTGDDWDCVTRWANRDQQCWA-LDPE-X-K—NH$_2$ (SEQ ID NO:34) | 13 | >200 | N.A. | 113 | >100 | N.A. |
| DX-317 | Ac-AEGTGDDWDCVTDWANRHQHCWA-LDPE-X-K—NH$_2$ (SEQ ID NO:35) | 6.7 | >200 | N.A. | 74 | 45 | N.A. |
| DX-319 | Ac-AEGTGDDWQCVKDWANRRRGCMA-DDPE-X-K—NH$_2$ (SEQ ID NO:36) | 17 | >200 | N.A. | >200 | 26 | N.A. |
| DX-321 | Ac-AEGTGDRNMCKFSWIRSPAFCARA-DPE-X-K—NH$_2$ (SEQ ID NO:37) | 0.9 | 9 | N.A. | 84 | 75 | N.A. |
| | Fluorescein | 30 | >200 | N.A. | >200 | >200 | N.A. |
| Cyt | X-GAQGHTVEK—NH$_2$ (SEQ ID NO:38) | 335 | N.A. | N.A. | N.A. | N.A. | N.A. |

-X- = 6-aminohexanoic acid;
K or X (in bold) = site of fluorescein label;
—NH$_2$ = C-terminal amide;
N.A. = not assayed.

Figure 2:
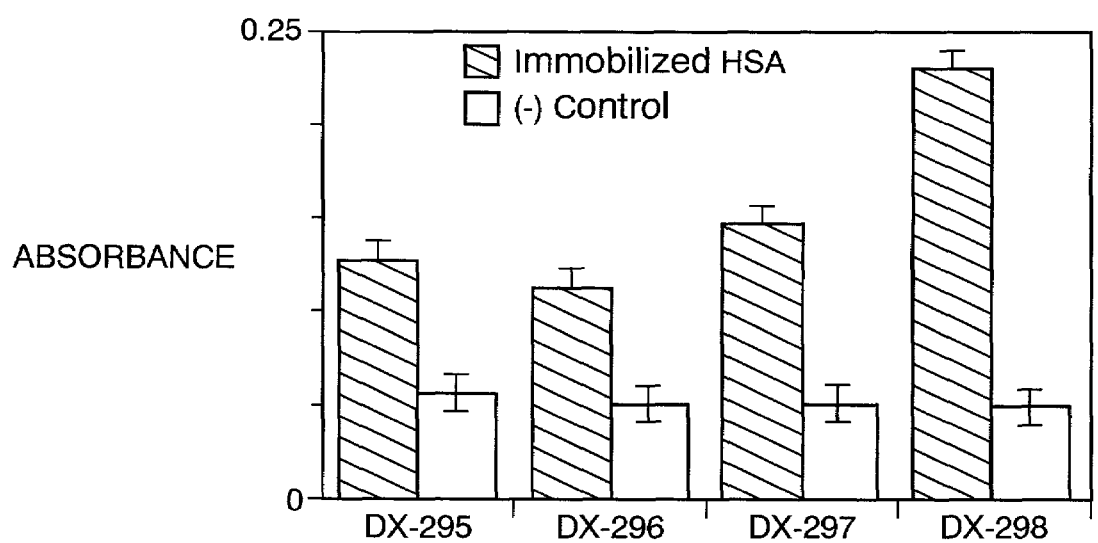
FIG. 2 shows binding (absorbance at 620 nm) to human serum albumin (HSA) by phage isolates displaying binding peptides DX-295, DX-296, DX-297, and DX-298 in an enzyme linked immunosorbent assay (ELISA ). Phage were selected from a TN6/6 phage library as described below. Phage were tested for ability to bind HSA in an ELISA format using caprylate biotinylated HSA, which had been immobilized on streptavidin coated wells of a microtiter assay plate. Binding of phage to immobilized HSA was as in FIG. 1 with HRP-conjugated anti-M13 antibody. Following addition of TMB substrate, the absorbance at 620 nm was read with an automated plate reader. Phage bound to HSA is shown by diagonal striped bars; control wells (streptavidin-coated wells only, no HSA) is shown by open bars.
Figure 3:
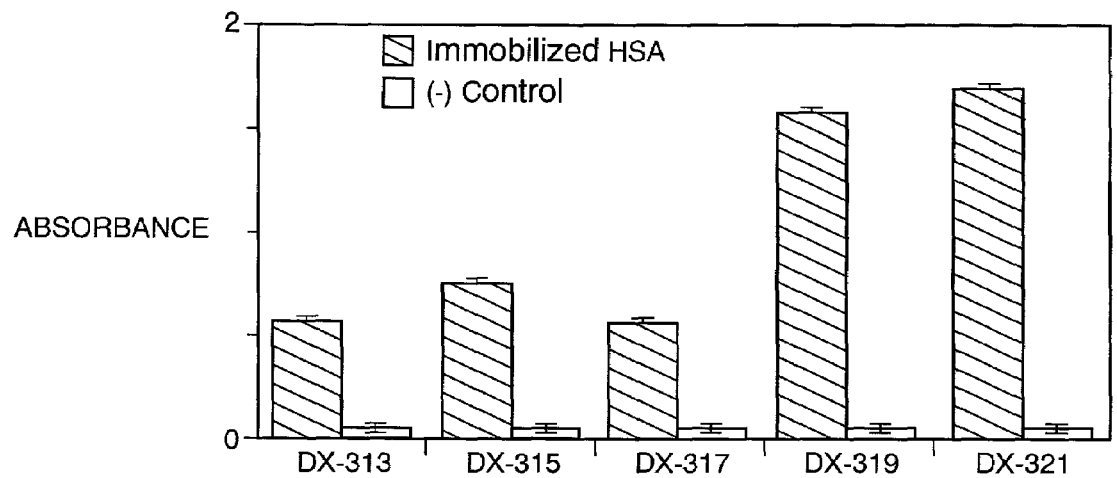
FIG. 3 shows binding (absorbance at 620 nm) to human serum albumin (HSA) by phage isolates displaying binding peptides DX-313, DX-315, DX-317, DX-319, and DX-321 in an enzyme-linked immunosorbent assay (ELISA). Phage were selected from a TN12/1 phage library as described in the text. Phage were tested for ability to bind HSA as described for FIG. 2. Phage bound to HSA is shown by diagonal striped bars; control wells (streptavidin-coated wells only, no HSA added) is shown by open bars.

Since passively adsorbed protein selections sometimes select for phage binders to protein conformers only present when bound to plastic (Norde et al., *J. Biotechnol.*, 79: 259–268 (2000)), another selection was conducted using biotinylated HSA (bioHSA) and magnetic streptavidin beads. In particular, proteins that change conformation as a function of their environment (pH, salt, temperature), e.g., HSA, are often found to adopt different conformations when immobilized on a plastic surface. In this selection, bioHSA was allowed to incubate with the phage library in solution for one hour prior to capturing HSA binding phage by the addition of magnetic streptavidin beads for 15 minutes. As in the previous selection, all incubations were done in PBS, 0.1% sodium caprylate, and 0.1% TWEEN-20® detergent. Unlike in the first selection, however, the libraries were not pooled and the TN6/6 and TN12/1 libraries were selected separately using this solution phase capture protocol. From each of these selections, several positive isolates were identified from ELISA work (FIGS. 2 and 3, Table 1). From the TN6/6 screen, phage 298 showed the highest ELISA binding signal; whereas in the TN12/1 screen, phage 321 showed the highest signal.

Once all the positive phage isolates were sequenced, peptides corresponding to the display peptide were synthesized. A small amount of constant phage sequence surrounding each varied amino acid sequence region was retained and either a -GGGK-NH$_2$ (SEQ ID NO: 24) amino acid sequence or —X—K—NH$_2$ C-terminal tail was added to each peptide, where X is 6-aminohexanoic acid and K-NH$_2$ is an amidated terminal lysine residue. The constant phage sequence was retained because these residues can often play a role in target binding. To determine its affinity for HSA, each peptide was labeled with fluorescein on the C-terminal lysine side chain. Using fluorescence anisotropy, the affinity of each peptide was determined in PBS, 0.1% sodium caprylate, 0.01% TWEEN-20® detergent. As shown in Table 1, only DX-232 had a K$_D$ below 10 μM under these conditions. Most of the peptides also did not show a dramatic dependence on caprylate for binding in PBS. Since most of the peptide affinities for HSA in the screening buffer (with or without caprylate) were lower than expected, the HSA binding of each peptide was evaluated over a range of pH, salt concentration (0.14 M NaCl), and ±1% caprylate. Many of the peptides bound better at lower pH (e.g., 3 mM phosphate, pH 6.2) and in the absence of salt (e.g., buffer only with no added NaCl) (Table 1). Others have observed that HSA undergoes dramatic structural changes under differing pH conditions (Luik et al., *Spectrochim. Acta A Mol. Biomol. Spectrosc.*, 54A: 1503–1507 (1998)). Since HSA also bound free fluorescein in this same buffer with a K$_{D\ of}$ 30 μM, this was used as a practical standard to differentiate between binders specific for HSA and binders considered too non-specific for the purposes of the experiment.

Figure 4:
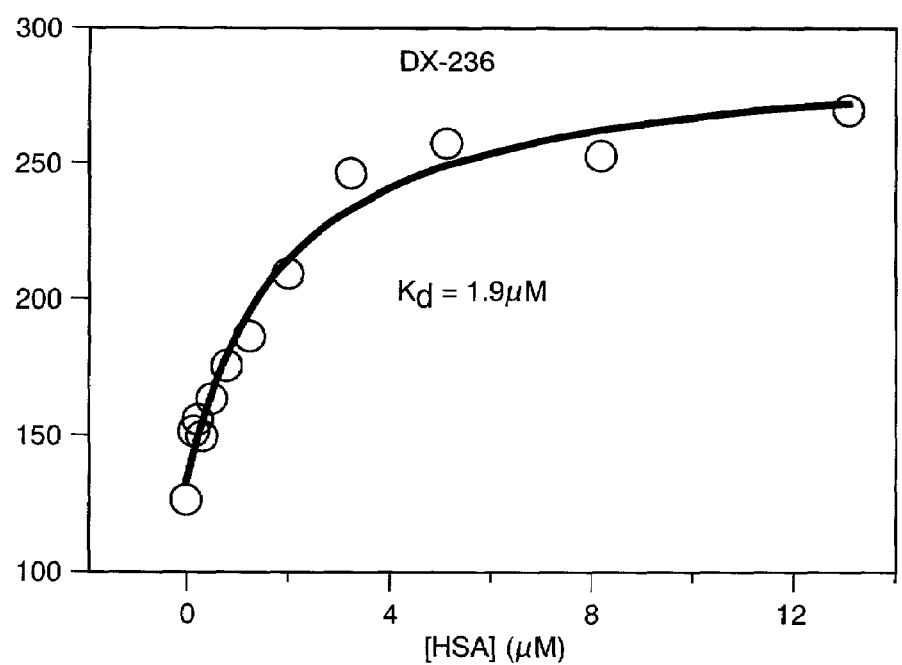
FIG. 4 shows a graph of fluorescence anisotropy (y-axis) for direct HSA binding by fluorescein-labeled HSA binding polypeptide DX-236 as a function of HSA concentration ([HSA] in μM) at pH 6.2, no NaCl.
Figure 5:
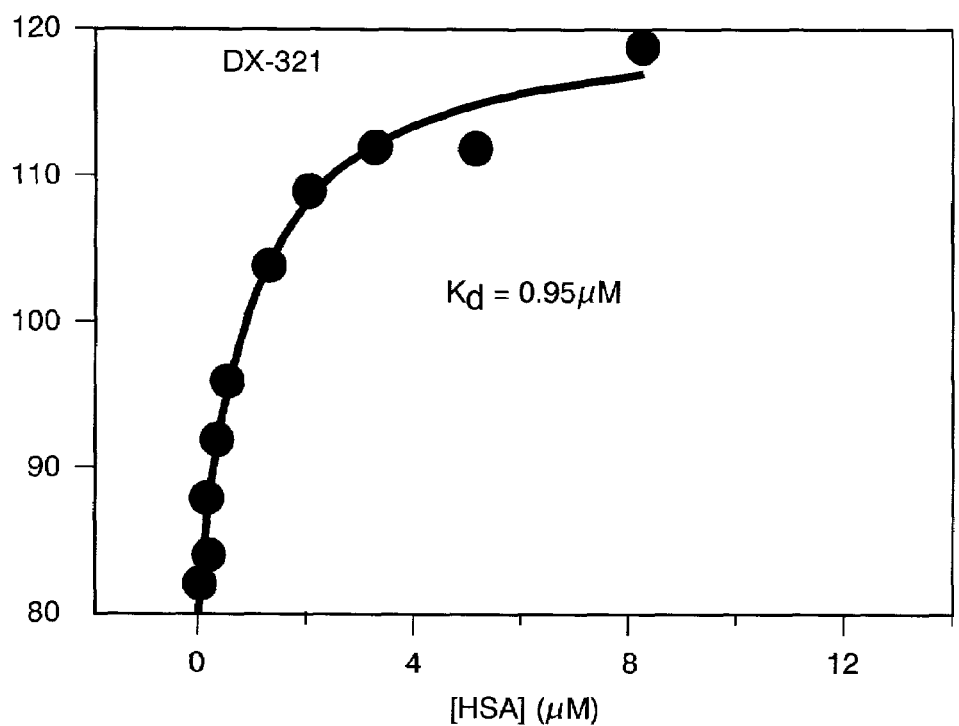
FIG. 5 shows a graph of fluorescence anisotropy (y-axis) for direct HSA binding by fluorescein-labeled HSA binding polypeptide DX-321 as a function of HSA concentration ([HSA] in μM) at pH 6.2, no NaCl.
Figure 6:
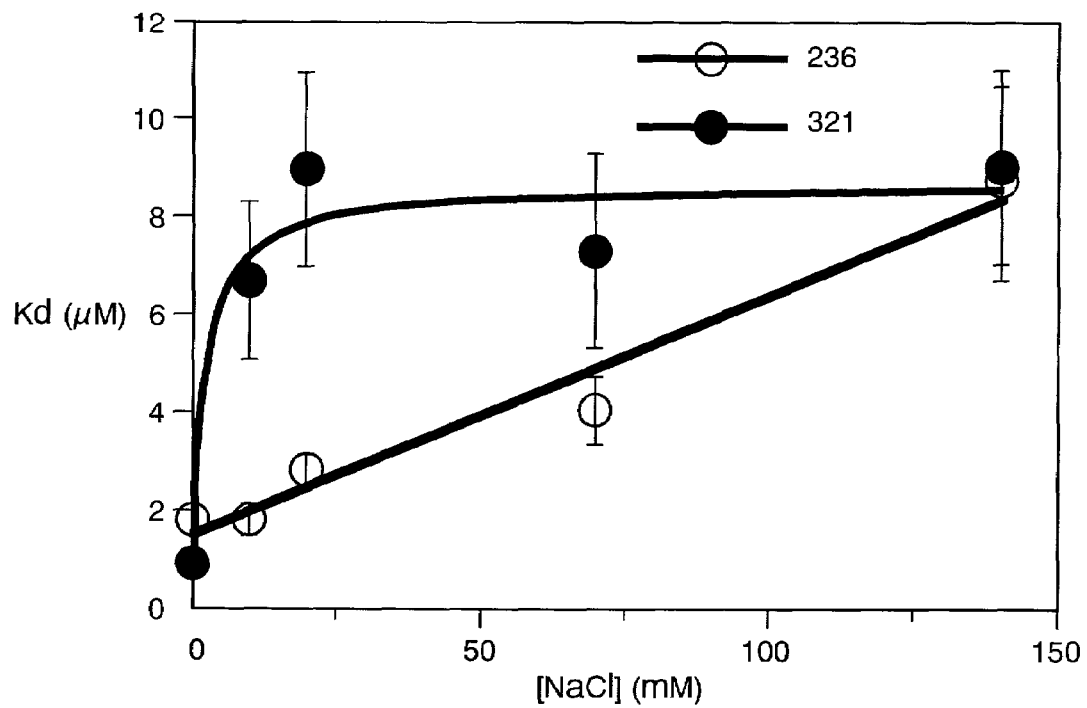
FIG. 6 shows a graph of dissociation constant ($K_D$) calculated from fluorescence anisotropy as a function of concentration of NaCl for DX-236 (open data points) and for DX-321 (solid data points).

It is evident from the data presented in Table 1 that at pH 6.2 peptide affinity for HSA decreases as the salt concentration is increased to 0.14 M. DX-232, DX-236 and DX-321 were the only peptides that had K$_D$ values of less than 5 μM at pH 6.2 in the absence of salt that did not show greater than a 10-fold increase in K$_D$ as the salt concentration was increased to 140 mM (Table 1). Graphs of the anisotropy measurements for HSA binding by DX-236 and DX-321 at pH 6.2 in the absence of salt are shown in FIGS. 4 and 5, respectively. Closer inspection revealed that the DX-236 K$_D$ increased linearly from about 1.9 to about 8.7 μM upon titrating up to 140 mM NaCl (see, open data points in FIG. 6). In contrast, the DX-321 K$_D$ increased sharply from about 0.9 to about 9 μM upon adding 10 mM NaCl (see, solid data points in FIG. 6). Since DX-236 does not show such a dramatic sensitivity to salt, some additional salt could be added during chromatographic steps to reduce non-specific binding of other proteins.

Besides investigating the salt and pH dependence of HSA binding by the DX-236 peptide, truncated variants of the peptide were synthesized to determine the minimal HSA binding site in the DX-236 peptide. Results are summarized in Table 2.

TABLE 2

K_D for Truncated Peptides of DX-236

| Polypeptide | $K_D$ (μM) | SEQ ID NO. |
|---|---|---|
| Ac-AEGTGDFWF<u>CDRIAWYPQHLC</u>EFLDPEGGGK—NH$_2$ | 1.9 | 19 |
| Ac-FWF<u>CDRIAWYPQHLC</u>EFLDPEGGGK—NH$_2$ | 8.9 | 39 |
| Ac-<u>CDRIAWYPQHLC</u>EFLDPEGGGK—NH$_2$ | 8.7 | 40 |
| Ac-AEGTGDPWF<u>CDRIAWYPQHLC</u>EFLGGGK—NH$_2$ | 9.9 | 41 |
| Ac-AEGTGDFWF<u>CDRIAWYPQHLC</u>GGGK—NH$_2$ | 8.9 | 42 |
| Ac-<u>CDRIAWYPQHLC</u>GGGK—NH$_2$ | 16.0 | 43 |
| Ac-DRIAWYPQHLGGGK—NH$_2$ | 125 | 44 |

From the analysis (Table 2), it appeared that the presence of C-terminal and N-terminal flanking sequences improves the affinity of the binding peptide for an HSA target. Truncation of the C- or N-terminal amino acids alone resulted in an approximately 4-fold increase in the $K_D$ (see, SEQ ID NOS: 39–42 in Table 2). Truncation of both C- and N-termini resulted in an 8-fold increase in the $K_D$ (Cf. SEQ ID NO: 19 and SEQ ID NO: 43 in Table 2). The core sequence without the flanking cysteines (SEQ ID NO: 44) showed the lowest binding affinity ($K_D$ 125 μM). These data are consistent with the idea that a constrained structure allows binding to HSA with high affinity.

Based on the $K_D$ measurements (Table 1), DX-232, DX-236, and DX-321 binding peptides were pursued for affinity chromatography development. Each peptide was immobilized at high density on NHS-SEPHAROSE® resin using the procedure outlined above. The peptides were immobilized via the same C-terminal lysine used for fluorescein labeling in fluorescence anisotropy measurements. As determined by quantitative amino acid analysis, the ligand densities for DX-321-SEPHAROSE®, DX-236-SEPHAROSE®, and DX-232-SEPHAROSE® columns were 3.2, 0.8, and 2.4 μmol!ml, respectively. Each column was tested for HSA binding (1 mg injection) in binding buffer--3 mM sodium phosphate, 0.1% TWEEN-20® detergent, pH 6.2. Since some of the peptides showed a sharp increase in $K_D$ as the pH was increased to 9.1 (Table 1), it was speculated that a 100 mM Tris, pH 9.1 buffer would elute HSA effectively from these columns.

Each column performed differently in the initial HSA binding tests. Although soluble peptide DX-232 bound HSA with the highest affinity, immobilized DX-232 on a SEPHAROSE® column captured no detectable HSA. DX-236-SEPHAROSE®, on the other hand, was the best performer and quantitatively bound the entire 1mg injection (total capacity ≧2.7 mg/ml) (see, Table 3, below).

TABLE 3

Analysis of HSA Affinity Columns

| Peptide in Affinity Column | Fraction | μg HSA | % Initial Load | Total Capacity |
|---|---|---|---|---|
| DX-321 | Flow through | 554 | 55.4 | |
|  | Elution | 370 | 37.0 | >1.1 mg/ml |
| DX-236 | Flow through | 0 | 0 | |
|  | Elution | 947 | 94.7 | ≧2.7 mg/ml |

At higher HSA loads, the same DX-236 column was capable of binding at least 4 mg HSA, which corresponds to a total capacity of greater than 11 mg/ml (data not shown). DX-321-SEPHAROSE® was an intermediate performer and bound a fraction of the total material (total capacity >1.1 mg/ml). The Tris elution buffer eluted all of the bound HSA from both DX-236- and DX-321-SEPHAROSE® columns.

Species Specificity of Isolated HSA Binders

To test the binding specificity of DX-236 and DX-321 for HSA over other albumins, their dissociation constants ($K_D$) were determined against a panel of mammalian albumins both in 3 mM sodium phosphate, pH 6.2, and in PBS (10 mM sodium phosphate, 140 mM NaCl, pH 7.4). The results are set forth in Table 4.

TABLE 4

Species Specificity Data for Affinity Columns

| Species | pI | % Identity to Human | DX-236 phosphate, pH 6.2, 0 M NaCl $K_D$ (μM) | DX-236 PBS, pH 7.4, 0.14 M NaCl $K_D$ (μM) | DX-321 phosphate, pH 6.2, 0 M NaCl $K_D$ (μM) | DX-321 PBS, pH 7.4, 0.14 M NaCl $K_D$ (μM) |
|---|---|---|---|---|---|---|
| Human | 5.67 | 100 | 1.9 | 11.0 | 0.9 | 84 |
| Rhesus | 5.67 | 93.2 | 1.1 | 23 | 38 | 82 |
| Bovine | 5.60 | 75.6 | 1.1 | 13.3 | 21 | >200 |
| Goat | N.D. | N.D. | 1.6 | 23 | 95 | 83 |
| Pig | 5.75 | 75.0 | 0.5 | 12 | 21 | >200 |
| Rabbit | 5.65 | 75.0 | 0.5 | 18 | 32 | >200 |
| Rat | 5.80 | 73.2 | 1.6 | 25 | 23 | 117 |
| Mouse | 5.53 | 72.0 | 5.5 | 32 | >200 | >200 |
| Chicken (egg) | 5.19 | N.D. | >200 | >200 | >200 | >200 |

N.D. = not determined

In the 3 mM phosphate, pH 6.2 buffer, labeled DX-236 bound to all the albumins tested with high affinity, except for murine serum albumin (MSA). In PBS, the same affinity trend appeared with DX-236, except all the $K_D$ values were higher than for the low salt, pH 6.2 condition.

Labeled DX-321 bound each mammalian albumin with a substantially higher $K_D$ compared to HSA in the low salt, pH 6.2 buffer. In particular, MSA bound DX-321 with a $K_D$ greater than 200 μM compared to HSA, which bound DX-321 with a submicromolar $K_D$. All of the other non-human albumins also bound weakly to DX-321 and had $K_D$ values at least 10 times greater than for HSA. In PBS, however, the DX-321 affinity differences between HSA and the others were less pronounced compared to the pH 6.2 results. As a negative control, each peptide (DX-236 and DX-321) was also tested for binding to chicken ovalbumin in both sets of buffers and found that neither peptide showed any significant binding (Table 4). Chicken ovalbumin is not homologous to HSA as determined by sequence alignment analysis. This analysis indicated that immobilized DX-236 could be used to purify other mammalian albumins, whereas DX-321 may show differential binding to different mammalian albumins, in the pH 6.2 buffer.

To demonstrate this property, the same DX-236- and DX-321-SEPHAROSE® columns were tested against bovine serum albumin (BSA), goat serum albumin (GSA), and murine serum albumin (MSA) in the pH 6.2 buffer. One mg of each type of albumin was injected onto each column (0.35 ml) previously equilibrated in 3 mM Phosphate, pH 6.2, 0.01% TWEEN-20®. The columns were washed with equilibration buffer and then eluted with 100 mM Tris, pH 9.1 (flow rate, 1 ml/min). As shown in Table 5 below, DX-236-Sepharose quantitatively captured all three albumins like HSA.

TABLE 5

Mammalian Serum Albumin Testing with DX-236 and DX-321

| Albumin | Protein Load | DX-236 Column FT (mg) | DX-236 Column Elution (mg) | DX-321 Column FT (mg) | DX-321 Column Elution (mg) |
| --- | --- | --- | --- | --- | --- |
| Bovine | 1 mg | 0 | 0.72 | 0.86 | 0.15 |
| Goat | 1 mg | 0 | 0.79 | 0.93 | 0.11 |
| Mouse | 0.5 mg | 0.05 | 0.59 | 0.49 | 0.13 |

FT = flowthrough

Since Cibacron Blue SEPHAROSE® resin does not bind all mammalian albumins equally well (Mahany et al., *Comp. Biochem. Physiol.*, 68–319-323 (1981)), DX-236-SEPHAROSE® should prove useful as a "pan-albumin" binder for the affinity purification of nearly any mammalian albumin from serum. These results indicate that DX-236 could also be used to deplete albumin from serum samples prior to other analyses. This DX-236 ligand column, however, could not be used to purify HSA away from other non-human mammalian serum albumins, for example, in a transgenic mammalian expression system, such as HSA expressed in murine milk. However, the results also indicate that DX-236 could be used to purify HSA in a recombinant system that is devoid of other mammalian albumins, such as, but not limited to, recombinant poultry (e.g., recombinant chicken egg white), recombinant bacterial species, recombinant fungal species, such as, *Pichia pastoris* and *Saccharomyces cerevisiae*, and various leafy or tuber plant species, such as tobacco and potato plants.

The data in Table 5 also show that DX-321-SEPHAROSE® captures the three non-human albumins poorly, as is expected based on the solution affinity data shown in Table 4. Of the three non-human albumins, BSA was captured most effectively by the DX-321-SEPHAROSE® resin. About 15% of the BSA present in the starting material was captured and subsequently eluted under the same chromatography conditions that allowed quantitative capture of DX-236-SEPHAROSE® resin. Goat serum albumin (GSA) and mouse serum albumin (MSA) were even less effectively captured by the DX-321-SEPHAROSE® column than with BSA. Thus, the DX-321-SEPHAROSE® column may be advantageously used to purify HSA from solutions containing non-human serum albumins.

Purification of HSA from Serum

HSA was purified from blood serum using a preparative DX-236-SEPHAROSE® column (10 ml, 0.3 μmol/ml). Both the column and the serum sample were exchanged into 3 mM sodium phosphate, 20 mM NaCl, 0.1% TWEEN-20®, pH 6.2. The 20 mM NaCl was added to the binding buffer to minimize nonspecific protein binding to the column. A 100 μl aliquot (approximately 5 mg HSA) was applied to the DX-236-SEPHAROSE® column previously equilibrated in the same buffer used for dialysis. A salt gradient between 20 and 44 mM was run, and then HSA was eluted with 100 mM Tris, pH 9.1. The results of the purification process are shown in Table 6.

Purification of HSA Using DX-236 SEPHAROSE® Affinity Column

TABLE 6

Purification of HSA Using DX-236 Sepharose Affinity Column

| Fraction | μg HSA | % Initial |
| --- | --- | --- |
| Initial Load | 4805 | 100 |
| Flowthrough | 565 | 12 |
| Wash/Gradient | 88 | 1.8 |
| Elution | 4003 | 83 |
| Total | 4656 | 96.8 |

Figure 7A:
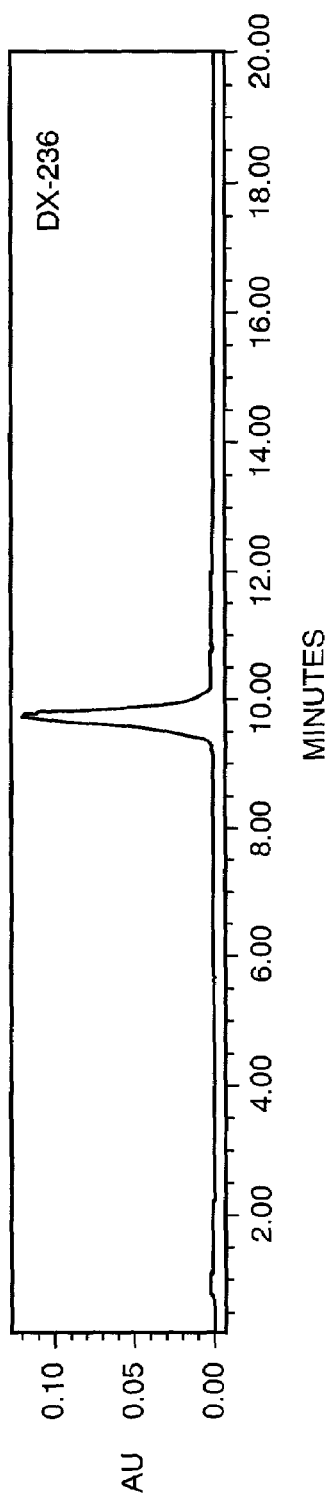
FIGS. 7A and 7B show purity in reverse phase HPLC fractions of HSA purified from whole human serum using a DX-236 SEPHAROSE® affinity column and a Cibacron SEPHAROSE® affinity chromatography column, respectively. Protein in HPLC fractions was monitored by absorbance at 280 nm.
Figure 7B:
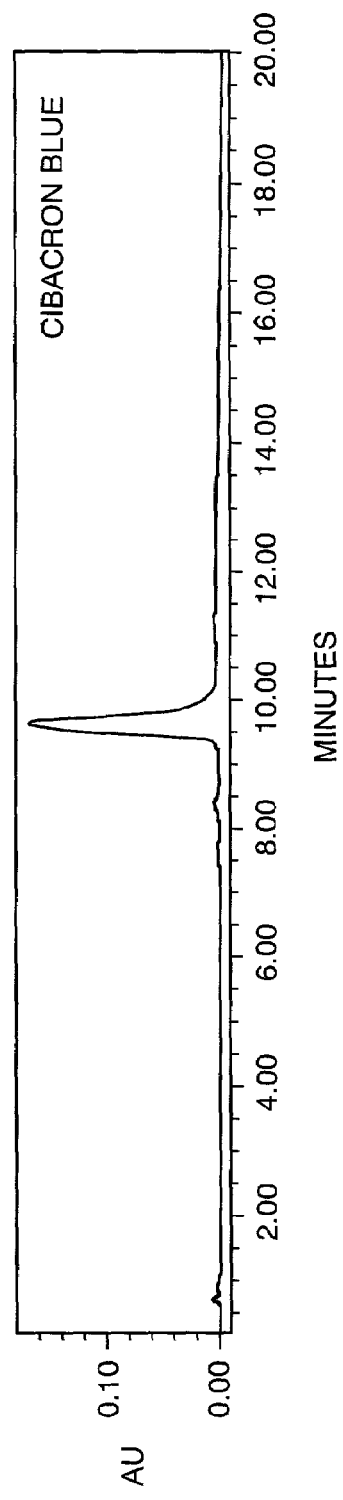

As shown in Table 6, the column bound essentially all the HSA in a 0.1 ml serum injection (~5 mg HSA total) and released essentially all the bound HSA with a 100 mM Tris, pH 9.1 wash (Table 6). The final purified material was greater than 99% pure by both reverse phase chromatography and SDS polyacrylamide gel electrophoresis. The purified material was compared to HSA purified using Cibacron Blue SEPHAROSE® column and found to be of higher purity (see, FIGS. 7A and 7B).

Comparison to HSA Binding Peptide Derived from Cytochrome C

Besides using Cibacron Blue SEPHAROSE® to purify HSA, Pingali et al. (*J. Mol. Reconit.*, 9: 426–436 (1996)) reported the HSA purification properties of an immobilized cytochrome c-derived peptide GAQGHTVEK (SEQ ID NO: 45), which is a Cys to Gly (underlined residues) mutation of the peptide originally characterized by Adams et al. (*J. Inorg. Biochem.*, 37: 91–103 (1989)). In their studies, the linear peptide was synthesized directly on POROS-amine resin (Applied Biosystems) with a single C-terminal 6-aminohexanoic acid linker at a peptide loading of 93 μmol/g resin, which is over 100-fold higher than the ligand densities used for DX-236-SEPHAROSE® (~0.3–0.8 μmol/ml) in this study.

Since the affinity of the cytochrome c-derived mutant peptide of Pingali et al. was not reported, the fluorescein labeled peptide was synthesized. This peptide binds weakly to HSA with a $K_D$ of approximately 335 μM, which is more than 100-fold greater than the DX-236 $K_D$ in the same buffer (Table 1). The peptide of Pignali et al., immobilized at a high ligand density, effectively binds HSA from human serum. The DX-236 HSA binding moiety described herein binds at a much higher affinity compared to the cytochrome c peptide. And substantially less of the DX-236 binding moiety is required on a chromatography column to get the same level of performance as a column prepared with cytochrome c derived peptide of Pingali et al.

Example 2

Alanine Scan of DX-236

A series of alanine mutants was synthesized based on the DX-236 polypeptide (SEQ ID NO: 19), by solid phase synthesis (Advanced Chemtech, Inc.):

| Polypeptide Sequence | SEQ ID NO: |
|---|---|
| Ac-AEGTGDFWFCDRIAWYPQHLCEFLAPEGGGK-NH$_2$, | 113 |
| Ac-AEGTGDFWFCDRIAWYPQHLCEFADPEGGGK-NH$_2$, | 114 |
| Ac-AEGTGDFWFCDRIAWYPQHLCEALDPEGGGK-NH$_2$, | 115 |
| Ac-AEGTGDFWFCDRIAWYPQHLCAFLDPEGGGK-NH$_2$, | 116 |
| Ac-AEGTGDFWFCDRIAWYPQHACEFLDPEGGGK-NH$_2$, | 117 |
| Ac-AEGTGDFWFCDRIAWYPQALCEFLDPEGGGK-NH$_2$, | 118 |
| Ac-AEGTGDFWFCDRIAWYPAHLCEFLDPEGGGK-NH$_2$, | 119 |
| Ac-AEGTGDFWFCDRIAWYAQHLCEFLDPEGGGK-NH$_2$, | 120 |
| Ac-AEGTGDFWFCDRIAWAPQHLCEFLDPEGGGK-NH$_2$, | 121 |
| Ac-AEGTGDFWFCDRIAAYPQHLCEFLDPEGGGK-NH$_2$, | 122 |
| Ac-AEGTGDFWFCDRAAWYPQHLCEFLDPEGGGK-NH$_2$, | 123 |
| Ac-AEGTGDFWFCDAIAWYPQHLCEFLDPEGGGK-NH$_2$, | 124 |
| Ac-AEGTGDFWFCARIAWYPQHLCEFLDPEGGGK-NH$_2$, | 125 |
| Ac-AEGTGDFWACDRIAWYPQHLCEFLDPEGGGK-NH$_2$, | 126 |
| Ac-AEGTGDFAFCDRIAWYPQHLCEFLDPEGGGK-NH$_2$, | 127 |
| Ac-AEGTGDAWFCDRIAWYPQHLCEFLDPEGGGK-NH$_2$, | 128 |
| Ac-AEGTGAFWFCDRIAWYPQHLCEFLDPEGGGK-NH$_2$, | 129 |

Each of the polypeptides was fluoresceinated and tested for binding against an immobilized HSA target as described above. Dissociation constants ($K_D$) in 3 mM phosphate buffer, pH 6.2, no salt, and in PBS were determined; binding affinity was estimated using the PBS dissociation constants, in comparison to the value for DX-236 (SEQ ID NO: 19), with "+" indicating about a 25% higher affinity binding compared with DX-236, "++" indicating about a 50% higher affinity, and "–" indicating about a 25% lower affinity.

The results are set forth in Table 7.

TABLE 7

Dissociation constants from alanine mutants of DX-236

| SEQ ID NO: | $K_D$ (μM) pH 6.2 | $K_D$ (μM) PBS | BINDING |
|---|---|---|---|
| 19 | 1.7 | 35.0 | |
| 113 | 1.7 | 10.5 | ++ |
| 114 | 2.1 | 47.0 | – |
| 115 | 1.7 | 44.0 | – |
| 116 | 1.7 | 6.6 | ++ |
| 117 | 2.0 | 34.5 | |
| 118 | 1.7 | 4.2 | ++ |
| 119 | 2.2 | 22.5 | + |
| 120 | 1.3 | 43.0 | |
| 121 | 1.4 | 26.0 | + |
| 122 | 1.4 | 44.0 | – |
| 123 | 1.1 | 4.5 | ++ |
| 124 | 1.5 | 17.5 | ++ |
| 125 | 1.6 | 5.0 | ++ |
| 126 | 1.1 | 43.0 | |
| 127 | 2.3 | 36.5 | |
| 128 | 5.1 | 26.5 | |
| 129 | 5.1 | 27.0 | |

Surprisingly, many of the alanine mutant polypeptides bound to HSA with higher affinities than the DX-236peptide (SEQ ID NO: 19). SEQ ID NOs: 113, 116, 118, 123, 124, and 125 bound HSA with at least 50% greater affinity than DX-236 (0.5 times the $K_D$ of DX-236

Example 3

Selection of Additional HSA Binding Polypeptides

Following the procedures of Example 1, the TN6/6, TN10/9, and TN12/1 libraries were selected against actively immobilized HSA beads. Additional libraries were also selected against the HSA bead target: TN8/9, TN9/4 and a linear library, Lin20.

THE TN8/9 library was constructed to display a single microprotein binding loop contained in a 14-amino acid template. The TN8/9 library utilized a template sequence of Xaa$_1$-Xaa$_2$-Xaa$_3$-Cys-Xaa$_5$-Xaa$_6$-Xaa$_7$-Xaa$_8$-Xaa$_9$-Xaa$_{10}$-Cys-Xaa$_{12}$-Xaa$_{13}$-Xaa$_{14}$ (SEQ ID NO: 235). The amino acids at position 1, 2, 3, 5, 6, 7, 8, 9, 10, 12, 13, and 14 in the template were varied to permit any amino acid except cysteine (Cys).

The N9/4 library was constructed to display a single microprotein binding loop contained in a 15-amino acid template. The TN9/4 library utilized a template sequence Xaa$_1$-Xaa$_2$-Xaa$_3$-Cys-Xaa$_5$-Xaa$_6$-Xaa$_7$-Xaa$_8$-Xaa$_9$-Xaa$_{10}$-Xaa$_{11}$-Cys-Xaa$_{13}$-Xaa$_{14}$-Xaa$_{15}$ (SEQ ID NO: 36). The amino acids at position 1, 2, 3, 5, 6, 7, 8, 9, 10, 11, 13, 14 and 15 in the temple were varied to permit any amino acid except cysteine (Cys).

The Lin20 library was constructed to display a single linear peptide in a 20-amino acid template. The amino acids at each position in the template were varied to permit any amino acid except cysteine (Cys).

Phage isolates were picked and sequenced robotically. The identified sequences and the $K_D$ values where determined, are set forth in Table 8.

| SEQ ID NO: | Amino Acid Sequence |
|---|---|
| | TN12/1 |
| 187 | LRDCQTTWPFTMMQCPNN |
| 188 | NRECVTMWPFEQIFCPWP |
| 189 | LRSCFTYYPFTTFSCSPA |
| 190 | LSHCWTKFPFDLVWCDSP |
| 191 | LRMCVSYWPHFVPVCENP |
| 192 | LRDCYISFPFDQMYCSHF |
| 193 | FRHCSVQYPFEVVVCPAN |
| 194 | LRNCWTQYPFDHSTCSPN |
| 195 | DSMCITWPFKRPWPCAN * |
| 196 | AFMCISWPFEMPFHCSPD |
| 197 | DSMCITWPFKRPWPCANP |
| 198 | WDLCITYPFHEMFPCEDG |
| 199 | GGECITWPFQTSYPCTNG |
| 200 | RNMCKFSWIRSPAFCARA |
| 201 | FSLCWIVDEDGTKWCLP * |
| 202 | RWFCDSAYWQEIPACARD |
| 203 | RWYCLWDPMLCMSD * |
| 204 | AWYCEHPYWTEVDKCHSS |
| 205 | SDFCDTPYWRDLWQCNSP |
| 206 | LPWCQLPYMSTPEFCIRP |
| 207 | YHVCGRGFDKESIYCKFL |
| 208 | SFCVTYIGTWETVCKRS * |
| 209 | NDGCTDTNWSWMFDCPPL |
| 210 | WRDCTLEIGTWFVFCKGS |
| 211 | SPYCKIALFQHFEVCAAD |
| 212 | RHWCIKLYGLGHMYCNRS |
| 213 | DHACEMQSIIPWWECYPH |
| 214 | PRSCVEKYYWDVLICGFF |
| 215 | FHTCPHGRYSMFPCDYW * |
| 216 | HGWCNVRWTDTPYWCAFS |
| 217 | YRVCTYDPIADLLFCPFN |
| | TN10/9 |
| 218 | RSFCMDWPNHRDCDYS |
| 219 | FWDCFPIHLTMFCDRF |
| 220 | YLYCQTSFTNYWCAFH |
| | TN9/4 |
| 221 | GLYCMEFGPDDCAWH |
| | TN8/7 |
| 222 | KNFCSWDPIFCGIH |
| 223 | KWYCAWDPLVCEIF |
| 224 | WTTCHIYDWFCSSS |
| 225 | QWYCLWDPMICGLI |
| 226 | QTNCSPPGKTCDKN |
| 227 | AICTFWQYWCLEP * |
| 228 | FEWCMFELPFCSWP |
| 229 | QEGCFSKPDQCKVM |
| 230 | LEYCFYQWWGCPHA |
| 231 | YQFCTWDPIFCGWH |
| | TN6/6 |
| 232 | LWDCWLYDCEGN |
| 233 | VHSCDKYGCVNA |
| 234 | FEHCSKDTCSGN |
| | Lin20 |
| 136 | PTVVQPKFHAFTHEDLLWIF |
| 137 | LKSQMVHALPAASLHDQHEL |
| 138 | SQVQGTPDLQFTVRDFIYMF |

*During the course of DNA synthesis, there is always a small percentage of incomplete couplings at each cycle. Since the libraries used were constructed by coupling trinucleotides (codons) instead of single nucleotides, the library template DNA often has a small percentage of deleted codons. In the case of the isolate sequences marked with an asterisk (*), binding phage displaying a shorter polypeptide than the template design were present in the library and were isolated when exposed to the HSA target.

Selected HSA binding polypeptides from these additional library selections were synthesized, fluorescein-labeled as in Example 1, and tested to determine an apparent $K_D$ for HSA in PBS. The polypeptides were synthesized to include an acetylated N-terminal dipeptide and a C-terminal dipeptide corresponding to the constant flanking amino acids immediately adjacent the display peptide as expressed on phage in the respective phage display libraries. The polypeptides were also synthesized with a C-terminal -Gly-Gly-Gly-Lys (SEQ ID NO: 24). The terminal Lys residue was amidated. The synthesized selected polypeptides and determined $K_D$ values are set forth in Table 9, below.

TABLE 9

Determination of $K_D$ for Selected HSA Binders

| SEQ ID NO: | Amino Acid Sequence | DX-# | $K_D$ (PBS) (μM) |
|---|---|---|---|
| TN12/1 | | | |
| 252 | Ac-GDLRDCQTTWPFTMMQCPNNDPGGGK—NH$_2$ | DX-1002 | 4 |
| 253 | Ac-GDNRECVTMWPFEQIFCPWPDPGGGK—NH$_2$ | DX-999 | 12 |
| 254 | Ac-GDLRSCFTYYPFTTFSCSPADPGGGK—NH$_2$ | DX-1091 | >10 |
| 255 | Ac-GDDSMCITWPFKRPWPCANDPGGGK—NH$_2$ | DX-1163 | 42 |
| 256 | Ac-GDRNMCKFSWIRSPAFCARADPGGGK—NH$_2$ | DX-321 | >10 |
| 257 | Ac-GDFSLCWIVDEDGTKWCLPDPGGGK—NH$_2$ | DX-997 | >10 |
| 258 | Ac-GDRWFCDSAYWQEIPACARDDPGGGK—NH$_2$ | DX-1085 | NB |
| 259 | Ac-GDSDFCDTPYWRDLWQCNSPDPGGGK—NH$_2$ | DX-1087 | NB |
| 260 | Ac-GDSFCVTYIGTWETVCKRSDPGGGK—NH$_2$ | DX-1089 | >10 |
| 261 | Ac-GDNDGCTDTNWSWMFDCPPLDPGGGK—NH$_2$ | DX-1165 | >10 |
| 262 | Ac-GDSPYCKIALFQHFEVCAADDPGGGK—NH$_2$ | DX-1167 | >10 |
| 263 | Ac-GDPRSCVEKYYWDVLICGFFDPGGGK—NH$_2$ | DX-1169 | NB |
| TN10/9 | | | |
| 264 | Ac-GSRSFCMDWPNHRDCDYSAPGGGK—NH$_2$ | DX-1171 | 165 |
| TN8/9 | | | |
| 265 | Ac-AGKWYCAWDPLVCEIFGTGGGK—NH$_2$ | DX-1173 | >10 |
| 266 | Ac-AGWTTCHIYDWFCSSSGTGGGK—NH$_2$ | DX-1175 | 30 |

TABLE 9-continued

Determination of $K_D$ for Selected HSA Binders

| SEQ ID NO: | Amino Acid Sequence | DX-# | $K_D$ (PBS) (μM) |
|---|---|---|---|
| 267 | Ac-AGLEYCFYQWWGCPHAGTGGGK—NH$_2$ | DX-1177 | 153 |
| 268 | Ac-AGYQFCTWDPIFCGWHGTGGGK—NH$_2$ | DX-1179 | 185 |
| TN6/6 | | | |
| 269 | Ac-GSLWDCWLYDCEGNAPGGGK—NH$_2$ | DX-1093 | >10 |

"Ac-" signifies N-terminal acetylation
"—NH$_2$" signifies C-terminal amidation
"NB" signifies no significant binding ($K_D$ > 30 μM)

The foregoing examples illustrate new, non-natural, isolated peptides that bind mammalian serum albumin, such as HSA, with micromolar affinity. Once immobilized on a chromatography resin, representative serum albumin binding peptides of the invention are capable of binding and releasing HSA under gentle elution conditions. DX-236-SEPHAROSE® affinity resin, in particular, captures HSA very effectively out of human serum and performs better than Cibacron Blue SEPHAROSE® affinity resin in terms of final HSA purity. This discovery, therefore, highlights the power of phage display for isolating peptides that bind a serum albumin target with high specificity. Not only can this technology be applied to designing highly specific affinity media for serum albumins, but as explained above, such peptides and molecules comprising such peptides as described herein may also be used for therapeutic and diagnostic applications where a serum albumin is the target of the therapeutic or detection protocol.

The patents and publications mentioned above are incorporated herein by reference.

What is claimed is:

1. An isolated protein comprising an amino acid sequence of formula (1):

Cys-Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Cys (SEQ ID NO :4), wherein the amino acid sequence of formula (1) is selected from the group consisting of C E G K D M I D W V Y C (SEQ ID NO:8),
C D R I A W Y P Q H L C (SEQ ID NO:9),
C D R I A W Y P Q H A C (SEQ ID NO:72),
C D R I A W Y P Q A L C (SEQ ID NO:73),
C D R I A W Y P A H L C (SEQ ID NO:74),
C D R I A W Y A Q H L C (SEQ ID NO:75),
C D R I A W A P Q H L C (SEQ ID NO:76),
C D R I A A Y P Q H L C (SEQ ID NO:77),
C D R A A W Y P Q H L C (SEQ ID NO:78),
C D A I A W Y P Q H L C (SEQ ID NO:79),
C A R I A W Y P Q H L C (SEQ ID NO:80),
C V T R W A N R D Q Q C (SEQ ID NO:15),
C V T D W A N R H Q H C (SEQ ID NO:16),
C V K D W A N R R R G C (SEQ ID NO:17),
C K F S W I R S P A F C (SEQ ID NO:18),
C Q T T W P F T M M Q C (SEQ ID NO:139),
C V T M W P F E Q I F C (SEQ ID NO:140),
C F T Y Y P F T T F S C (SEQ ID NO:141),
C W T K F P F D L V W C (SEQ ID NO:142),
C V S Y W P H F V P V C (SEQ ID NO:143),
C Y I S F P F D Q M Y C (SEQ ID NO:144),
C S V Q Y P F E V V V C (SEQ ID NO:145),
C W T Q Y P F D H S T C (SEQ ID NO:146),
C I T W P F K R P W P C (SEQ ID NO:147),
C I S W P F E M P F H C (SEQ ID NO:148),
C I T W P F K R P W P C (SEQ ID NO:149),
C I T Y P F H E M F P C (SEQ ID NO:150),
C I T W P F Q T S Y P C (SEQ ID NO:151),
C K F S W I R S P A F C (SEQ ID NO:152),
C W I V D E D G T K W C (SEQ ID NO:153),
C D S A Y W Q E I P A C (SEQ ID NO:154),
C E H P Y W T E V D K C (SEQ ID NO:156),
C D T P Y W R D L W Q C (SEQ ID NO:157),
C Q L P Y M S T P E F C (SEQ ID NO:158),
C G R G F D K E S I Y C (SEQ ID NO:159),
C V T Y I G T W E T V C (SEQ ID NO:160),
C T D T N W S W M F D C (SEQ ID NO:161),
C T L E I G T W F V F C (SEQ ID NO:162),
C K I A L F Q H F E V C (SEQ ID NO:163),
C I K L Y G L G H M Y C (SEQ ID NO:164),
C E M Q S L I P W W E C (SEQ ID NO:165),
C V E K Y Y W D V L I C (SEQ ID NO:166),
C N V R W T D T P Y W C (SEQ ID NO:168), and
C T Y D P I A D L L F C (SEQ ID NO:169), wherein a disulfide bond is formed between cysteine residues, and wherein the protein binds human serum albumin.

2. The protein according to claim 1, wherein said protein is part of a recombinant bacteriophage.

3. A composition of matter comprising a protein according to claim 1, linked to solid support material selected from the group consisting of cellulose, plastic, metal, rubber, wood, nylon, glass, acrylamide, agarose, and combinations thereof.

4. A composition of matter comprising a protein according to claim 1 immobilized on a chromatographic matrix material.

5. A composition of matter comprising a protein according to claim 1, conjugated with another molecule, wherein the conjugate binds serum albumin.

6. The composition according to claim 5, wherein said protein is linked to a detectable label.

7. The composition according to claim 6, wherein said detectable label is selected from the group consisting of radionuclides, detectable proteins, epitope tags, biotin, streptavidin, enzymes, antibodies, and fluorescent labels.

8. The composition according to claim 6, wherein the detectable label is a technetium-containing compound.

9. The composition according to claim 5, wherein said molecule is a drug, biopharmaceutical, or protein of interest.

10. A method for detecting human serum albumin in a solution comprising:
    (a) contacting said solution with a composition according to claim 6 under conditions wherein said composition will form a complex with said serum albumin, and
    (b) detecting said complex, to thereby detect human serum in the solution.

11. The method according to claim 10, wherein the solution is blood.

12. A method for isolating human serum albumin from a solution containing it comprising:
    (a) immobilizing a protein according to claim 1 on a solid support;

(b) contacting a solution containing human serum albumin with said solid support of (a) under conditions where said protein will form a complex with said human serum albumin; and, thereafter, (c) separating the solid support from the unbound components of said solution, to thereby isolate human serum albumin from the solution.

13. The method according to claim 12, wherein said solid support is selected from the group consisting of chromatographic matrix materials, filters, magnetic beads, and the surface of a plastic or glass container.

14. The method according to claim 12, further comprising the step:

(d) eluting and recovering the human serum albumin from said support.

15. The method according to claim 12, wherein the solution is selected from the group consisting of transgenic chicken egg white, a recombinant eukaryotic or prokaryotic cell extract, and whole blood.

16. A method for isolating human serum albumin from a solution containing it comprising:

(a) contacting a solution containing human serum albumin with a protein according to claim 1, in which said protein is conjugated to an affinity ligand under conditions suitable for formation of a binding complex between said protein and said human serum albumin;

(b) contacting the solution of step (a) with an immobilized binding partner for said affinity ligand under conditions suitable for formation of a binding complex between the affinity ligand and the binding partner;

(c) removing unbound materials in the solution from any complex formed in step (b), to thereby isolate human serum albumin from the solution.

17. The method according to claim 16, wherein said affinity ligand is a polyhistidine tag.

18. The method according to claim 16, wherein said affinity ligand is biotin and said immobilized binding partner for said affinity ligand is streptavidin.

19. The isolated protein according to claim 1, wherein said protein comprises the sequence C D R I A W Y P Q H L C (SEQ ID NO:9).

20. The isolated protein according to claim 1, wherein said polypetide comprises the sequence C K F S W I R S P A F C (SEQ ID NO:18).

* * * * *

SEQUENCE LISTING

```
<160> NUMBER OF SEQ ID NOS: 271

<210> SEQ ID NO 1
<211> LENGTH: 6
<212> TYPE: PRT
<213> ORGANISM: Artificial Sequence
<220> FEATURE:
<223> OTHER INFORMATION: albumin binding peptide
<221> NAME/KEY: MISC_FEATURE
<222> LOCATION: (2)..(2)
<223> OTHER INFORMATION: Thr, Asp, Asn or Trp
<221> NAME/KEY: MISC_FEATURE
<222> LOCATION: (3)..(3)
<223> OTHER INFORMATION: Ile, Gln, Asn or His
<221> NAME/KEY: MISC_FEATURE
<222> LOCATION: (4)..(4)
<223> OTHER INFORMATION: Phe, Trp or Ala
<221> NAME/KEY: MISC_FEATURE
<222> LOCATION: (5)..(5)
<223> OTHER INFORMATION: Leu, Phe or Ser

<400> SEQUENCE: 1

Cys Xaa Xaa Xaa Xaa Cys
1               5

<210> SEQ ID NO 2
<211> LENGTH: 12
<212> TYPE: PRT
<213> ORGANISM: Artificial Sequence
<220> FEATURE:
<223> OTHER INFORMATION: albumin binding peptide
<221> NAME/KEY: MISC_FEATURE
<222> LOCATION: (1)..(1)
<223> OTHER INFORMATION: Val, Phe, His, Trp, or Asn
<221> NAME/KEY: MISC_FEATURE
<222> LOCATION: (2)..(2)
<223> OTHER INFORMATION: Ala, Lys, Val, or His
<221> NAME/KEY: MISC_FEATURE
<222> LOCATION: (3)..(3)
<223> OTHER INFORMATION: Trp, Ile, Gly, or Val
<221> NAME/KEY: MISC_FEATURE
```

```
<222> LOCATION: (5)..(5)
<223> OTHER INFORMATION: Thr, Asp, Asn, or Trp
<221> NAME/KEY: MISC_FEATURE
<222> LOCATION: (6)..(6)
<223> OTHER INFORMATION: Ile, Gln, Asn, or His
<221> NAME/KEY: MISC_FEATURE
<222> LOCATION: (7)..(7)
<223> OTHER INFORMATION: Phe, Trp, or Ala
<221> NAME/KEY: MISC_FEATURE
<222> LOCATION: (8)..(8)
<223> OTHER INFORMATION: Leu, Phe, or Ser
<221> NAME/KEY: MISC_FEATURE
<222> LOCATION: (10)..(10)
<223> OTHER INFORMATION: Leu, Met, or Ile
<221> NAME/KEY: MISC_FEATURE
<222> LOCATION: (11)..(11)
<223> OTHER INFORMATION: Asp, Met, Gln, Ser, or Trp
<221> NAME/KEY: MISC_FEATURE
<222> LOCATION: (12)..(12)
<223> OTHER INFORMATION: Val, Pro, Tyr, or Asp

<400> SEQUENCE: 2

Xaa Xaa Xaa Cys Xaa Xaa Xaa Xaa Cys Xaa Xaa Xaa
1               5                   10

<210> SEQ ID NO 3
<211> LENGTH: 21
<212> TYPE: PRT
<213> ORGANISM: Artificial Sequence
<220> FEATURE:
<223> OTHER INFORMATION: albumin binding peptide
<221> NAME/KEY: MISC_FEATURE
<222> LOCATION: (7)..(7)
<223> OTHER INFORMATION: Val, Phe, His, Trp, or Asn
<221> NAME/KEY: MISC_FEATURE
<222> LOCATION: (8)..(8)
<223> OTHER INFORMATION: Ala, Lys, Val, or His
<221> NAME/KEY: MISC_FEATURE
<222> LOCATION: (9)..(9)
<223> OTHER INFORMATION: Trp, Ile, Gly, or Val
<221> NAME/KEY: MISC_FEATURE
<222> LOCATION: (11)..(11)
<223> OTHER INFORMATION: Thr, Asp, Asn, or Trp
<221> NAME/KEY: MISC_FEATURE
<222> LOCATION: (12)..(12)
<223> OTHER INFORMATION: Ile, Gln, Asn, or His
<221> NAME/KEY: MISC_FEATURE
<222> LOCATION: (13)..(13)
<223> OTHER INFORMATION: Phe, Trp, or Ala
<221> NAME/KEY: MISC_FEATURE
<222> LOCATION: (14)..(14)
<223> OTHER INFORMATION: Leu, Phe, or Ser
<221> NAME/KEY: MISC_FEATURE
<222> LOCATION: (16)..(16)
<223> OTHER INFORMATION: Leu, Met, or Ile
<221> NAME/KEY: MISC_FEATURE
<222> LOCATION: (17)..(17)
<223> OTHER INFORMATION: Asp, Met, Gln, Ser, or Trp
<221> NAME/KEY: MISC_FEATURE
<222> LOCATION: (18)..(18)
<223> OTHER INFORMATION: Val, Pro, Tyr, or Asp

<400> SEQUENCE: 3

Ala Glu Gly Thr Gly Ser Xaa Xaa Xaa Cys Xaa Xaa Xaa Xaa Cys Xaa
1               5                   10                  15

Xaa Xaa Ala Pro Glu
            20

<210> SEQ ID NO 4
<211> LENGTH: 12
<212> TYPE: PRT
<213> ORGANISM: Artificial Sequence
<220> FEATURE:
<223> OTHER INFORMATION: albumin binding peptide
```

```
<221> NAME/KEY: MISC_FEATURE
<222> LOCATION: (2)..(2)
<223> OTHER INFORMATION: Glu, Asp, Val, or Lys
<221> NAME/KEY: MISC_FEATURE
<222> LOCATION: (3)..(3)
<223> OTHER INFORMATION: Gly, Arg, Thr, Lys, or Phe
<221> NAME/KEY: MISC_FEATURE
<222> LOCATION: (4)..(4)
<223> OTHER INFORMATION: Lys, Ile, Arg, Asp, or Ser
<221> NAME/KEY: MISC_FEATURE
<222> LOCATION: (5)..(5)
<223> OTHER INFORMATION: Asp, Ala, or Trp
<221> NAME/KEY: MISC_FEATURE
<222> LOCATION: (6)..(6)
<223> OTHER INFORMATION: Met, Trp, Ala, or Ile
<221> NAME/KEY: MISC_FEATURE
<222> LOCATION: (7)..(7)
<223> OTHER INFORMATION: Ile, Tyr, Asn, or Arg
<221> NAME/KEY: MISC_FEATURE
<222> LOCATION: (8)..(8)
<223> OTHER INFORMATION: Asp, Pro, Arg, or Ser
<221> NAME/KEY: MISC_FEATURE
<222> LOCATION: (9)..(9)
<223> OTHER INFORMATION: Trp, Gln, Asp, His, Arg, or Pro
<221> NAME/KEY: MISC_FEATURE
<222> LOCATION: (10)..(10)
<223> OTHER INFORMATION: Val, His, Gln, Arg, or Ala
<221> NAME/KEY: MISC_FEATURE
<222> LOCATION: (11)..(11)
<223> OTHER INFORMATION: Tyr, Leu, Gln, His, Gly, or Phe

<400> SEQUENCE: 4

Cys Xaa Xaa Xaa Xaa Xaa Xaa Xaa Xaa Xaa Xaa Cys
1               5                   10

<210> SEQ ID NO 5
<211> LENGTH: 18
<212> TYPE: PRT
<213> ORGANISM: Artificial Sequence
<220> FEATURE:
<223> OTHER INFORMATION: albumin binding peptide
<221> NAME/KEY: MISC_FEATURE
<222> LOCATION: (1)..(1)
<223> OTHER INFORMATION: Ala, Phe, Asp, or Arg
<221> NAME/KEY: MISC_FEATURE
<222> LOCATION: (2)..(2)
<223> OTHER INFORMATION: Asp, Trp, or Asn
<221> NAME/KEY: MISC_FEATURE
<222> LOCATION: (3)..(3)
<223> OTHER INFORMATION: Phe, Asp, Gln, or Met
<221> NAME/KEY: MISC_FEATURE
<222> LOCATION: (5)..(5)
<223> OTHER INFORMATION: Glu, Asp, Val, or Lys
<221> NAME/KEY: MISC_FEATURE
<222> LOCATION: (6)..(6)
<223> OTHER INFORMATION: Gly, Arg, Thr, Lys, or Phe
<221> NAME/KEY: MISC_FEATURE
<222> LOCATION: (7)..(7)
<223> OTHER INFORMATION: Lys, Ile, Arg, Asp, or Ser
<221> NAME/KEY: MISC_FEATURE
<222> LOCATION: (8)..(8)
<223> OTHER INFORMATION: Asp, Ala, or Trp
<221> NAME/KEY: MISC_FEATURE
<222> LOCATION: (9)..(9)
<223> OTHER INFORMATION: Met, Trp, Ala, or Ile
<221> NAME/KEY: MISC_FEATURE
<222> LOCATION: (10)..(10)
<223> OTHER INFORMATION: Ile, Tyr, Asn, or Arg
<221> NAME/KEY: MISC_FEATURE
<222> LOCATION: (11)..(11)
<223> OTHER INFORMATION: Asp, Pro, Arg, or Ser
<221> NAME/KEY: MISC_FEATURE
<222> LOCATION: (12)..(12)
<223> OTHER INFORMATION: Trp, Gln, Asp, His, Arg, or Pro
<221> NAME/KEY: MISC_FEATURE
<222> LOCATION: (13)..(13)
<223> OTHER INFORMATION: Val, His, Gln, Arg, or Ala
```

-continued

```
<221> NAME/KEY: MISC_FEATURE
<222> LOCATION: (14)..(14)
<223> OTHER INFORMATION: Tyr, Leu, Gln, His, Gly, or Phe
<221> NAME/KEY: MISC_FEATURE
<222> LOCATION: (16)..(16)
<223> OTHER INFORMATION: Arg, Glu, Trp, Met, or Ala
<221> NAME/KEY: MISC_FEATURE
<222> LOCATION: (17)..(17)
<223> OTHER INFORMATION: Leu, Phe, Gly, Ala, or Arg
<221> NAME/KEY: MISC_FEATURE
<222> LOCATION: (18)..(18)
<223> OTHER INFORMATION: Tyr, Leu, Pro, Asp, or Ala

<400> SEQUENCE: 5

Xaa Xaa Xaa Cys Xaa Xaa Xaa Xaa Xaa Xaa Xaa Xaa Xaa Xaa Cys Xaa
1               5                   10                  15

Xaa Xaa

<210> SEQ ID NO 6
<211> LENGTH: 27
<212> TYPE: PRT
<213> ORGANISM: Artificial Sequence
<220> FEATURE:
<223> OTHER INFORMATION: albumin binding peptide
<221> NAME/KEY: MISC_FEATURE
<222> LOCATION: (7)..(7)
<223> OTHER INFORMATION: Ala, Phe, Asp, or Arg
<221> NAME/KEY: MISC_FEATURE
<222> LOCATION: (8)..(8)
<223> OTHER INFORMATION: Asp, Trp, or Asn
<221> NAME/KEY: MISC_FEATURE
<222> LOCATION: (9)..(9)
<223> OTHER INFORMATION: Phe, Asp, Gln, or Met
<221> NAME/KEY: MISC_FEATURE
<222> LOCATION: (11)..(11)
<223> OTHER INFORMATION: Glu, Asp, Val, or Lys
<221> NAME/KEY: MISC_FEATURE
<222> LOCATION: (12)..(12)
<223> OTHER INFORMATION: Gly, Arg, Thr, Lys, or Phe
<221> NAME/KEY: MISC_FEATURE
<222> LOCATION: (13)..(13)
<223> OTHER INFORMATION: Lys, Ile, Arg, Asp, or Ser
<221> NAME/KEY: MISC_FEATURE
<222> LOCATION: (14)..(14)
<223> OTHER INFORMATION: Asp, Ala, or Trp
<221> NAME/KEY: MISC_FEATURE
<222> LOCATION: (15)..(15)
<223> OTHER INFORMATION: Met, Trp, Ala, or Ile
<221> NAME/KEY: MISC_FEATURE
<222> LOCATION: (16)..(16)
<223> OTHER INFORMATION: Ile Tyr, Asn, or Arg
<221> NAME/KEY: MISC_FEATURE
<222> LOCATION: (17)..(17)
<223> OTHER INFORMATION: Asp, Pro, Arg, or Ser
<221> NAME/KEY: MISC_FEATURE
<222> LOCATION: (18)..(18)
<223> OTHER INFORMATION: Trp, Gln, Asp, His, Arg, or Pro
<221> NAME/KEY: MISC_FEATURE
<222> LOCATION: (19)..(19)
<223> OTHER INFORMATION: Val, His, Gln, Arg, or Ala
<221> NAME/KEY: MISC_FEATURE
<222> LOCATION: (20)..(20)
<223> OTHER INFORMATION: Tyr, Leu, Gln, His, Gly, or Phe
<221> NAME/KEY: MISC_FEATURE
<222> LOCATION: (22)..(22)
<223> OTHER INFORMATION: Arg, Glu, Trp, Met, or Ala
<221> NAME/KEY: MISC_FEATURE
<222> LOCATION: (23)..(23)
<223> OTHER INFORMATION: Leu, Phe, Gly, Ala, or Arg
<221> NAME/KEY: MISC_FEATURE
<222> LOCATION: (24)..(24)
<223> OTHER INFORMATION: Tyr, Leu, Pro, Asp, or Ala

<400> SEQUENCE: 6

Ala Glu Gly Thr Gly Asp Xaa Xaa Xaa Cys Xaa Xaa Xaa Xaa Xaa Xaa
```

```
            1               5                  10                 15
Xaa Xaa Xaa Xaa Cys Xaa Xaa Xaa Asp Pro Glu
            20                  25

<210> SEQ ID NO 7
<211> LENGTH: 6
<212> TYPE: PRT
<213> ORGANISM: Artificial Sequence
<220> FEATURE:
<223> OTHER INFORMATION: albumin binding peptide

<400> SEQUENCE: 7

Cys Thr Ile Phe Leu Cys
1               5

<210> SEQ ID NO 8
<211> LENGTH: 12
<212> TYPE: PRT
<213> ORGANISM: Artificial Sequence
<220> FEATURE:
<223> OTHER INFORMATION: albumin binding peptide

<400> SEQUENCE: 8

Cys Glu Gly Lys Asp Met Ile Asp Trp Val Tyr Cys
1               5                  10

<210> SEQ ID NO 9
<211> LENGTH: 12
<212> TYPE: PRT
<213> ORGANISM: Artificial Sequence
<220> FEATURE:
<223> OTHER INFORMATION: albumin binding peptide

<400> SEQUENCE: 9

Cys Asp Arg Ile Ala Trp Tyr Pro Gln His Leu Cys
1               5                  10

<210> SEQ ID NO 10
<211> LENGTH: 10
<212> TYPE: PRT
<213> ORGANISM: Artificial Sequence
<220> FEATURE:
<223> OTHER INFORMATION: albumin binding peptide

<400> SEQUENCE: 10

Cys Glu Pro Trp Met Leu Arg Phe Gly Cys
1               5                  10

<210> SEQ ID NO 11
<211> LENGTH: 6
<212> TYPE: PRT
<213> ORGANISM: Artificial Sequence
<220> FEATURE:
<223> OTHER INFORMATION: albumin binding peptide

<400> SEQUENCE: 11

Cys Asp Gln Trp Phe Cys
1               5

<210> SEQ ID NO 12
<211> LENGTH: 6
<212> TYPE: PRT
<213> ORGANISM: Artificial Sequence
<220> FEATURE:
<223> OTHER INFORMATION: albumin binding peptide

<400> SEQUENCE: 12
```

```
Cys Asn Asn Ala Leu Cys
1               5

<210> SEQ ID NO 13
<211> LENGTH: 6
<212> TYPE: PRT
<213> ORGANISM: Artificial Sequence
<220> FEATURE:
<223> OTHER INFORMATION: albumin binding peptide

<400> SEQUENCE: 13

Cys Asp His Phe Phe Cys
1               5

<210> SEQ ID NO 14
<211> LENGTH: 6
<212> TYPE: PRT
<213> ORGANISM: Artificial Sequence
<220> FEATURE:
<223> OTHER INFORMATION: albumin binding peptide

<400> SEQUENCE: 14

Cys Trp His Phe Ser Cys
1               5

<210> SEQ ID NO 15
<211> LENGTH: 12
<212> TYPE: PRT
<213> ORGANISM: Artificial Sequence
<220> FEATURE:
<223> OTHER INFORMATION: albumin binding peptide

<400> SEQUENCE: 15

Cys Val Thr Arg Trp Ala Asn Arg Asp Gln Gln Cys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: albumin binding peptide

<400> SEQUENCE: 16

Cys Val Thr Asp Trp Ala Asn Arg His Gln His Cys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: albumin binding peptide

<400> SEQUENCE: 17

Cys Val Lys Asp Trp Ala Asn Arg Arg Arg Gly Cys
1               5                   10

<210> SEQ ID NO 18
<211> LENGTH: 12
<212> TYPE: PRT
<213> ORGANISM: Artificial Sequence
<220> FEATURE:
<223> OTHER INFORMATION: albumin binding peptide

<400> SEQUENCE: 18
```

```
Cys Lys Phe Ser Trp Ile Arg Ser Pro Ala Phe Cys
1               5                   10
```

```
<210> SEQ ID NO 19
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: AMIDATION

<400> SEQUENCE: 19

Ala Glu Gly Thr Gly Asp Phe Trp Phe Cys Asp Arg Ile Ala Trp Tyr
1               5                   10                  15
Pro Gln His Leu Cys Glu Phe Leu Asp Pro Glu Gly Gly Gly Lys
            20                  25                  30
```

```
<210> SEQ ID NO 20
<211> LENGTH: 29
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (29)..(29)
<223> OTHER INFORMATION: AMIDATION
<221> NAME/KEY: MISC_FEATURE
<222> LOCATION: (28)..(28)
<223> OTHER INFORMATION: peptide linked 6 aminohexanoic acid group

<400> SEQUENCE: 20

Ala Glu Gly Thr Gly Asp Arg Asn Met Cys Lys Phe Ser Trp Ile Arg
1               5                   10                  15
Ser Pro Ala Phe Cys Ala Arg Ala Asp Pro Glu Xaa Lys
            20                  25
```

```
<210> SEQ ID NO 21
<211> LENGTH: 12
<212> TYPE: PRT
<213> ORGANISM: Artificial Sequence
<220> FEATURE:
<223> OTHER INFORMATION: variegated display library template
<221> NAME/KEY: MISC_FEATURE
<222> LOCATION: (1)..(1)
<223> OTHER INFORMATION: Ala, Asp, Phe, Gly, His, Leu, Asn, Pro, Gln,
      Arg, Ser, Val, Trp or Tyr
<221> NAME/KEY: MISC_FEATURE
<222> LOCATION: (2)..(3)
<223> OTHER INFORMATION: any amino acid, except Cys
<221> NAME/KEY: MISC_FEATURE
<222> LOCATION: (5)..(8)
<223> OTHER INFORMATION: X is any amino acid, except Cys
<221> NAME/KEY: MISC_FEATURE
<222> LOCATION: (10)..(11)
<223> OTHER INFORMATION: X is any amino acid, except Cys
<221> NAME/KEY: MISC_FEATURE
<222> LOCATION: (12)..(12)
<223> OTHER INFORMATION: Ala, Asp, Phe, Gly, His, Leu, Asn, Pro, Gln,
      Arg, Ser, Val, Trp, and Tyr

<400> SEQUENCE: 21

Xaa Xaa Xaa Cys Xaa Xaa Xaa Xaa Cys Xaa Xaa Xaa
1               5                   10
```

-continued

```
<210> SEQ ID NO 22
<211> LENGTH: 16
<212> TYPE: PRT
<213> ORGANISM: Artificial Sequence
<220> FEATURE:
<223> OTHER INFORMATION: variegated display library template
<221> NAME/KEY: MISC_FEATURE
<222> LOCATION: (1)..(2)
<223> OTHER INFORMATION: Asp, Phe, His, Leu, Asn, Pro, Arg, Ser, Trp,
      and Tyr
<221> NAME/KEY: MISC_FEATURE
<222> LOCATION: (3)..(3)
<223> OTHER INFORMATION: Ala, Asp, Glu, Phe, Gly, His, Leu, Asn, Pro,
      Arg, Ser, Val, Trp, and Tyr
<221> NAME/KEY: MISC_FEATURE
<222> LOCATION: (5)..(12)
<223> OTHER INFORMATION: any amino acid except Cys
<221> NAME/KEY: MISC_FEATURE
<222> LOCATION: (14)..(14)
<223> OTHER INFORMATION: Ala, Asp, Glu, Phe, Gly, His, Leu, Asn, Pro,
      Arg, Ser, Val, Trp, and Tyr
<221> NAME/KEY: MISC_FEATURE
<222> LOCATION: (15)..(16)
<223> OTHER INFORMATION: Asp, Phe, His, Leu, Asn, Pro, Arg, Ser, Trp,
      and Tyr

<400> SEQUENCE: 22

Xaa Xaa Xaa Cys Xaa Xaa Xaa Xaa Xaa Xaa Xaa Xaa Cys Xaa Xaa Xaa
1               5                   10                  15

<210> SEQ ID NO 23
<211> LENGTH: 18
<212> TYPE: PRT
<213> ORGANISM: Artificial Sequence
<220> FEATURE:
<223> OTHER INFORMATION: variegated display library template
<221> NAME/KEY: MISC_FEATURE
<222> LOCATION: (1)..(2)
<223> OTHER INFORMATION: Ala, Asp, Phe, Gly, His, Leu, Asn, Pro, Arg,
      Ser, Trp, and Tyr
<221> NAME/KEY: MISC_FEATURE
<222> LOCATION: (3)..(3)
<223> OTHER INFORMATION: any amino acid, except for Cys
<221> NAME/KEY: MISC_FEATURE
<222> LOCATION: (5)..(14)
<223> OTHER INFORMATION: any amino acid, except for Cys
<221> NAME/KEY: MISC_FEATURE
<222> LOCATION: (16)..(16)
<223> OTHER INFORMATION: any amino acid, except for Cys
<221> NAME/KEY: MISC_FEATURE
<222> LOCATION: (17)..(18)
<223> OTHER INFORMATION: Ala, Asp, Phe, Gly, His, Leu, Asn, Pro, Arg,
      Ser, Trp, Tyr

<400> SEQUENCE: 23

Xaa Xaa Xaa Cys Xaa Xaa Xaa Xaa Xaa Xaa Xaa Xaa Xaa Xaa Cys Xaa
1               5                   10                  15

Xaa Xaa

<210> SEQ ID NO 24
<211> LENGTH: 4
<212> TYPE: PRT
<213> ORGANISM: Artificial Sequence
<220> FEATURE:
<223> OTHER INFORMATION: peptide linker
<221> NAME/KEY: MOD_RES
<222> LOCATION: (4)..(4)
<223> OTHER INFORMATION: AMIDATION

<400> SEQUENCE: 24

Gly Gly Gly Lys
```

```
<210> SEQ ID NO 25
<211> LENGTH: 25
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (25)..(25)
<223> OTHER INFORMATION: AMIDATION

<400> SEQUENCE: 25

Ala Glu Gly Thr Gly Ser Val Ala Trp Cys Thr Ile Phe Leu Cys Leu
1               5                   10                  15

Asp Val Ala Pro Glu Gly Gly Gly Lys
            20                  25

<210> SEQ ID NO 26
<211> LENGTH: 23
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MISC_FEATURE
<222> LOCATION: (22)..(22)
<223> OTHER INFORMATION: peptide linked 6 aminohexanoic acid group
<221> NAME/KEY: MOD_RES
<222> LOCATION: (23)..(23)
<223> OTHER INFORMATION: AMIDATION

<400> SEQUENCE: 26

Ala Glu Gly Thr Gly Ser Phe Lys Ile Cys Asp Gln Trp Phe Cys Leu
1               5                   10                  15

Met Pro Ala Pro Glu Xaa Lys
            20

<210> SEQ ID NO 27
<211> LENGTH: 23
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MISC_FEATURE
<222> LOCATION: (22)..(22)
<223> OTHER INFORMATION: peptide linked 6 aminohexanoic acid group
<221> NAME/KEY: MOD_RES
<222> LOCATION: (23)..(23)
<223> OTHER INFORMATION: AMIDATION

<400> SEQUENCE: 27

Ala Glu Gly Thr Gly Ser His Val Gly Cys Asn Asn Ala Leu Cys Met
1               5                   10                  15

Gln Tyr Ala Pro Glu Xaa Lys
            20

<210> SEQ ID NO 28
<211> LENGTH: 23
<212> TYPE: PRT
<213> ORGANISM: Artificial Sequence
```

```
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MISC_FEATURE
<222> LOCATION: (22)..(22)
<223> OTHER INFORMATION: peptide linked 6 aminohexanoic acid group
<221> NAME/KEY: MOD_RES
<222> LOCATION: (23)..(23)
<223> OTHER INFORMATION: AMIDATION

<400> SEQUENCE: 28

Ala Glu Gly Thr Gly Ser Trp Lys Val Cys Asp His Phe Phe Cys Leu
1               5                   10                  15

Ser Pro Ala Pro Glu Xaa Lys
            20

<210> SEQ ID NO 29
<211> LENGTH: 23
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MISC_FEATURE
<222> LOCATION: (22)..(22)
<223> OTHER INFORMATION: peptide linked 6 aminohexanoic acid group
<221> NAME/KEY: MOD_RES
<222> LOCATION: (23)..(23)
<223> OTHER INFORMATION: AMIDATION

<400> SEQUENCE: 29

Ala Glu Gly Thr Gly Ser Asn His Gly Cys Trp His Phe Ser Cys Ile
1               5                   10                  15

Trp Asp Ala Pro Glu Xaa Lys
            20

<210> SEQ ID NO 30
<211> LENGTH: 29
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (29)..(29)
<223> OTHER INFORMATION: AMIDATION

<400> SEQUENCE: 30

Ala Glu Gly Thr Gly Ser Phe Arg Asn Cys Glu Pro Trp Met Leu Arg
1               5                   10                  15

Phe Gly Cys Asn Pro Arg Ala Pro Glu Gly Gly Gly Lys
            20                  25

<210> SEQ ID NO 31
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
```

```
<223> OTHER INFORMATION: AMIDATION

<400> SEQUENCE: 31

Ala Glu Gly Thr Gly Asp Ala Asp Phe Cys Glu Gly Lys Asp Met Ile
1               5                   10                  15

Asp Trp Val Tyr Cys Arg Leu Tyr Asp Pro Glu Gly Gly Lys
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: AMIDATION

<400> SEQUENCE: 32

Ala Glu Gly Thr Gly Asp Phe Trp Phe Cys Asp Arg Ile Ala Trp Tyr
1               5                   10                  15

Pro Gln His Leu Cys Glu Phe Leu Asp Pro Glu Gly Gly Lys
            20                  25                  30

<210> SEQ ID NO 33
<211> LENGTH: 29
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MISC_FEATURE
<222> LOCATION: (28)..(28)
<223> OTHER INFORMATION: peptide linked 6 aminohexanoic acid group
<221> NAME/KEY: MOD_RES
<222> LOCATION: (29)..(29)
<223> OTHER INFORMATION: AMIDATION

<400> SEQUENCE: 33

Ala Glu Gly Thr Gly Asp Asp Trp Asp Cys Val Thr Arg Trp Ala Asn
1               5                   10                  15

Arg Asp Gln Gln Cys Trp Gly Pro Asp Pro Glu Xaa Lys
            20                  25

<210> SEQ ID NO 34
<211> LENGTH: 29
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MISC_FEATURE
<222> LOCATION: (28)..(28)
<223> OTHER INFORMATION: peptide linked 6 aminohexanoic acid group
<221> NAME/KEY: MOD_RES
<222> LOCATION: (29)..(29)
<223> OTHER INFORMATION: AMIDATION

<400> SEQUENCE: 34

Ala Glu Gly Thr Gly Asp Asp Trp Asp Cys Val Thr Arg Trp Ala Asn
1               5                   10                  15
```

Arg Asp Gln Gln Cys Trp Ala Leu Asp Pro Glu Xaa Lys
            20                  25

<210> SEQ ID NO 35
<211> LENGTH: 29
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MISC_FEATURE
<222> LOCATION: (28)..(28)
<223> OTHER INFORMATION: peptide linked 6 aminohexanoic acid group
<221> NAME/KEY: MOD_RES
<222> LOCATION: (29)..(29)
<223> OTHER INFORMATION: AMIDATION

<400> SEQUENCE: 35

Ala Glu Gly Thr Gly Asp Asp Trp Asp Cys Val Thr Asp Trp Ala Asn
1               5                   10                  15

Arg His Gln His Cys Trp Ala Leu Asp Pro Glu Xaa Lys
            20                  25

<210> SEQ ID NO 36
<211> LENGTH: 29
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MISC_FEATURE
<222> LOCATION: (28)..(28)
<223> OTHER INFORMATION: peptide linked 6 aminohexanoic acid group
<221> NAME/KEY: MOD_RES
<222> LOCATION: (29)..(29)
<223> OTHER INFORMATION: AMIDATION

<400> SEQUENCE: 36

Ala Glu Gly Thr Gly Asp Asp Trp Gln Cys Val Lys Asp Trp Ala Asn
1               5                   10                  15

Arg Arg Arg Gly Cys Met Ala Asp Asp Pro Glu Xaa Lys
            20                  25

<210> SEQ ID NO 37
<211> LENGTH: 29
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MISC_FEATURE
<222> LOCATION: (28)..(28)
<223> OTHER INFORMATION: peptide linked 6 aminohexanoic acid group
<221> NAME/KEY: MOD_RES
<222> LOCATION: (29)..(29)
<223> OTHER INFORMATION: AMIDATION

<400> SEQUENCE: 37

Ala Glu Gly Thr Gly Asp Arg Asn Met Cys Lys Phe Ser Trp Ile Arg
1               5                   10                  15

Ser Pro Ala Phe Cys Ala Arg Ala Asp Pro Glu Xaa Lys
            20                  25

```
<210> SEQ ID NO 38
<211> LENGTH: 10
<212> TYPE: PRT
<213> ORGANISM: Artificial Sequence
<220> FEATURE:
<223> OTHER INFORMATION: cytochrome c fragment
<221> NAME/KEY: MOD_RES
<222> LOCATION: (10)..(10)
<223> OTHER INFORMATION: AMIDATION
<221> NAME/KEY: MISC_FEATURE
<222> LOCATION: (1)..(1)
<223> OTHER INFORMATION: peptide linked 6 aminohexanoic acid group

<400> SEQUENCE: 38

Xaa Gly Ala Gln Gly His Thr Val Glu Lys
1               5                   10

<210> SEQ ID NO 39
<211> LENGTH: 25
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (25)..(25)
<223> OTHER INFORMATION: AMIDATION

<400> SEQUENCE: 39

Phe Trp Phe Cys Asp Arg Ile Ala Trp Tyr Pro Gln His Leu Cys Glu
1               5                   10                  15

Phe Leu Asp Pro Glu Gly Gly Gly Lys
            20                  25

<210> SEQ ID NO 40
<211> LENGTH: 22
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (22)..(22)
<223> OTHER INFORMATION: AMIDATION

<400> SEQUENCE: 40

Cys Asp Arg Ile Ala Trp Tyr Pro Gln His Leu Cys Glu Phe Leu Asp
1               5                   10                  15

Pro Glu Gly Gly Gly Lys
            20

<210> SEQ ID NO 41
<211> LENGTH: 28
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (28)..(28)
<223> OTHER INFORMATION: AMIDATION

<400> SEQUENCE: 41

Ala Glu Gly Thr Gly Asp Phe Trp Phe Cys Asp Arg Ile Ala Trp Tyr
```

```
                1               5              10              15
Pro Gln His Leu Cys Glu Phe Leu Gly Gly Gly Lys
                               20              25

<210> SEQ ID NO 42
<211> LENGTH: 25
<212> TYPE: PRT
<213> ORGANISM: Artificial Sequence
<220> FEATURE:
<223> OTHER INFORMATION: variegated display library template
<221> NAME/KEY: MOD_RES
<222> LOCATION: (1)..(1)
<223> OTHER INFORMATION: ACETYLATION
<221> NAME/KEY: MOD_RES
<222> LOCATION: (25)..(25)
<223> OTHER INFORMATION: AMIDATION

<400> SEQUENCE: 42

Ala Glu Gly Thr Gly Asp Phe Trp Phe Cys Asp Arg Ile Ala Trp Tyr
1               5                   10                  15
Pro Gln His Leu Cys Gly Gly Gly Lys
                20              25

<210> SEQ ID NO 43
<211> LENGTH: 16
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (16)..(16)
<223> OTHER INFORMATION: AMIDATION

<400> SEQUENCE: 43

Cys Asp Arg Ile Ala Trp Tyr Pro Gln His Leu Cys Gly Gly Gly Lys
1               5                   10                  15

<210> SEQ ID NO 44
<211> LENGTH: 14
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (14)..(14)
<223> OTHER INFORMATION: AMIDATION

<400> SEQUENCE: 44

Asp Arg Ile Ala Trp Tyr Pro Gln His Leu Gly Gly Gly Lys
1               5                   10

<210> SEQ ID NO 45
<211> LENGTH: 9
<212> TYPE: PRT
<213> ORGANISM: Artificial Sequence
<220> FEATURE:
<223> OTHER INFORMATION: cytochrome c fragment

<400> SEQUENCE: 45

Gly Ala Gln Gly His Thr Val Glu Lys
1               5
```

<210> SEQ ID NO 46
<211> LENGTH: 16
<212> TYPE: PRT
<213> ORGANISM: Artificial Sequence
<220> FEATURE:
<223> OTHER INFORMATION: albumin binding peptide

<400> SEQUENCE: 46

Phe Arg Asn Cys Glu Pro Trp Met Leu Arg Phe Gly Cys Asn Pro Arg
1               5                   10                  15

<210> SEQ ID NO 47
<211> LENGTH: 25
<212> TYPE: PRT
<213> ORGANISM: Artificial Sequence
<220> FEATURE:
<223> OTHER INFORMATION: albumin binding peptide

<400> SEQUENCE: 47

Ala Glu Gly Thr Gly Ser Phe Arg Asn Cys Glu Pro Trp Met Leu Arg
1               5                   10                  15

Phe Gly Cys Asn Pro Arg Ala Pro Glu
            20                  25

<210> SEQ ID NO 48
<211> LENGTH: 12
<212> TYPE: PRT
<213> ORGANISM: Artificial Sequence
<220> FEATURE:
<223> OTHER INFORMATION: albumin binding peptide

<400> SEQUENCE: 48

Val Ala Trp Cys Thr Ile Phe Leu Cys Leu Asp Val
1               5                   10

<210> SEQ ID NO 49
<211> LENGTH: 12
<212> TYPE: PRT
<213> ORGANISM: Artificial Sequence
<220> FEATURE:
<223> OTHER INFORMATION: albumin binding peptide

<400> SEQUENCE: 49

Phe Lys Ile Cys Asp Gln Trp Phe Cys Leu Met Pro
1               5                   10

<210> SEQ ID NO 50
<211> LENGTH: 12
<212> TYPE: PRT
<213> ORGANISM: Artificial Sequence
<220> FEATURE:
<223> OTHER INFORMATION: albumin binding peptide

<400> SEQUENCE: 50

His Val Gly Cys Asn Asn Ala Leu Cys Met Gln Tyr
1               5                   10

<210> SEQ ID NO 51
<211> LENGTH: 12
<212> TYPE: PRT
<213> ORGANISM: Artificial Sequence
<220> FEATURE:
<223> OTHER INFORMATION: albumin binding peptide

<400> SEQUENCE: 51

Trp Lys Val Cys Asp His Phe Phe Cys Leu Ser Pro
1               5                   10

```
<210> SEQ ID NO 52
<211> LENGTH: 12
<212> TYPE: PRT
<213> ORGANISM: Artificial Sequence
<220> FEATURE:
<223> OTHER INFORMATION: albumin binding peptide

<400> SEQUENCE: 52

Asn His Gly Cys Trp His Phe Ser Cys Ile Trp Asp
1               5                   10

<210> SEQ ID NO 53
<211> LENGTH: 21
<212> TYPE: PRT
<213> ORGANISM: Artificial Sequence
<220> FEATURE:
<223> OTHER INFORMATION: albumin binding peptide

<400> SEQUENCE: 53

Ala Glu Gly Thr Gly Ser Val Ala Trp Cys Thr Ile Phe Leu Cys Leu
1               5                   10                  15

Asp Val Ala Pro Glu
            20

<210> SEQ ID NO 54
<211> LENGTH: 21
<212> TYPE: PRT
<213> ORGANISM: Artificial Sequence
<220> FEATURE:
<223> OTHER INFORMATION: albumin binding peptide

<400> SEQUENCE: 54

Ala Glu Gly Thr Gly Ser Phe Lys Ile Cys Asp Gln Trp Phe Cys Leu
1               5                   10                  15

Met Pro Ala Pro Glu
            20

<210> SEQ ID NO 55
<211> LENGTH: 21
<212> TYPE: PRT
<213> ORGANISM: Artificial Sequence
<220> FEATURE:
<223> OTHER INFORMATION: albumin binding peptide

<400> SEQUENCE: 55

Ala Glu Gly Thr Gly Ser His Val Gly Cys Asn Asn Ala Leu Cys Met
1               5                   10                  15

Gln Tyr Ala Pro Glu
            20

<210> SEQ ID NO 56
<211> LENGTH: 21
<212> TYPE: PRT
<213> ORGANISM: Artificial Sequence
<220> FEATURE:
<223> OTHER INFORMATION: albumin binding peptide

<400> SEQUENCE: 56

Ala Glu Gly Thr Gly Ser Trp Lys Val Cys Asp His Phe Phe Cys Leu
1               5                   10                  15

Ser Pro Ala Pro Glu
            20
```

```
<210> SEQ ID NO 57
<211> LENGTH: 21
<212> TYPE: PRT
<213> ORGANISM: Artificial Sequence
<220> FEATURE:
<223> OTHER INFORMATION: albumin binding peptide

<400> SEQUENCE: 57

Ala Glu Gly Thr Gly Ser Asn His Gly Cys Trp His Phe Ser Cys Ile
1               5                   10                  15

Trp Asp Ala Pro Glu
            20

<210> SEQ ID NO 58
<211> LENGTH: 18
<212> TYPE: PRT
<213> ORGANISM: Artificial Sequence
<220> FEATURE:
<223> OTHER INFORMATION: albumin binding peptide

<400> SEQUENCE: 58

Ala Asp Phe Cys Glu Gly Lys Asp Met Ile Asp Trp Val Tyr Cys Arg
1               5                   10                  15

Leu Tyr

<210> SEQ ID NO 59
<211> LENGTH: 18
<212> TYPE: PRT
<213> ORGANISM: Artificial Sequence
<220> FEATURE:
<223> OTHER INFORMATION: albumin binding peptide

<400> SEQUENCE: 59

Phe Trp Phe Cys Asp Arg Ile Ala Trp Tyr Pro Gln His Leu Cys Glu
1               5                   10                  15

Phe Leu

<210> SEQ ID NO 60
<211> LENGTH: 18
<212> TYPE: PRT
<213> ORGANISM: Artificial Sequence
<220> FEATURE:
<223> OTHER INFORMATION: albumin binding peptide

<400> SEQUENCE: 60

Asp Trp Asp Cys Val Thr Arg Trp Ala Asn Arg Asp Gln Gln Cys Trp
1               5                   10                  15

Gly Pro

<210> SEQ ID NO 61
<211> LENGTH: 18
<212> TYPE: PRT
<213> ORGANISM: Artificial Sequence
<220> FEATURE:
<223> OTHER INFORMATION: albumin binding peptide

<400> SEQUENCE: 61

Asp Trp Asp Cys Val Thr Arg Trp Ala Asn Arg Asp Gln Gln Cys Trp
1               5                   10                  15

Ala Leu

<210> SEQ ID NO 62
<211> LENGTH: 18
<212> TYPE: PRT
```

```
<213> ORGANISM: Artificial Sequence
<220> FEATURE:
<223> OTHER INFORMATION: albumin binding peptide

<400> SEQUENCE: 62

Asp Trp Asp Cys Val Thr Asp Trp Ala Asn Arg His Gln His Cys Trp
1               5                   10                  15
Ala Leu

<210> SEQ ID NO 63
<211> LENGTH: 18
<212> TYPE: PRT
<213> ORGANISM: Artificial Sequence
<220> FEATURE:
<223> OTHER INFORMATION: albumin binding peptide

<400> SEQUENCE: 63

Asp Trp Gln Cys Val Lys Asp Trp Ala Asn Arg Arg Arg Gly Cys Met
1               5                   10                  15
Ala Asp

<210> SEQ ID NO 64
<211> LENGTH: 18
<212> TYPE: PRT
<213> ORGANISM: Artificial Sequence
<220> FEATURE:
<223> OTHER INFORMATION: albumin binding peptide

<400> SEQUENCE: 64

Arg Asn Met Cys Lys Phe Ser Trp Ile Arg Ser Pro Ala Phe Cys Ala
1               5                   10                  15
Arg Ala

<210> SEQ ID NO 65
<211> LENGTH: 27
<212> TYPE: PRT
<213> ORGANISM: Artificial Sequence
<220> FEATURE:
<223> OTHER INFORMATION: albumin binding peptide

<400> SEQUENCE: 65

Ala Glu Gly Thr Gly Asp Ala Asp Phe Cys Glu Gly Lys Asp Met Ile
1               5                   10                  15
Asp Trp Val Tyr Cys Arg Leu Tyr Asp Pro Glu
            20                  25

<210> SEQ ID NO 66
<211> LENGTH: 27
<212> TYPE: PRT
<213> ORGANISM: Artificial Sequence
<220> FEATURE:
<223> OTHER INFORMATION: albumin binding peptide

<400> SEQUENCE: 66

Ala Glu Gly Thr Gly Asp Phe Trp Phe Cys Asp Arg Ile Ala Trp Tyr
1               5                   10                  15
Pro Gln His Leu Cys Glu Phe Leu Asp Pro Glu
            20                  25

<210> SEQ ID NO 67
<211> LENGTH: 27
<212> TYPE: PRT
<213> ORGANISM: Artificial Sequence
<220> FEATURE:
<223> OTHER INFORMATION: albumin binding peptide
```

<400> SEQUENCE: 67

Ala Glu Gly Thr Gly Asp Asp Trp Asp Cys Val Thr Arg Trp Ala Asn
1               5                   10                  15

Arg Asp Gln Gln Cys Trp Gly Pro Asp Pro Glu
            20                  25

<210> SEQ ID NO 68
<211> LENGTH: 27
<212> TYPE: PRT
<213> ORGANISM: Artificial Sequence
<220> FEATURE:
<223> OTHER INFORMATION: albumin binding peptide

<400> SEQUENCE: 68

Ala Glu Gly Thr Gly Asp Asp Trp Asp Cys Val Thr Arg Trp Ala Asn
1               5                   10                  15

Arg Asp Gln Gln Cys Trp Ala Leu Asp Pro Glu
            20                  25

<210> SEQ ID NO 69
<211> LENGTH: 27
<212> TYPE: PRT
<213> ORGANISM: Artificial Sequence
<220> FEATURE:
<223> OTHER INFORMATION: albumin binding peptide

<400> SEQUENCE: 69

Ala Glu Gly Thr Gly Asp Asp Trp Asp Cys Val Thr Asp Trp Ala Asn
1               5                   10                  15

Arg His Gln His Cys Trp Ala Leu Asp Pro Glu
            20                  25

<210> SEQ ID NO 70
<211> LENGTH: 27
<212> TYPE: PRT
<213> ORGANISM: Artificial Sequence
<220> FEATURE:
<223> OTHER INFORMATION: albumin binding peptide

<400> SEQUENCE: 70

Ala Glu Gly Thr Gly Asp Asp Trp Gln Cys Val Lys Asp Trp Ala Asn
1               5                   10                  15

Arg Arg Arg Gly Cys Met Ala Asp Asp Pro Glu
            20                  25

<210> SEQ ID NO 71
<211> LENGTH: 27
<212> TYPE: PRT
<213> ORGANISM: Artificial Sequence
<220> FEATURE:
<223> OTHER INFORMATION: albumin binding peptide

<400> SEQUENCE: 71

Ala Glu Gly Thr Gly Asp Arg Asn Met Cys Lys Phe Ser Trp Ile Arg
1               5                   10                  15

Ser Pro Ala Phe Cys Ala Arg Ala Asp Pro Glu
            20                  25

<210> SEQ ID NO 72
<211> LENGTH: 12
<212> TYPE: PRT
<213> ORGANISM: Artificial Sequence
<220> FEATURE:

<223> OTHER INFORMATION: albumin binding peptide

<400> SEQUENCE: 72

Cys Asp Arg Ile Ala Trp Tyr Pro Gln His Ala Cys
1               5                   10

<210> SEQ ID NO 73
<211> LENGTH: 12
<212> TYPE: PRT
<213> ORGANISM: Artificial Sequence
<220> FEATURE:
<223> OTHER INFORMATION: albumin binding peptide

<400> SEQUENCE: 73

Cys Asp Arg Ile Ala Trp Tyr Pro Gln Ala Leu Cys
1               5                   10

<210> SEQ ID NO 74
<211> LENGTH: 12
<212> TYPE: PRT
<213> ORGANISM: Artificial Sequence
<220> FEATURE:
<223> OTHER INFORMATION: albumin binding peptide

<400> SEQUENCE: 74

Cys Asp Arg Ile Ala Trp Tyr Pro Ala His Leu Cys
1               5                   10

<210> SEQ ID NO 75
<211> LENGTH: 12
<212> TYPE: PRT
<213> ORGANISM: Artificial Sequence
<220> FEATURE:
<223> OTHER INFORMATION: albumin binding peptide

<400> SEQUENCE: 75

Cys Asp Arg Ile Ala Trp Tyr Ala Gln His Leu Cys
1               5                   10

<210> SEQ ID NO 76
<211> LENGTH: 12
<212> TYPE: PRT
<213> ORGANISM: Artificial Sequence
<220> FEATURE:
<223> OTHER INFORMATION: albumin binding peptide

<400> SEQUENCE: 76

Cys Asp Arg Ile Ala Trp Ala Pro Gln His Leu Cys
1               5                   10

<210> SEQ ID NO 77
<211> LENGTH: 12
<212> TYPE: PRT
<213> ORGANISM: Artificial Sequence
<220> FEATURE:
<223> OTHER INFORMATION: albumin binding peptide

<400> SEQUENCE: 77

Cys Asp Arg Ile Ala Ala Tyr Pro Gln His Leu Cys
1               5                   10

<210> SEQ ID NO 78
<211> LENGTH: 12
<212> TYPE: PRT
<213> ORGANISM: Artificial Sequence
<220> FEATURE:
<223> OTHER INFORMATION: albumin binding peptide

```
<400> SEQUENCE: 78

Cys Asp Arg Ala Ala Trp Tyr Pro Gln His Leu Cys
1               5                   10

<210> SEQ ID NO 79
<211> LENGTH: 12
<212> TYPE: PRT
<213> ORGANISM: Artificial Sequence
<220> FEATURE:
<223> OTHER INFORMATION: albumin binding peptide

<400> SEQUENCE: 79

Cys Asp Ala Ile Ala Trp Tyr Pro Gln His Leu Cys
1               5                   10

<210> SEQ ID NO 80
<211> LENGTH: 12
<212> TYPE: PRT
<213> ORGANISM: Artificial Sequence
<220> FEATURE:
<223> OTHER INFORMATION: albumin binding peptide

<400> SEQUENCE: 80

Cys Ala Arg Ile Ala Trp Tyr Pro Gln His Leu Cys
1               5                   10

<210> SEQ ID NO 81
<211> LENGTH: 18
<212> TYPE: PRT
<213> ORGANISM: Artificial Sequence
<220> FEATURE:
<223> OTHER INFORMATION: albumin binding peptide

<400> SEQUENCE: 81

Phe Trp Phe Cys Asp Arg Ile Ala Trp Tyr Pro Gln His Leu Cys Glu
1               5                   10                  15

Phe Ala

<210> SEQ ID NO 82
<211> LENGTH: 18
<212> TYPE: PRT
<213> ORGANISM: Artificial Sequence
<220> FEATURE:
<223> OTHER INFORMATION: albumin binding peptide

<400> SEQUENCE: 82

Phe Trp Phe Cys Asp Arg Ile Ala Trp Tyr Pro Gln His Leu Cys Glu
1               5                   10                  15

Ala Leu

<210> SEQ ID NO 83
<211> LENGTH: 18
<212> TYPE: PRT
<213> ORGANISM: Artificial Sequence
<220> FEATURE:
<223> OTHER INFORMATION: albumin binding peptide

<400> SEQUENCE: 83

Phe Trp Phe Cys Asp Arg Ile Ala Trp Tyr Pro Gln His Leu Cys Ala
1               5                   10                  15

Phe Leu

<210> SEQ ID NO 84
```

```
<211> LENGTH: 18
<212> TYPE: PRT
<213> ORGANISM: Artificial Sequence
<220> FEATURE:
<223> OTHER INFORMATION: albumin binding peptide

<400> SEQUENCE: 84

Phe Trp Phe Cys Asp Arg Ile Ala Trp Tyr Pro Gln His Ala Cys Glu
1               5                   10                  15

Phe Leu

<210> SEQ ID NO 85
<211> LENGTH: 18
<212> TYPE: PRT
<213> ORGANISM: Artificial Sequence
<220> FEATURE:
<223> OTHER INFORMATION: albumin binding peptide

<400> SEQUENCE: 85

Phe Trp Phe Cys Asp Arg Ile Ala Trp Tyr Pro Gln Ala Leu Cys Glu
1               5                   10                  15

Phe Leu

<210> SEQ ID NO 86
<211> LENGTH: 18
<212> TYPE: PRT
<213> ORGANISM: Artificial Sequence
<220> FEATURE:
<223> OTHER INFORMATION: albumin binding peptide

<400> SEQUENCE: 86

Phe Trp Phe Cys Asp Arg Ile Ala Trp Tyr Pro Ala His Leu Cys Glu
1               5                   10                  15

Phe Leu

<210> SEQ ID NO 87
<211> LENGTH: 18
<212> TYPE: PRT
<213> ORGANISM: Artificial Sequence
<220> FEATURE:
<223> OTHER INFORMATION: albumin binding peptide

<400> SEQUENCE: 87

Phe Trp Phe Cys Asp Arg Ile Ala Trp Tyr Ala Gln His Leu Cys Glu
1               5                   10                  15

Phe Leu

<210> SEQ ID NO 88
<211> LENGTH: 18
<212> TYPE: PRT
<213> ORGANISM: Artificial Sequence
<220> FEATURE:
<223> OTHER INFORMATION: albumin binding peptide

<400> SEQUENCE: 88

Phe Trp Phe Cys Asp Arg Ile Ala Trp Ala Pro Gln His Leu Cys Glu
1               5                   10                  15

Phe Leu

<210> SEQ ID NO 89
<211> LENGTH: 18
<212> TYPE: PRT
<213> ORGANISM: Artificial Sequence
<220> FEATURE:
```

<223> OTHER INFORMATION: albumin binding peptide

<400> SEQUENCE: 89

Phe Trp Phe Cys Asp Arg Ile Ala Ala Tyr Pro Gln His Leu Cys Glu
1               5                   10                  15
Phe Leu

<210> SEQ ID NO 90
<211> LENGTH: 18
<212> TYPE: PRT
<213> ORGANISM: Artificial Sequence
<220> FEATURE:
<223> OTHER INFORMATION: albumin binding peptide

<400> SEQUENCE: 90

Phe Trp Phe Cys Asp Arg Ala Ala Trp Tyr Pro Gln His Leu Cys Glu
1               5                   10                  15
Phe Leu

<210> SEQ ID NO 91
<211> LENGTH: 18
<212> TYPE: PRT
<213> ORGANISM: Artificial Sequence
<220> FEATURE:
<223> OTHER INFORMATION: albumin binding peptide

<400> SEQUENCE: 91

Phe Trp Phe Cys Asp Ala Ile Ala Trp Tyr Pro Gln His Leu Cys Glu
1               5                   10                  15
Phe Leu

<210> SEQ ID NO 92
<211> LENGTH: 18
<212> TYPE: PRT
<213> ORGANISM: Artificial Sequence
<220> FEATURE:
<223> OTHER INFORMATION: albumin binding peptide

<400> SEQUENCE: 92

Phe Trp Phe Cys Ala Arg Ile Ala Trp Tyr Pro Gln His Leu Cys Glu
1               5                   10                  15
Phe Leu

<210> SEQ ID NO 93
<211> LENGTH: 18
<212> TYPE: PRT
<213> ORGANISM: Artificial Sequence
<220> FEATURE:
<223> OTHER INFORMATION: albumin binding peptide

<400> SEQUENCE: 93

Phe Trp Ala Cys Asp Arg Ile Ala Trp Tyr Pro Gln His Leu Cys Glu
1               5                   10                  15
Phe Leu

<210> SEQ ID NO 94
<211> LENGTH: 18
<212> TYPE: PRT
<213> ORGANISM: Artificial Sequence
<220> FEATURE:
<223> OTHER INFORMATION: albumin binding peptide

<400> SEQUENCE: 94

```
Phe Ala Phe Cys Asp Arg Ile Ala Trp Tyr Pro Gln His Leu Cys Glu
 1               5                  10                  15

Phe Leu

<210> SEQ ID NO 95
<211> LENGTH: 18
<212> TYPE: PRT
<213> ORGANISM: Artificial Sequence
<220> FEATURE:
<223> OTHER INFORMATION: albumin binding peptide

<400> SEQUENCE: 95

Ala Trp Phe Cys Asp Arg Ile Ala Trp Tyr Pro Gln His Leu Cys Glu
 1               5                  10                  15
Phe Leu

<210> SEQ ID NO 96
<211> LENGTH: 27
<212> TYPE: PRT
<213> ORGANISM: Artificial Sequence
<220> FEATURE:
<223> OTHER INFORMATION: albumin binding peptide

<400> SEQUENCE: 96

Ala Glu Gly Thr Gly Asp Phe Trp Phe Cys Asp Arg Ile Ala Trp Tyr
 1               5                  10                  15

Pro Gln His Leu Cys Glu Phe Leu Ala Pro Glu
            20                  25

<210> SEQ ID NO 97
<211> LENGTH: 27
<212> TYPE: PRT
<213> ORGANISM: Artificial Sequence
<220> FEATURE:
<223> OTHER INFORMATION: albumin binding peptide

<400> SEQUENCE: 97

Ala Glu Gly Thr Gly Asp Phe Trp Phe Cys Asp Arg Ile Ala Trp Tyr
 1               5                  10                  15

Pro Gln His Leu Cys Glu Phe Ala Asp Pro Glu
            20                  25

<210> SEQ ID NO 98
<211> LENGTH: 27
<212> TYPE: PRT
<213> ORGANISM: Artificial Sequence
<220> FEATURE:
<223> OTHER INFORMATION: albumin binding peptide

<400> SEQUENCE: 98

Ala Glu Gly Thr Gly Asp Phe Trp Phe Cys Asp Arg Ile Ala Trp Tyr
 1               5                  10                  15

Pro Gln His Leu Cys Glu Ala Leu Asp Pro Glu
            20                  25

<210> SEQ ID NO 99
<211> LENGTH: 27
<212> TYPE: PRT
<213> ORGANISM: Artificial Sequence
<220> FEATURE:
<223> OTHER INFORMATION: albumin binding peptide

<400> SEQUENCE: 99

Ala Glu Gly Thr Gly Asp Phe Trp Phe Cys Asp Arg Ile Ala Trp Tyr
 1               5                  10                  15
```

```
Pro Gln His Leu Cys Ala Phe Leu Asp Pro Glu
            20                  25

<210> SEQ ID NO 100
<211> LENGTH: 27
<212> TYPE: PRT
<213> ORGANISM: Artificial Sequence
<220> FEATURE:
<223> OTHER INFORMATION: albumin binding peptide

<400> SEQUENCE: 100

Ala Glu Gly Thr Gly Asp Phe Trp Phe Cys Asp Arg Ile Ala Trp Tyr
1               5                   10                  15

Pro Gln His Ala Cys Glu Phe Leu Asp Pro Glu
            20                  25

<210> SEQ ID NO 101
<211> LENGTH: 27
<212> TYPE: PRT
<213> ORGANISM: Artificial Sequence
<220> FEATURE:
<223> OTHER INFORMATION: albumin binding peptide

<400> SEQUENCE: 101

Ala Glu Gly Thr Gly Asp Phe Trp Phe Cys Asp Arg Ile Ala Trp Tyr
1               5                   10                  15

Pro Gln Ala Leu Cys Glu Phe Leu Asp Pro Glu
            20                  25

<210> SEQ ID NO 102
<211> LENGTH: 27
<212> TYPE: PRT
<213> ORGANISM: Artificial Sequence
<220> FEATURE:
<223> OTHER INFORMATION: albumin binding peptide

<400> SEQUENCE: 102

Ala Glu Gly Thr Gly Asp Phe Trp Phe Cys Asp Arg Ile Ala Trp Tyr
1               5                   10                  15

Pro Ala His Leu Cys Glu Phe Leu Asp Pro Glu
            20                  25

<210> SEQ ID NO 103
<211> LENGTH: 27
<212> TYPE: PRT
<213> ORGANISM: Artificial Sequence
<220> FEATURE:
<223> OTHER INFORMATION: albumin binding peptide

<400> SEQUENCE: 103

Ala Glu Gly Thr Gly Asp Phe Trp Phe Cys Asp Arg Ile Ala Trp Tyr
1               5                   10                  15

Ala Gln His Leu Cys Glu Phe Leu Asp Pro Glu
            20                  25

<210> SEQ ID NO 104
<211> LENGTH: 27
<212> TYPE: PRT
<213> ORGANISM: Artificial Sequence
<220> FEATURE:
<223> OTHER INFORMATION: albumin binding peptide

<400> SEQUENCE: 104

Ala Glu Gly Thr Gly Asp Phe Trp Phe Cys Asp Arg Ile Ala Trp Ala
```

```
              1               5              10              15

Pro Gln His Leu Cys Glu Phe Leu Asp Pro Glu
            20                  25

<210> SEQ ID NO 105
<211> LENGTH: 27
<212> TYPE: PRT
<213> ORGANISM: Artificial Sequence
<220> FEATURE:
<223> OTHER INFORMATION: albumin binding peptide

<400> SEQUENCE: 105

Ala Glu Gly Thr Gly Asp Phe Trp Phe Cys Asp Arg Ile Ala Ala Tyr
1               5                  10                  15

Pro Gln His Leu Cys Glu Phe Leu Asp Pro Glu
            20                  25

<210> SEQ ID NO 106
<211> LENGTH: 27
<212> TYPE: PRT
<213> ORGANISM: Artificial Sequence
<220> FEATURE:
<223> OTHER INFORMATION: albumin binding peptide

<400> SEQUENCE: 106

Ala Glu Gly Thr Gly Asp Phe Trp Phe Cys Asp Arg Ala Ala Trp Tyr
1               5                  10                  15

Pro Gln His Leu Cys Glu Phe Leu Asp Pro Glu
            20                  25

<210> SEQ ID NO 107
<211> LENGTH: 27
<212> TYPE: PRT
<213> ORGANISM: Artificial Sequence
<220> FEATURE:
<223> OTHER INFORMATION: albumin binding peptide

<400> SEQUENCE: 107

Ala Glu Gly Thr Gly Asp Phe Trp Phe Cys Asp Ala Ile Ala Trp Tyr
1               5                  10                  15

Pro Gln His Leu Cys Glu Phe Leu Asp Pro Glu
            20                  25

<210> SEQ ID NO 108
<211> LENGTH: 27
<212> TYPE: PRT
<213> ORGANISM: Artificial Sequence
<220> FEATURE:
<223> OTHER INFORMATION: albumin binding peptide

<400> SEQUENCE: 108

Ala Glu Gly Thr Gly Asp Phe Trp Phe Cys Ala Arg Ile Ala Trp Tyr
1               5                  10                  15

Pro Gln His Leu Cys Glu Phe Leu Asp Pro Glu
            20                  25

<210> SEQ ID NO 109
<211> LENGTH: 27
<212> TYPE: PRT
<213> ORGANISM: Artificial Sequence
<220> FEATURE:
<223> OTHER INFORMATION: albumin binding peptide

<400> SEQUENCE: 109
```

```
Ala Glu Gly Thr Gly Asp Phe Trp Ala Cys Asp Arg Ile Ala Trp Tyr
1               5                   10                  15

Pro Gln His Leu Cys Glu Phe Leu Asp Pro Glu
            20                  25
```

<210> SEQ ID NO 110
<211> LENGTH: 27
<212> TYPE: PRT
<213> ORGANISM: Artificial Sequence
<220> FEATURE:
<223> OTHER INFORMATION: albumin binding peptide

<400> SEQUENCE: 110

```
Ala Glu Gly Thr Gly Asp Phe Ala Phe Cys Asp Arg Ile Ala Trp Tyr
1               5                   10                  15

Pro Gln His Leu Cys Glu Phe Leu Asp Pro Glu
            20                  25
```

<210> SEQ ID NO 111
<211> LENGTH: 27
<212> TYPE: PRT
<213> ORGANISM: Artificial Sequence
<220> FEATURE:
<223> OTHER INFORMATION: albumin binding peptide

<400> SEQUENCE: 111

```
Ala Glu Gly Thr Gly Asp Ala Trp Phe Cys Asp Arg Ile Ala Trp Tyr
1               5                   10                  15

Pro Gln His Leu Cys Glu Phe Leu Asp Pro Glu
            20                  25
```

<210> SEQ ID NO 112
<211> LENGTH: 27
<212> TYPE: PRT
<213> ORGANISM: Artificial Sequence
<220> FEATURE:
<223> OTHER INFORMATION: albumin binding peptide

<400> SEQUENCE: 112

```
Ala Glu Gly Thr Gly Ala Phe Trp Phe Cys Asp Arg Ile Ala Trp Tyr
1               5                   10                  15

Pro Gln His Leu Cys Glu Phe Leu Asp Pro Glu
            20                  25
```

<210> SEQ ID NO 113
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: AMIDATION

<400> SEQUENCE: 113

```
Ala Glu Gly Thr Gly Asp Phe Trp Phe Cys Asp Arg Ile Ala Trp Tyr
1               5                   10                  15

Pro Gln His Leu Cys Glu Phe Leu Ala Pro Glu Gly Gly Gly Lys
            20                  25                  30
```

<210> SEQ ID NO 114
<211> LENGTH: 31

```
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: AMIDATION

<400> SEQUENCE: 114

Ala Glu Gly Thr Gly Asp Phe Trp Phe Cys Asp Arg Ile Ala Trp Tyr
1               5                   10                  15

Pro Gln His Leu Cys Glu Phe Ala Asp Pro Glu Gly Gly Gly Lys
            20                  25                  30

<210> SEQ ID NO 115
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: AMIDATION

<400> SEQUENCE: 115

Ala Glu Gly Thr Gly Asp Phe Trp Phe Cys Asp Arg Ile Ala Trp Tyr
1               5                   10                  15

Pro Gln His Leu Cys Glu Ala Leu Asp Pro Glu Gly Gly Gly Lys
            20                  25                  30

<210> SEQ ID NO 116
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: ACETYLATION

<400> SEQUENCE: 116

Ala Glu Gly Thr Gly Asp Phe Trp Phe Cys Asp Arg Ile Ala Trp Tyr
1               5                   10                  15

Pro Gln His Leu Cys Ala Phe Leu Asp Pro Glu Gly Gly Gly Lys
            20                  25                  30

<210> SEQ ID NO 117
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: AMIDATION

<400> SEQUENCE: 117
```

```
Ala Glu Gly Thr Gly Asp Phe Trp Phe Cys Asp Arg Ile Ala Trp Tyr
1               5                   10                  15

Pro Gln His Ala Cys Glu Phe Leu Asp Pro Glu Gly Gly Lys
            20                  25                  30

<210> SEQ ID NO 118
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: AMIDATION

<400> SEQUENCE: 118

Ala Glu Gly Thr Gly Asp Phe Trp Phe Cys Asp Arg Ile Ala Trp Tyr
1               5                   10                  15

Pro Gln Ala Leu Cys Glu Phe Leu Asp Pro Glu Gly Gly Lys
            20                  25                  30

<210> SEQ ID NO 119
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: AMIDATION

<400> SEQUENCE: 119

Ala Glu Gly Thr Gly Asp Phe Trp Phe Cys Asp Arg Ile Ala Trp Tyr
1               5                   10                  15

Pro Ala His Leu Cys Glu Phe Leu Asp Pro Glu Gly Gly Lys
            20                  25                  30

<210> SEQ ID NO 120
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: AMIDATION

<400> SEQUENCE: 120

Ala Glu Gly Thr Gly Asp Phe Trp Phe Cys Asp Arg Ile Ala Trp Tyr
1               5                   10                  15

Ala Gln His Leu Cys Glu Phe Leu Asp Pro Glu Gly Gly Lys
            20                  25                  30

<210> SEQ ID NO 121
<211> LENGTH: 31
<212> TYPE: PRT
<213> ORGANISM: Artificial Sequence
<220> FEATURE:
<223> OTHER INFORMATION: albumin binding peptide
```

```
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: AMIDATION

<400> SEQUENCE: 121

Ala Glu Gly Thr Gly Asp Phe Trp Phe Cys Asp Arg Ile Ala Trp Ala
1               5                   10                  15

Pro Gln His Leu Cys Glu Phe Leu Asp Pro Glu Gly Gly Lys
            20                  25                  30

<210> SEQ ID NO 122
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: AMIDATION

<400> SEQUENCE: 122

Ala Glu Gly Thr Gly Asp Phe Trp Phe Cys Asp Arg Ile Ala Ala Tyr
1               5                   10                  15

Pro Gln His Leu Cys Glu Phe Leu Asp Pro Glu Gly Gly Lys
            20                  25                  30

<210> SEQ ID NO 123
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: AMIDATION

<400> SEQUENCE: 123

Ala Glu Gly Thr Gly Asp Phe Trp Phe Cys Asp Arg Ala Ala Trp Tyr
1               5                   10                  15

Pro Gln His Leu Cys Glu Phe Leu Asp Pro Glu Gly Gly Lys
            20                  25                  30

<210> SEQ ID NO 124
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (1)..(1)
<223> OTHER INFORMATION: AMIDATION

<400> SEQUENCE: 124

Ala Glu Gly Thr Gly Asp Phe Trp Phe Cys Asp Ala Ile Ala Trp Tyr
1               5                   10                  15

Pro Gln His Leu Cys Glu Phe Leu Asp Pro Glu Gly Gly Gly Lys
```

20                  25                  30

<210> SEQ ID NO 125
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: AMIDATION

<400> SEQUENCE: 125

Ala Glu Gly Thr Gly Asp Phe Trp Phe Cys Ala Arg Ile Ala Trp Tyr
1               5                   10                  15

Pro Gln His Leu Cys Glu Phe Leu Asp Pro Glu Gly Gly Gly Lys
            20                  25                  30

<210> SEQ ID NO 126
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: AMIDATION

<400> SEQUENCE: 126

Ala Glu Gly Thr Gly Asp Phe Trp Ala Cys Asp Arg Ile Ala Trp Tyr
1               5                   10                  15

Pro Gln His Leu Cys Glu Phe Leu Asp Pro Glu Gly Gly Gly Lys
            20                  25                  30

<210> SEQ ID NO 127
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: AMIDATION

<400> SEQUENCE: 127

Ala Glu Gly Thr Gly Asp Phe Ala Phe Cys Asp Arg Ile Ala Trp Tyr
1               5                   10                  15

Pro Gln His Leu Cys Glu Phe Leu Asp Pro Glu Gly Gly Gly Lys
            20                  25                  30

<210> SEQ ID NO 128
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES

```
<222> LOCATION: (31)..(31)
<223> OTHER INFORMATION: AMIDATION

<400> SEQUENCE: 128

Ala Glu Gly Thr Gly Asp Ala Trp Phe Cys Asp Arg Ile Ala Trp Tyr
1               5                   10                  15
Pro Gln His Leu Cys Glu Phe Leu Asp Pro Glu Gly Gly Lys
            20                  25                  30

<210> SEQ ID NO 129
<211> LENGTH: 31
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (31)..(31)
<223> OTHER INFORMATION: AMIDATION

<400> SEQUENCE: 129

Ala Glu Gly Thr Gly Ala Phe Trp Phe Cys Asp Arg Ile Ala Trp Tyr
1               5                   10                  15
Pro Gln His Leu Cys Glu Phe Leu Asp Pro Glu Gly Gly Lys
            20                  25                  30

<210> SEQ ID NO 130
<211> LENGTH: 8
<212> TYPE: PRT
<213> ORGANISM: Artificial Sequence
<220> FEATURE:
<223> OTHER INFORMATION: albumin binding peptide
<221> NAME/KEY: MISC_FEATURE
<222> LOCATION: (2)..(2)
<223> OTHER INFORMATION: Ala, Leu, His, Met, Phe, Ser, or Thr
<221> NAME/KEY: MISC_FEATURE
<222> LOCATION: (3)..(3)
<223> OTHER INFORMATION: Ile, Phe, Pro, Ser, Trp, or Tyr
<221> NAME/KEY: MISC_FEATURE
<222> LOCATION: (4)..(4)
<223> OTHER INFORMATION: Asp, Gln, Glu, Lys, Pro, Trp, or Tyr
<221> NAME/KEY: MISC_FEATURE
<222> LOCATION: (5)..(5)
<223> OTHER INFORMATION: Asp, Gln, Gly, Leu, Pro, or Trp
<221> NAME/KEY: MISC_FEATURE
<222> LOCATION: (6)..(6)
<223> OTHER INFORMATION: Asp, Ile, Leu, Lys, Met, Pro, Trp, or Tyr
<221> NAME/KEY: MISC_FEATURE
<222> LOCATION: (7)..(7)
<223> OTHER INFORMATION: Gln, Gly, Ile, Phe, Thr, Trp, or Val

<400> SEQUENCE: 130

Cys Xaa Xaa Xaa Xaa Xaa Xaa Cys
1               5

<210> SEQ ID NO 131
<211> LENGTH: 14
<212> TYPE: PRT
<213> ORGANISM: Artificial Sequence
<220> FEATURE:
<223> OTHER INFORMATION: albumin binding peptide
<221> NAME/KEY: MISC_FEATURE
<222> LOCATION: (1)..(1)
<223> OTHER INFORMATION: Ala, Gln, Leu, Lys, Phe, Trp, or Tyr
<221> NAME/KEY: MISC_FEATURE
<222> LOCATION: (2)..(2)
<223> OTHER INFORMATION: Asn, Gln, Glu, Ile, Thr, or Trp
<221> NAME/KEY: MISC_FEATURE
<222> LOCATION: (3)..(3)
```

```
<223> OTHER INFORMATION: Asn, Gly, Phe, Thr, Trp, or Tyr
<221> NAME/KEY: MISC_FEATURE
<222> LOCATION: (5)..(5)
<223> OTHER INFORMATION: Ala, Leu, His, Met, Phe, Ser, or Thr
<221> NAME/KEY: MISC_FEATURE
<222> LOCATION: (6)..(6)
<223> OTHER INFORMATION: Ile, Phe, Pro, Ser, Trp, or Tyr
<221> NAME/KEY: MISC_FEATURE
<222> LOCATION: (7)..(7)
<223> OTHER INFORMATION: Asp, Gln, Glu, Lys, Pro, Trp, or Tyr
<221> NAME/KEY: MISC_FEATURE
<222> LOCATION: (8)..(8)
<223> OTHER INFORMATION: Asp, Gln, Gly, Leu, Pro, or Trp
<221> NAME/KEY: MISC_FEATURE
<222> LOCATION: (9)..(9)
<223> OTHER INFORMATION: Asp, Ile, Leu, Lys, Met, Pro, Trp, or Tyr
<221> NAME/KEY: MISC_FEATURE
<222> LOCATION: (10)..(10)
<223> OTHER INFORMATION: Gln, Gly, Ile, Phe, Thr, Trp, or Val
<221> NAME/KEY: MISC_FEATURE
<222> LOCATION: (12)..(12)
<223> OTHER INFORMATION: Asp, Glu, Gly, Leu, Lys, Pro, or Ser
<221> NAME/KEY: MISC_FEATURE
<222> LOCATION: (13)..(13)
<223> OTHER INFORMATION: Glu, His, Ile, Leu, Lys, Ser, Trp, or Val
<221> NAME/KEY: MISC_FEATURE
<222> LOCATION: (14)..(14)
<223> OTHER INFORMATION: Ala, Asn, His, Ile, Met, Phe, Pro, or Ser

<400> SEQUENCE: 131

Xaa Xaa Xaa Cys Xaa Xaa Xaa Xaa Xaa Xaa Cys Xaa Xaa Xaa
1               5                   10

<210> SEQ ID NO 132
<211> LENGTH: 18
<212> TYPE: PRT
<213> ORGANISM: Artificial Sequence
<220> FEATURE:
<223> OTHER INFORMATION: albumin binding peptide
<221> NAME/KEY: MISC_FEATURE
<222> LOCATION: (3)..(3)
<223> OTHER INFORMATION: Ala, Gln, Leu, Lys, Phe, Trp, or Tyr
<221> NAME/KEY: MISC_FEATURE
<222> LOCATION: (4)..(4)
<223> OTHER INFORMATION: Asn, Gln, Glu, Ile, Thr, or Trp
<221> NAME/KEY: MISC_FEATURE
<222> LOCATION: (5)..(5)
<223> OTHER INFORMATION: Asn, Gly, Phe, Thr, Trp, or Tyr
<221> NAME/KEY: MISC_FEATURE
<222> LOCATION: (7)..(7)
<223> OTHER INFORMATION: Ala, Leu, His, Met, Phe, Ser, or Thr
<221> NAME/KEY: MISC_FEATURE
<222> LOCATION: (8)..(8)
<223> OTHER INFORMATION: Ile, Phe, Pro, Ser, Trp, or Tyr
<221> NAME/KEY: MISC_FEATURE
<222> LOCATION: (9)..(9)
<223> OTHER INFORMATION: Asp, Gln, Glu, Lys, Pro, Trp, or Tyr
<221> NAME/KEY: MISC_FEATURE
<222> LOCATION: (10)..(10)
<223> OTHER INFORMATION: Asp, Gln, Gly, Leu, Pro, or Trp
<221> NAME/KEY: MISC_FEATURE
<222> LOCATION: (11)..(11)
<223> OTHER INFORMATION: Asp, Ile, Leu, Lys, Met, Pro, Trp, or Tyr
<221> NAME/KEY: MISC_FEATURE
<222> LOCATION: (12)..(12)
<223> OTHER INFORMATION: Gln, Gly, Ile, Phe, Thr, Trp, or Val
<221> NAME/KEY: MISC_FEATURE
<222> LOCATION: (14)..(14)
<223> OTHER INFORMATION: Asp, Glu, Gly, Leu, Lys, Pro, or Ser
<221> NAME/KEY: MISC_FEATURE
<222> LOCATION: (15)..(15)
<223> OTHER INFORMATION: Glu, His, Ile, Leu, Lys, Ser, Trp, or Val
<221> NAME/KEY: MISC_FEATURE
<222> LOCATION: (16)..(16)
<223> OTHER INFORMATION: Ala, Asn, His, Ile, Met, Phe, Pro, or Ser

<400> SEQUENCE: 132
```

Ala Gly Xaa Xaa Xaa Cys Xaa Xaa Xaa Xaa Xaa Xaa Cys Xaa Xaa Xaa
1               5                   10                  15

Gly Thr

<210> SEQ ID NO 133
<211> LENGTH: 10
<212> TYPE: PRT
<213> ORGANISM: Artificial Sequence
<220> FEATURE:
<223> OTHER INFORMATION: albumin binding peptide
<221> NAME/KEY: MISC_FEATURE
<222> LOCATION: (2)..(2)
<223> OTHER INFORMATION: Gln, Glu, Phe, or Met
<221> NAME/KEY: MISC_FEATURE
<222> LOCATION: (3)..(3)
<223> OTHER INFORMATION: Asp, Pro, or Thr
<221> NAME/KEY: MISC_FEATURE
<222> LOCATION: (4)..(4)
<223> OTHER INFORMATION: Ile, Ser, or Trp
<221> NAME/KEY: MISC_FEATURE
<222> LOCATION: (5)..(5)
<223> OTHER INFORMATION: His, Met, Phe or Pro
<221> NAME/KEY: MISC_FEATURE
<222> LOCATION: (6)..(6)
<223> OTHER INFORMATION: Asn, Leu, or Thr
<221> NAME/KEY: MISC_FEATURE
<222> LOCATION: (7)..(7)
<223> OTHER INFORMATION: Arg, Asn, His, or Thr
<221> NAME/KEY: MISC_FEATURE
<222> LOCATION: (8)..(8)
<223> OTHER INFORMATION: Arg, Met, Phe, or Tyr
<221> NAME/KEY: MISC_FEATURE
<222> LOCATION: (9)..(9)
<223> OTHER INFORMATION: Asp, Gly, Phe, or Trp

<400> SEQUENCE: 133

Cys Xaa Xaa Xaa Xaa Xaa Xaa Xaa Xaa Cys
1               5                   10

<210> SEQ ID NO 134
<211> LENGTH: 16
<212> TYPE: PRT
<213> ORGANISM: Artificial Sequence
<220> FEATURE:
<223> OTHER INFORMATION: albumin binding peptide
<221> NAME/KEY: MISC_FEATURE
<222> LOCATION: (1)..(1)
<223> OTHER INFORMATION: Arg, Phe, or Tyr
<221> NAME/KEY: MISC_FEATURE
<222> LOCATION: (2)..(2)
<223> OTHER INFORMATION: Arg, Leu, Ser, or Trp
<221> NAME/KEY: MISC_FEATURE
<222> LOCATION: (3)..(3)
<223> OTHER INFORMATION: Asn, Asp, Phe, or Tyr
<221> NAME/KEY: MISC_FEATURE
<222> LOCATION: (5)..(5)
<223> OTHER INFORMATION: Gln, Glu, Phe, or Met
<221> NAME/KEY: MISC_FEATURE
<222> LOCATION: (6)..(6)
<223> OTHER INFORMATION: Asp, Pro, or Thr
<221> NAME/KEY: MISC_FEATURE
<222> LOCATION: (7)..(7)
<223> OTHER INFORMATION: Ile, Ser, or Trp
<221> NAME/KEY: MISC_FEATURE
<222> LOCATION: (8)..(8)
<223> OTHER INFORMATION: His, Met, Phe or Pro
<221> NAME/KEY: MISC_FEATURE
<222> LOCATION: (9)..(9)
<223> OTHER INFORMATION: Asn, Leu, or Thr
<221> NAME/KEY: MISC_FEATURE
<222> LOCATION: (10)..(10)
<223> OTHER INFORMATION: Arg, Asn, His, or Thr
<221> NAME/KEY: MISC_FEATURE
<222> LOCATION: (11)..(11)

```
<223> OTHER INFORMATION: Arg, Met, Phe, or Tyr
<221> NAME/KEY: MISC_FEATURE
<222> LOCATION: (12)..(12)
<223> OTHER INFORMATION: Asp, Gly, Phe, or Trp
<221> NAME/KEY: MISC_FEATURE
<222> LOCATION: (14)..(14)
<223> OTHER INFORMATION: Ala, Asn, or Asp
<221> NAME/KEY: MISC_FEATURE
<222> LOCATION: (15)..(15)
<223> OTHER INFORMATION: Arg, Phe, Pro, or Tyr
<221> NAME/KEY: MISC_FEATURE
<222> LOCATION: (16)..(16)
<223> OTHER INFORMATION: Arg, His, Phe, or Ser

<400> SEQUENCE: 134

Xaa Xaa Xaa Cys Xaa Xaa Xaa Xaa Xaa Xaa Xaa Xaa Cys Xaa Xaa Xaa
1               5                   10                  15

<210> SEQ ID NO 135
<211> LENGTH: 20
<212> TYPE: PRT
<213> ORGANISM: Artificial Sequence
<220> FEATURE:
<223> OTHER INFORMATION: albumin binding peptide
<221> NAME/KEY: MISC_FEATURE
<222> LOCATION: (3)..(3)
<223> OTHER INFORMATION: Arg, Phe, or Tyr
<221> NAME/KEY: MISC_FEATURE
<222> LOCATION: (4)..(4)
<223> OTHER INFORMATION: Arg, Leu, Ser, or Trp
<221> NAME/KEY: MISC_FEATURE
<222> LOCATION: (5)..(5)
<223> OTHER INFORMATION: Asn, Asp, Phe, or Tyr
<221> NAME/KEY: MISC_FEATURE
<222> LOCATION: (7)..(7)
<223> OTHER INFORMATION: Gln, Glu, Phe, or Met
<221> NAME/KEY: MISC_FEATURE
<222> LOCATION: (8)..(8)
<223> OTHER INFORMATION: Asp, Pro, or Thr
<221> NAME/KEY: MISC_FEATURE
<222> LOCATION: (9)..(9)
<223> OTHER INFORMATION: Ile, Ser, or Trp
<221> NAME/KEY: MISC_FEATURE
<222> LOCATION: (10)..(10)
<223> OTHER INFORMATION: His, Met, Phe or Pro
<221> NAME/KEY: MISC_FEATURE
<222> LOCATION: (11)..(11)
<223> OTHER INFORMATION: Asn, Leu, or Thr
<221> NAME/KEY: MISC_FEATURE
<222> LOCATION: (12)..(12)
<223> OTHER INFORMATION: Arg, Asn, His, or Thr
<221> NAME/KEY: MISC_FEATURE
<222> LOCATION: (13)..(13)
<223> OTHER INFORMATION: Arg, Met, Phe, or Tyr
<221> NAME/KEY: MISC_FEATURE
<222> LOCATION: (14)..(14)
<223> OTHER INFORMATION: Asp, Gly, Phe, or Trp
<221> NAME/KEY: MISC_FEATURE
<222> LOCATION: (16)..(16)
<223> OTHER INFORMATION: Ala, Asn, or Asp
<221> NAME/KEY: MISC_FEATURE
<222> LOCATION: (17)..(17)
<223> OTHER INFORMATION: Arg, Phe, Pro, or Tyr
<221> NAME/KEY: MISC_FEATURE
<222> LOCATION: (18)..(18)
<223> OTHER INFORMATION: Arg, His, Phe, or Ser

<400> SEQUENCE: 135

Gly Ser Xaa Xaa Xaa Cys Xaa Xaa Xaa Xaa Xaa Xaa Xaa Xaa Cys Xaa
1               5                   10                  15

Xaa Xaa Ala Pro
            20

<210> SEQ ID NO 136
```

```
<211> LENGTH: 20
<212> TYPE: PRT
<213> ORGANISM: Artificial Sequence
<220> FEATURE:
<223> OTHER INFORMATION: albumin binding peptide

<400> SEQUENCE: 136

Pro Thr Val Val Gln Pro Lys Phe His Ala Phe Thr His Glu Asp Leu
1               5                   10                  15

Leu Trp Ile Phe
            20

<210> SEQ ID NO 137
<211> LENGTH: 20
<212> TYPE: PRT
<213> ORGANISM: Artificial Sequence
<220> FEATURE:
<223> OTHER INFORMATION: albumin binding peptide

<400> SEQUENCE: 137

Leu Lys Ser Gln Met Val His Ala Leu Pro Ala Ala Ser Leu His Asp
1               5                   10                  15

Gln His Glu Leu
            20

<210> SEQ ID NO 138
<211> LENGTH: 20
<212> TYPE: PRT
<213> ORGANISM: Artificial Sequence
<220> FEATURE:
<223> OTHER INFORMATION: albumin binding peptide

<400> SEQUENCE: 138

Ser Gln Val Gln Gly Thr Pro Asp Leu Gln Phe Thr Val Arg Asp Phe
1               5                   10                  15

Ile Tyr Met Phe
            20

<210> SEQ ID NO 139
<211> LENGTH: 12
<212> TYPE: PRT
<213> ORGANISM: Artificial Sequence
<220> FEATURE:
<223> OTHER INFORMATION: albumin binding peptide

<400> SEQUENCE: 139

Cys Gln Thr Thr Trp Pro Phe Thr Met Met Gln Cys
1               5                   10

<210> SEQ ID NO 140
<211> LENGTH: 12
<212> TYPE: PRT
<213> ORGANISM: Artificial Sequence
<220> FEATURE:
<223> OTHER INFORMATION: albumin binding peptide

<400> SEQUENCE: 140

Cys Val Thr Met Trp Pro Phe Glu Gln Ile Phe Cys
1               5                   10

<210> SEQ ID NO 141
<211> LENGTH: 12
<212> TYPE: PRT
<213> ORGANISM: Artificial Sequence
<220> FEATURE:
<223> OTHER INFORMATION: albumin binding peptide
```

-continued

```
<400> SEQUENCE: 141

Cys Phe Thr Tyr Tyr Pro Phe Thr Thr Phe Ser Cys
1               5                   10

<210> SEQ ID NO 142
<211> LENGTH: 12
<212> TYPE: PRT
<213> ORGANISM: Artificial Sequence
<220> FEATURE:
<223> OTHER INFORMATION: albumin binding peptide

<400> SEQUENCE: 142

Cys Trp Thr Lys Phe Pro Phe Asp Leu Val Trp Cys
1               5                   10

<210> SEQ ID NO 143
<211> LENGTH: 12
<212> TYPE: PRT
<213> ORGANISM: Artificial Sequence
<220> FEATURE:
<223> OTHER INFORMATION: albumin binding peptide

<400> SEQUENCE: 143

Cys Val Ser Tyr Trp Pro His Phe Val Pro Val Cys
1               5                   10

<210> SEQ ID NO 144
<211> LENGTH: 12
<212> TYPE: PRT
<213> ORGANISM: Artificial Sequence
<220> FEATURE:
<223> OTHER INFORMATION: albumin binding peptide

<400> SEQUENCE: 144

Cys Tyr Ile Ser Phe Pro Phe Asp Gln Met Tyr Cys
1               5                   10

<210> SEQ ID NO 145
<211> LENGTH: 12
<212> TYPE: PRT
<213> ORGANISM: Artificial Sequence
<220> FEATURE:
<223> OTHER INFORMATION: albumin binding peptide

<400> SEQUENCE: 145

Cys Ser Val Gln Tyr Pro Phe Glu Val Val Val Cys
1               5                   10

<210> SEQ ID NO 146
<211> LENGTH: 12
<212> TYPE: PRT
<213> ORGANISM: Artificial Sequence
<220> FEATURE:
<223> OTHER INFORMATION: albumin binding peptide

<400> SEQUENCE: 146

Cys Trp Thr Gln Tyr Pro Phe Asp His Ser Thr Cys
1               5                   10

<210> SEQ ID NO 147
<211> LENGTH: 12
<212> TYPE: PRT
<213> ORGANISM: Artificial Sequence
<220> FEATURE:
<223> OTHER INFORMATION: albumin binding peptide
```

```
<400> SEQUENCE: 147

Cys Ile Thr Trp Pro Phe Lys Arg Pro Trp Pro Cys
1               5                   10

<210> SEQ ID NO 148
<211> LENGTH: 12
<212> TYPE: PRT
<213> ORGANISM: Artificial Sequence
<220> FEATURE:
<223> OTHER INFORMATION: albumin binding peptide

<400> SEQUENCE: 148

Cys Ile Ser Trp Pro Phe Glu Met Pro Phe His Cys
1               5                   10

<210> SEQ ID NO 149
<211> LENGTH: 12
<212> TYPE: PRT
<213> ORGANISM: Artificial Sequence
<220> FEATURE:
<223> OTHER INFORMATION: albumin binding peptide

<400> SEQUENCE: 149

Cys Ile Thr Trp Pro Phe Lys Arg Pro Trp Pro Cys
1               5                   10

<210> SEQ ID NO 150
<211> LENGTH: 12
<212> TYPE: PRT
<213> ORGANISM: Artificial Sequence
<220> FEATURE:
<223> OTHER INFORMATION: albumin binding peptide

<400> SEQUENCE: 150

Cys Ile Thr Tyr Pro Phe His Glu Met Phe Pro Cys
1               5                   10

<210> SEQ ID NO 151
<211> LENGTH: 12
<212> TYPE: PRT
<213> ORGANISM: Artificial Sequence
<220> FEATURE:
<223> OTHER INFORMATION: albumin binding peptide

<400> SEQUENCE: 151

Cys Ile Thr Trp Pro Phe Gln Thr Ser Tyr Pro Cys
1               5                   10

<210> SEQ ID NO 152
<211> LENGTH: 12
<212> TYPE: PRT
<213> ORGANISM: Artificial Sequence
<220> FEATURE:
<223> OTHER INFORMATION: albumin binding peptide

<400> SEQUENCE: 152

Cys Lys Phe Ser Trp Ile Arg Ser Pro Ala Phe Cys
1               5                   10

<210> SEQ ID NO 153
<211> LENGTH: 12
<212> TYPE: PRT
<213> ORGANISM: Artificial Sequence
<220> FEATURE:
<223> OTHER INFORMATION: albumin binding peptide

<400> SEQUENCE: 153
```

Cys Trp Ile Val Asp Glu Asp Gly Thr Lys Trp Cys
1               5                   10

<210> SEQ ID NO 154
<211> LENGTH: 12
<212> TYPE: PRT
<213> ORGANISM: Artificial Sequence
<220> FEATURE:
<223> OTHER INFORMATION: albumin binding peptide

<400> SEQUENCE: 154

Cys Asp Ser Ala Tyr Trp Gln Glu Ile Pro Ala Cys
1               5                   10

<210> SEQ ID NO 155
<211> LENGTH: 8
<212> TYPE: PRT
<213> ORGANISM: Artificial Sequence
<220> FEATURE:
<223> OTHER INFORMATION: albumin binding peptide

<400> SEQUENCE: 155

Cys Leu Trp Asp Pro Met Leu Cys
1               5

<210> SEQ ID NO 156
<211> LENGTH: 12
<212> TYPE: PRT
<213> ORGANISM: Artificial Sequence
<220> FEATURE:
<223> OTHER INFORMATION: albumin binding peptide

<400> SEQUENCE: 156

Cys Glu His Pro Tyr Trp Thr Glu Val Asp Lys Cys
1               5                   10

<210> SEQ ID NO 157
<211> LENGTH: 12
<212> TYPE: PRT
<213> ORGANISM: Artificial Sequence
<220> FEATURE:
<223> OTHER INFORMATION: albumin binding peptide

<400> SEQUENCE: 157

Cys Asp Thr Pro Tyr Trp Arg Asp Leu Trp Gln Cys
1               5                   10

<210> SEQ ID NO 158
<211> LENGTH: 12
<212> TYPE: PRT
<213> ORGANISM: Artificial Sequence
<220> FEATURE:
<223> OTHER INFORMATION: albumin binding peptide

<400> SEQUENCE: 158

Cys Gln Leu Pro Tyr Met Ser Thr Pro Glu Phe Cys
1               5                   10

<210> SEQ ID NO 159
<211> LENGTH: 12
<212> TYPE: PRT
<213> ORGANISM: Artificial Sequence
<220> FEATURE:
<223> OTHER INFORMATION: albumin binding peptide

<400> SEQUENCE: 159

-continued

Cys Gly Arg Gly Phe Asp Lys Glu Ser Ile Tyr Cys
1               5                   10

<210> SEQ ID NO 160
<211> LENGTH: 12
<212> TYPE: PRT
<213> ORGANISM: Artificial Sequence
<220> FEATURE:
<223> OTHER INFORMATION: albumin binding peptide

<400> SEQUENCE: 160

Cys Val Thr Tyr Ile Gly Thr Trp Glu Thr Val Cys
1               5                   10

<210> SEQ ID NO 161
<211> LENGTH: 12
<212> TYPE: PRT
<213> ORGANISM: Artificial Sequence
<220> FEATURE:
<223> OTHER INFORMATION: albumin binding peptide

<400> SEQUENCE: 161

Cys Thr Asp Thr Asn Trp Ser Trp Met Phe Asp Cys
1               5                   10

<210> SEQ ID NO 162
<211> LENGTH: 12
<212> TYPE: PRT
<213> ORGANISM: Artificial Sequence
<220> FEATURE:
<223> OTHER INFORMATION: albumin binding peptide

<400> SEQUENCE: 162

Cys Thr Leu Glu Ile Gly Thr Trp Phe Val Phe Cys
1               5                   10

<210> SEQ ID NO 163
<211> LENGTH: 12
<212> TYPE: PRT
<213> ORGANISM: Artificial Sequence
<220> FEATURE:
<223> OTHER INFORMATION: albumin binding peptide

<400> SEQUENCE: 163

Cys Lys Ile Ala Leu Phe Gln His Phe Glu Val Cys
1               5                   10

<210> SEQ ID NO 164
<211> LENGTH: 12
<212> TYPE: PRT
<213> ORGANISM: Artificial Sequence
<220> FEATURE:
<223> OTHER INFORMATION: albumin binding peptide

<400> SEQUENCE: 164

Cys Ile Lys Leu Tyr Gly Leu Gly His Met Tyr Cys
1               5                   10

<210> SEQ ID NO 165
<211> LENGTH: 12
<212> TYPE: PRT
<213> ORGANISM: Artificial Sequence
<220> FEATURE:
<223> OTHER INFORMATION: albumin binding peptide

<400> SEQUENCE: 165

Cys Glu Met Gln Ser Ile Ile Pro Trp Trp Glu Cys

```
<210> SEQ ID NO 166
<211> LENGTH: 12
<212> TYPE: PRT
<213> ORGANISM: Artificial Sequence
<220> FEATURE:
<223> OTHER INFORMATION: albumin binding peptide

<400> SEQUENCE: 166

Cys Val Glu Lys Tyr Tyr Trp Asp Val Leu Ile Cys
1               5                   10

<210> SEQ ID NO 167
<211> LENGTH: 11
<212> TYPE: PRT
<213> ORGANISM: Artificial Sequence
<220> FEATURE:
<223> OTHER INFORMATION: albumin binding peptide

<400> SEQUENCE: 167

Cys Pro His Gly Arg Tyr Ser Met Phe Pro Cys
1               5                   10

<210> SEQ ID NO 168
<211> LENGTH: 12
<212> TYPE: PRT
<213> ORGANISM: Artificial Sequence
<220> FEATURE:
<223> OTHER INFORMATION: albumin binding peptide

<400> SEQUENCE: 168

Cys Asn Val Arg Trp Thr Asp Thr Pro Tyr Trp Cys
1               5                   10

<210> SEQ ID NO 169
<211> LENGTH: 12
<212> TYPE: PRT
<213> ORGANISM: Artificial Sequence
<220> FEATURE:
<223> OTHER INFORMATION: albumin binding peptide

<400> SEQUENCE: 169

Cys Thr Tyr Asp Pro Ile Ala Asp Leu Leu Phe Cys
1               5                   10

<210> SEQ ID NO 170
<211> LENGTH: 10
<212> TYPE: PRT
<213> ORGANISM: Artificial Sequence
<220> FEATURE:
<223> OTHER INFORMATION: albumin binding peptide

<400> SEQUENCE: 170

Cys Met Asp Trp Pro Asn His Arg Asp Cys
1               5                   10

<210> SEQ ID NO 171
<211> LENGTH: 10
<212> TYPE: PRT
<213> ORGANISM: Artificial Sequence
<220> FEATURE:
<223> OTHER INFORMATION: albumin binding peptide

<400> SEQUENCE: 171

Cys Phe Pro Ile His Leu Thr Met Phe Cys
1               5                   10
```

```
<210> SEQ ID NO 172
<211> LENGTH: 10
<212> TYPE: PRT
<213> ORGANISM: Artificial Sequence
<220> FEATURE:
<223> OTHER INFORMATION: albumin binding peptide

<400> SEQUENCE: 172

Cys Gln Thr Ser Phe Thr Asn Tyr Trp Cys
1               5                   10

<210> SEQ ID NO 173
<211> LENGTH: 9
<212> TYPE: PRT
<213> ORGANISM: Artificial Sequence
<220> FEATURE:
<223> OTHER INFORMATION: albumin binding peptide

<400> SEQUENCE: 173

Cys Met Glu Phe Gly Pro Asp Asp Cys
1               5

<210> SEQ ID NO 174
<211> LENGTH: 8
<212> TYPE: PRT
<213> ORGANISM: Artificial Sequence
<220> FEATURE:
<223> OTHER INFORMATION: albumin binding peptide

<400> SEQUENCE: 174

Cys Ser Trp Asp Pro Ile Phe Cys
1               5

<210> SEQ ID NO 175
<211> LENGTH: 8
<212> TYPE: PRT
<213> ORGANISM: Artificial Sequence
<220> FEATURE:
<223> OTHER INFORMATION: albumin binding peptide

<400> SEQUENCE: 175

Cys Ala Trp Asp Pro Leu Val Cys
1               5

<210> SEQ ID NO 176
<211> LENGTH: 8
<212> TYPE: PRT
<213> ORGANISM: Artificial Sequence
<220> FEATURE:
<223> OTHER INFORMATION: albumin binding peptide

<400> SEQUENCE: 176

Cys His Ile Tyr Asp Trp Phe Cys
1               5

<210> SEQ ID NO 177
<211> LENGTH: 8
<212> TYPE: PRT
<213> ORGANISM: Artificial Sequence
<220> FEATURE:
<223> OTHER INFORMATION: albumin binding peptide

<400> SEQUENCE: 177

Cys Leu Trp Asp Pro Met Ile Cys
1               5
```

```
<210> SEQ ID NO 178
<211> LENGTH: 8
<212> TYPE: PRT
<213> ORGANISM: Artificial Sequence
<220> FEATURE:
<223> OTHER INFORMATION: albumin binding peptide

<400> SEQUENCE: 178

Cys Ser Pro Pro Gly Lys Thr Cys
1               5

<210> SEQ ID NO 179
<211> LENGTH: 8
<212> TYPE: PRT
<213> ORGANISM: Artificial Sequence
<220> FEATURE:
<223> OTHER INFORMATION: albumin binding peptide

<400> SEQUENCE: 179

Cys Thr Phe Trp Gln Tyr Trp Cys
1               5

<210> SEQ ID NO 180
<211> LENGTH: 8
<212> TYPE: PRT
<213> ORGANISM: Artificial Sequence
<220> FEATURE:
<223> OTHER INFORMATION: albumin binding peptide

<400> SEQUENCE: 180

Cys Met Phe Glu Leu Pro Phe Cys
1               5

<210> SEQ ID NO 181
<211> LENGTH: 8
<212> TYPE: PRT
<213> ORGANISM: Artificial Sequence
<220> FEATURE:
<223> OTHER INFORMATION: albumin binding peptide

<400> SEQUENCE: 181

Cys Phe Ser Lys Pro Asp Gln Cys
1               5

<210> SEQ ID NO 182
<211> LENGTH: 8
<212> TYPE: PRT
<213> ORGANISM: Artificial Sequence
<220> FEATURE:
<223> OTHER INFORMATION: albumin binding peptide

<400> SEQUENCE: 182

Cys Phe Tyr Gln Trp Trp Gly Cys
1               5

<210> SEQ ID NO 183
<211> LENGTH: 8
<212> TYPE: PRT
<213> ORGANISM: Artificial Sequence
<220> FEATURE:
<223> OTHER INFORMATION: albumin binding peptide

<400> SEQUENCE: 183

Cys Thr Trp Asp Pro Ile Phe Cys
1               5
```

```
<210> SEQ ID NO 184
<211> LENGTH: 6
<212> TYPE: PRT
<213> ORGANISM: Artificial Sequence
<220> FEATURE:
<223> OTHER INFORMATION: albumin binding peptide

<400> SEQUENCE: 184

Cys Trp Leu Tyr Asp Cys
1               5

<210> SEQ ID NO 185
<211> LENGTH: 6
<212> TYPE: PRT
<213> ORGANISM: Artificial Sequence
<220> FEATURE:
<223> OTHER INFORMATION: albumin binding peptide

<400> SEQUENCE: 185

Cys Asp Lys Tyr Gly Cys
1               5

<210> SEQ ID NO 186
<211> LENGTH: 6
<212> TYPE: PRT
<213> ORGANISM: Artificial Sequence
<220> FEATURE:
<223> OTHER INFORMATION: albumin binding peptide

<400> SEQUENCE: 186

Cys Ser Lys Asp Thr Cys
1               5

<210> SEQ ID NO 187
<211> LENGTH: 18
<212> TYPE: PRT
<213> ORGANISM: Artificial Sequence
<220> FEATURE:
<223> OTHER INFORMATION: albumin binding peptide

<400> SEQUENCE: 187

Leu Arg Asp Cys Gln Thr Thr Trp Pro Phe Thr Met Met Gln Cys Pro
1               5                   10                  15

Asn Asn

<210> SEQ ID NO 188
<211> LENGTH: 18
<212> TYPE: PRT
<213> ORGANISM: Artificial Sequence
<220> FEATURE:
<223> OTHER INFORMATION: albumin binding peptide

<400> SEQUENCE: 188

Asn Arg Glu Cys Val Thr Met Trp Pro Phe Glu Gln Ile Phe Cys Pro
1               5                   10                  15

Trp Pro

<210> SEQ ID NO 189
<211> LENGTH: 18
<212> TYPE: PRT
<213> ORGANISM: Artificial Sequence
<220> FEATURE:
<223> OTHER INFORMATION: albumin binding peptide

<400> SEQUENCE: 189

Leu Arg Ser Cys Phe Thr Tyr Tyr Pro Phe Thr Thr Phe Ser Cys Ser
```

-continued

```
                1               5                  10                  15
Pro Ala

<210> SEQ ID NO 190
<211> LENGTH: 18
<212> TYPE: PRT
<213> ORGANISM: Artificial Sequence
<220> FEATURE:
<223> OTHER INFORMATION: albumin binding peptide

<400> SEQUENCE: 190

Leu Ser His Cys Trp Thr Lys Phe Pro Phe Asp Leu Val Trp Cys Asp
1               5                  10                  15

Ser Pro

<210> SEQ ID NO 191
<211> LENGTH: 18
<212> TYPE: PRT
<213> ORGANISM: Artificial Sequence
<220> FEATURE:
<223> OTHER INFORMATION: albumin binding peptide

<400> SEQUENCE: 191

Leu Arg Met Cys Val Ser Tyr Trp Pro His Phe Val Pro Val Cys Glu
1               5                  10                  15

Asn Pro

<210> SEQ ID NO 192
<211> LENGTH: 18
<212> TYPE: PRT
<213> ORGANISM: Artificial Sequence
<220> FEATURE:
<223> OTHER INFORMATION: albumin binding peptide

<400> SEQUENCE: 192

Leu Arg Asp Cys Tyr Ile Ser Phe Pro Phe Asp Gln Met Tyr Cys Ser
1               5                  10                  15

His Phe

<210> SEQ ID NO 193
<211> LENGTH: 18
<212> TYPE: PRT
<213> ORGANISM: Artificial Sequence
<220> FEATURE:
<223> OTHER INFORMATION: albumin binding peptide

<400> SEQUENCE: 193

Phe Arg His Cys Ser Val Gln Tyr Pro Phe Glu Val Val Val Cys Pro
1               5                  10                  15

Ala Asn

<210> SEQ ID NO 194
<211> LENGTH: 18
<212> TYPE: PRT
<213> ORGANISM: Artificial Sequence
<220> FEATURE:
<223> OTHER INFORMATION: albumin binding peptide

<400> SEQUENCE: 194

Leu Arg Asn Cys Trp Thr Gln Tyr Pro Phe Asp His Ser Thr Cys Ser
1               5                  10                  15

Pro Asn
```

<210> SEQ ID NO 195
<211> LENGTH: 17
<212> TYPE: PRT
<213> ORGANISM: Artificial Sequence
<220> FEATURE:
<223> OTHER INFORMATION: albumin binding peptide

<400> SEQUENCE: 195

Asp Ser Met Cys Ile Thr Trp Pro Phe Lys Arg Pro Trp Pro Cys Ala
1               5                   10                  15

Asn

<210> SEQ ID NO 196
<211> LENGTH: 18
<212> TYPE: PRT
<213> ORGANISM: Artificial Sequence
<220> FEATURE:
<223> OTHER INFORMATION: albumin binding peptide

<400> SEQUENCE: 196

Ala Phe Met Cys Ile Ser Trp Pro Phe Glu Met Pro Phe His Cys Ser
1               5                   10                  15

Pro Asp

<210> SEQ ID NO 197
<211> LENGTH: 18
<212> TYPE: PRT
<213> ORGANISM: Artificial Sequence
<220> FEATURE:
<223> OTHER INFORMATION: albumin binding peptide

<400> SEQUENCE: 197

Asp Ser Met Cys Ile Thr Trp Pro Phe Lys Arg Pro Trp Pro Cys Ala
1               5                   10                  15

Asn Pro

<210> SEQ ID NO 198
<211> LENGTH: 18
<212> TYPE: PRT
<213> ORGANISM: Artificial Sequence
<220> FEATURE:
<223> OTHER INFORMATION: albumin binding peptide

<400> SEQUENCE: 198

Trp Asp Leu Cys Ile Thr Tyr Pro Phe His Glu Met Phe Pro Cys Glu
1               5                   10                  15

Asp Gly

<210> SEQ ID NO 199
<211> LENGTH: 18
<212> TYPE: PRT
<213> ORGANISM: Artificial Sequence
<220> FEATURE:
<223> OTHER INFORMATION: albumin binding peptide

<400> SEQUENCE: 199

Gly Gly Glu Cys Ile Thr Trp Pro Phe Gln Thr Ser Tyr Pro Cys Thr
1               5                   10                  15

Asn Gly

<210> SEQ ID NO 200
<211> LENGTH: 18
<212> TYPE: PRT

```
<213> ORGANISM: Artificial Sequence
<220> FEATURE:
<223> OTHER INFORMATION: albumin binding peptide

<400> SEQUENCE: 200

Arg Asn Met Cys Lys Phe Ser Trp Ile Arg Ser Pro Ala Phe Cys Ala
1               5                   10                  15

Arg Ala

<210> SEQ ID NO 201
<211> LENGTH: 17
<212> TYPE: PRT
<213> ORGANISM: Artificial Sequence
<220> FEATURE:
<223> OTHER INFORMATION: albumin binding peptide

<400> SEQUENCE: 201

Phe Ser Leu Cys Trp Ile Val Asp Glu Asp Gly Thr Lys Trp Cys Leu
1               5                   10                  15

Pro

<210> SEQ ID NO 202
<211> LENGTH: 18
<212> TYPE: PRT
<213> ORGANISM: Artificial Sequence
<220> FEATURE:
<223> OTHER INFORMATION: albumin binding peptide

<400> SEQUENCE: 202

Arg Trp Phe Cys Asp Ser Ala Tyr Trp Gln Glu Ile Pro Ala Cys Ala
1               5                   10                  15

Arg Asp

<210> SEQ ID NO 203
<211> LENGTH: 14
<212> TYPE: PRT
<213> ORGANISM: Artificial Sequence
<220> FEATURE:
<223> OTHER INFORMATION: albumin binding peptide

<400> SEQUENCE: 203

Arg Trp Tyr Cys Leu Trp Asp Pro Met Leu Cys Met Ser Asp
1               5                   10

<210> SEQ ID NO 204
<211> LENGTH: 18
<212> TYPE: PRT
<213> ORGANISM: Artificial Sequence
<220> FEATURE:
<223> OTHER INFORMATION: albumin binding peptide

<400> SEQUENCE: 204

Ala Trp Tyr Cys Glu His Pro Tyr Trp Thr Glu Val Asp Lys Cys His
1               5                   10                  15

Ser Ser

<210> SEQ ID NO 205
<211> LENGTH: 18
<212> TYPE: PRT
<213> ORGANISM: Artificial Sequence
<220> FEATURE:
<223> OTHER INFORMATION: albumin binding peptide

<400> SEQUENCE: 205
```

-continued

```
Ser Asp Phe Cys Asp Thr Pro Tyr Trp Arg Asp Leu Trp Gln Cys Asn
1               5                   10                  15

Ser Pro
```

<210> SEQ ID NO 206
<211> LENGTH: 18
<212> TYPE: PRT
<213> ORGANISM: Artificial Sequence
<220> FEATURE:
<223> OTHER INFORMATION: albumin binding peptide

<400> SEQUENCE: 206

```
Leu Pro Trp Cys Gln Leu Pro Tyr Met Ser Thr Pro Glu Phe Cys Ile
1               5                   10                  15

Arg Pro
```

<210> SEQ ID NO 207
<211> LENGTH: 18
<212> TYPE: PRT
<213> ORGANISM: Artificial Sequence
<220> FEATURE:
<223> OTHER INFORMATION: albumin binding peptide

<400> SEQUENCE: 207

```
Tyr His Val Cys Gly Arg Gly Phe Asp Lys Glu Ser Ile Tyr Cys Lys
1               5                   10                  15

Phe Leu
```

<210> SEQ ID NO 208
<211> LENGTH: 17
<212> TYPE: PRT
<213> ORGANISM: Artificial Sequence
<220> FEATURE:
<223> OTHER INFORMATION: albumin binding peptide

<400> SEQUENCE: 208

```
Ser Phe Cys Val Thr Tyr Ile Gly Thr Trp Glu Thr Val Cys Lys Arg
1               5                   10                  15

Ser
```

<210> SEQ ID NO 209
<211> LENGTH: 18
<212> TYPE: PRT
<213> ORGANISM: Artificial Sequence
<220> FEATURE:
<223> OTHER INFORMATION: albumin binding peptide

<400> SEQUENCE: 209

```
Asn Asp Gly Cys Thr Asp Thr Asn Trp Ser Trp Met Phe Asp Cys Pro
1               5                   10                  15

Pro Leu
```

<210> SEQ ID NO 210
<211> LENGTH: 18
<212> TYPE: PRT
<213> ORGANISM: Artificial Sequence
<220> FEATURE:
<223> OTHER INFORMATION: albumin binding peptide

<400> SEQUENCE: 210

```
Trp Arg Asp Cys Thr Leu Glu Ile Gly Thr Trp Phe Val Phe Cys Lys
1               5                   10                  15

Gly Ser
```

```
<210> SEQ ID NO 211
<211> LENGTH: 18
<212> TYPE: PRT
<213> ORGANISM: Artificial Sequence
<220> FEATURE:
<223> OTHER INFORMATION: albumin binding peptide

<400> SEQUENCE: 211

Ser Pro Tyr Cys Lys Ile Ala Leu Phe Gln His Phe Glu Val Cys Ala
1               5                   10                  15

Ala Asp

<210> SEQ ID NO 212
<211> LENGTH: 18
<212> TYPE: PRT
<213> ORGANISM: Artificial Sequence
<220> FEATURE:
<223> OTHER INFORMATION: albumin binding peptide

<400> SEQUENCE: 212

Arg His Trp Cys Ile Lys Leu Tyr Gly Leu Gly His Met Tyr Cys Asn
1               5                   10                  15

Arg Ser

<210> SEQ ID NO 213
<211> LENGTH: 18
<212> TYPE: PRT
<213> ORGANISM: Artificial Sequence
<220> FEATURE:
<223> OTHER INFORMATION: albumin binding peptide

<400> SEQUENCE: 213

Asp His Ala Cys Glu Met Gln Ser Ile Ile Pro Trp Trp Glu Cys Tyr
1               5                   10                  15

Pro His

<210> SEQ ID NO 214
<211> LENGTH: 18
<212> TYPE: PRT
<213> ORGANISM: Artificial Sequence
<220> FEATURE:
<223> OTHER INFORMATION: albumin binding peptide

<400> SEQUENCE: 214

Pro Arg Ser Cys Val Glu Lys Tyr Tyr Trp Asp Val Leu Ile Cys Gly
1               5                   10                  15

Phe Phe

<210> SEQ ID NO 215
<211> LENGTH: 17
<212> TYPE: PRT
<213> ORGANISM: Artificial Sequence
<220> FEATURE:
<223> OTHER INFORMATION: albumin binding peptide

<400> SEQUENCE: 215

Phe His Thr Cys Pro His Gly Arg Tyr Ser Met Phe Pro Cys Asp Tyr
1               5                   10                  15

Trp

<210> SEQ ID NO 216
<211> LENGTH: 18
```

```
<212> TYPE: PRT
<213> ORGANISM: Artificial Sequence
<220> FEATURE:
<223> OTHER INFORMATION: albumin binding peptide

<400> SEQUENCE: 216

His Gly Trp Cys Asn Val Arg Trp Thr Asp Thr Pro Tyr Trp Cys Ala
1               5                   10                  15
Phe Ser

<210> SEQ ID NO 217
<211> LENGTH: 18
<212> TYPE: PRT
<213> ORGANISM: Artificial Sequence
<220> FEATURE:
<223> OTHER INFORMATION: albumin binding peptide

<400> SEQUENCE: 217

Tyr Arg Val Cys Thr Tyr Asp Pro Ile Ala Asp Leu Leu Phe Cys Pro
1               5                   10                  15
Phe Asn

<210> SEQ ID NO 218
<211> LENGTH: 16
<212> TYPE: PRT
<213> ORGANISM: Artificial Sequence
<220> FEATURE:
<223> OTHER INFORMATION: albumin binding peptide

<400> SEQUENCE: 218

Arg Ser Phe Cys Met Asp Trp Pro Asn His Arg Asp Cys Asp Tyr Ser
1               5                   10                  15

<210> SEQ ID NO 219
<211> LENGTH: 16
<212> TYPE: PRT
<213> ORGANISM: Artificial Sequence
<220> FEATURE:
<223> OTHER INFORMATION: albumin binding peptide

<400> SEQUENCE: 219

Phe Trp Asp Cys Phe Pro Ile His Leu Thr Met Phe Cys Asp Arg Phe
1               5                   10                  15

<210> SEQ ID NO 220
<211> LENGTH: 16
<212> TYPE: PRT
<213> ORGANISM: Artificial Sequence
<220> FEATURE:
<223> OTHER INFORMATION: albumin binding peptide

<400> SEQUENCE: 220

Tyr Leu Tyr Cys Gln Thr Ser Phe Thr Asn Tyr Trp Cys Ala Phe His
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: albumin binding peptide

<400> SEQUENCE: 221

Gly Leu Tyr Cys Met Glu Phe Gly Pro Asp Asp Cys Ala Trp His
1               5                   10                  15
```

```
<210> SEQ ID NO 222
<211> LENGTH: 14
<212> TYPE: PRT
<213> ORGANISM: Artificial Sequence
<220> FEATURE:
<223> OTHER INFORMATION: albumin binding peptide

<400> SEQUENCE: 222

Lys Asn Phe Cys Ser Trp Asp Pro Ile Phe Cys Gly Ile His
1               5                   10

<210> SEQ ID NO 223
<211> LENGTH: 14
<212> TYPE: PRT
<213> ORGANISM: Artificial Sequence
<220> FEATURE:
<223> OTHER INFORMATION: albumin binding peptide

<400> SEQUENCE: 223

Lys Trp Tyr Cys Ala Trp Asp Pro Leu Val Cys Glu Ile Phe
1               5                   10

<210> SEQ ID NO 224
<211> LENGTH: 14
<212> TYPE: PRT
<213> ORGANISM: Artificial Sequence
<220> FEATURE:
<223> OTHER INFORMATION: albumin binding peptide

<400> SEQUENCE: 224

Trp Thr Thr Cys His Ile Tyr Asp Trp Phe Cys Ser Ser Ser
1               5                   10

<210> SEQ ID NO 225
<211> LENGTH: 14
<212> TYPE: PRT
<213> ORGANISM: Artificial Sequence
<220> FEATURE:
<223> OTHER INFORMATION: albumin binding peptide

<400> SEQUENCE: 225

Gln Trp Tyr Cys Leu Trp Asp Pro Met Ile Cys Gly Leu Ile
1               5                   10

<210> SEQ ID NO 226
<211> LENGTH: 14
<212> TYPE: PRT
<213> ORGANISM: Artificial Sequence
<220> FEATURE:
<223> OTHER INFORMATION: albumin binding peptide

<400> SEQUENCE: 226

Gln Thr Asn Cys Ser Pro Pro Gly Lys Thr Cys Asp Lys Asn
1               5                   10

<210> SEQ ID NO 227
<211> LENGTH: 13
<212> TYPE: PRT
<213> ORGANISM: Artificial Sequence
<220> FEATURE:
<223> OTHER INFORMATION: albumin binding peptide

<400> SEQUENCE: 227

Ala Ile Cys Thr Phe Trp Gln Tyr Trp Cys Leu Glu Pro
1               5                   10
```

-continued

<210> SEQ ID NO 228
<211> LENGTH: 14
<212> TYPE: PRT
<213> ORGANISM: Artificial Sequence
<220> FEATURE:
<223> OTHER INFORMATION: albumin binding peptide

<400> SEQUENCE: 228

Phe Glu Trp Cys Met Phe Glu Leu Pro Phe Cys Ser Trp Pro
1               5                   10

<210> SEQ ID NO 229
<211> LENGTH: 14
<212> TYPE: PRT
<213> ORGANISM: Artificial Sequence
<220> FEATURE:
<223> OTHER INFORMATION: albumin binding peptide

<400> SEQUENCE: 229

Gln Glu Gly Cys Phe Ser Lys Pro Asp Gln Cys Lys Val Met
1               5                   10

<210> SEQ ID NO 230
<211> LENGTH: 14
<212> TYPE: PRT
<213> ORGANISM: Artificial Sequence
<220> FEATURE:
<223> OTHER INFORMATION: albumin binding peptide

<400> SEQUENCE: 230

Leu Glu Tyr Cys Phe Tyr Gln Trp Trp Gly Cys Pro His Ala
1               5                   10

<210> SEQ ID NO 231
<211> LENGTH: 14
<212> TYPE: PRT
<213> ORGANISM: Artificial Sequence
<220> FEATURE:
<223> OTHER INFORMATION: albumin binding peptide

<400> SEQUENCE: 231

Tyr Gln Phe Cys Thr Trp Asp Pro Ile Phe Cys Gly Trp His
1               5                   10

<210> SEQ ID NO 232
<211> LENGTH: 12
<212> TYPE: PRT
<213> ORGANISM: Artificial Sequence
<220> FEATURE:
<223> OTHER INFORMATION: albumin binding peptide

<400> SEQUENCE: 232

Leu Trp Asp Cys Trp Leu Tyr Asp Cys Glu Gly Asn
1               5                   10

<210> SEQ ID NO 233
<211> LENGTH: 12
<212> TYPE: PRT
<213> ORGANISM: Artificial Sequence
<220> FEATURE:
<223> OTHER INFORMATION: albumin binding peptide

<400> SEQUENCE: 233

Val His Ser Cys Asp Lys Tyr Gly Cys Val Asn Ala
1               5                   10

<210> SEQ ID NO 234

```
<211> LENGTH: 12
<212> TYPE: PRT
<213> ORGANISM: Artificial Sequence
<220> FEATURE:
<223> OTHER INFORMATION: albumin binding peptide

<400> SEQUENCE: 234

Phe Glu His Cys Ser Lys Asp Thr Cys Ser Gly Asn
1               5                   10

<210> SEQ ID NO 235
<211> LENGTH: 14
<212> TYPE: PRT
<213> ORGANISM: Artificial Sequence
<220> FEATURE:
<223> OTHER INFORMATION: variegated display library template
<221> NAME/KEY: MISC_FEATURE
<222> LOCATION: (1)..(3)
<223> OTHER INFORMATION: any amino acid except Cys
<221> NAME/KEY: MISC_FEATURE
<222> LOCATION: (5)..(10)
<223> OTHER INFORMATION: any amino acid except Cys
<221> NAME/KEY: MISC_FEATURE
<222> LOCATION: (12)..(14)
<223> OTHER INFORMATION: any amino acid except Cys

<400> SEQUENCE: 235

Xaa Xaa Xaa Cys Xaa Xaa Xaa Xaa Xaa Xaa Cys Xaa Xaa Xaa
1               5                   10

<210> SEQ ID NO 236
<211> LENGTH: 15
<212> TYPE: PRT
<213> ORGANISM: Artificial Sequence
<220> FEATURE:
<223> OTHER INFORMATION: variegated display library template
<221> NAME/KEY: MISC_FEATURE
<222> LOCATION: (1)..(3)
<223> OTHER INFORMATION: any amino acid except Cys
<221> NAME/KEY: MISC_FEATURE
<222> LOCATION: (5)..(11)
<223> OTHER INFORMATION: any amino acid except Cys
<221> NAME/KEY: MISC_FEATURE
<222> LOCATION: (13)..(15)
<223> OTHER INFORMATION: any amino acid except Cys

<400> SEQUENCE: 236

Xaa Xaa Xaa Cys Xaa Xaa Xaa Xaa Xaa Xaa Xaa Cys Xaa Xaa Xaa
1               5                   10                  15

<210> SEQ ID NO 237
<211> LENGTH: 12
<212> TYPE: PRT
<213> ORGANISM: Artificial Sequence
<220> FEATURE:
<223> OTHER INFORMATION: variegated display library template
<221> NAME/KEY: MISC_FEATURE
<222> LOCATION: (1)..(1)
<223> OTHER INFORMATION: any amino acid except Cys, Glu, Ile) Lys, Met,
     and Thr
<221> NAME/KEY: MISC_FEATURE
<222> LOCATION: (2)..(3)
<223> OTHER INFORMATION: any amino acid except Cys
<221> NAME/KEY: MISC_FEATURE
<222> LOCATION: (5)..(8)
<223> OTHER INFORMATION: any amino acid except Cys
<221> NAME/KEY: MISC_FEATURE
<222> LOCATION: (10)..(11)
<223> OTHER INFORMATION: any amino acid except Cys
<221> NAME/KEY: MISC_FEATURE
<222> LOCATION: (12)..(12)
<223> OTHER INFORMATION: any amino acid except Cys, Glu, Ile) Lys, Met,
     and Thr
```

```
<400> SEQUENCE: 237

Xaa Xaa Xaa Cys Xaa Xaa Xaa Xaa Cys Xaa Xaa Xaa
1               5                   10

<210> SEQ ID NO 238
<211> LENGTH: 16
<212> TYPE: PRT
<213> ORGANISM: Artificial Sequence
<220> FEATURE:
<223> OTHER INFORMATION: variegated display library template
<221> NAME/KEY: MISC_FEATURE
<222> LOCATION: (1)..(2)
<223> OTHER INFORMATION: Asp, Phe, His, Leu, Asn, Pro, Arg, Ser, Trp, or
      Tyr
<221> NAME/KEY: MISC_FEATURE
<222> LOCATION: (3)..(3)
<223> OTHER INFORMATION: Ala, Asp, Phe, Gly, His, Leu, Asn, Pro, Gln,
      Arg, Ser, Val, Trp, or Tyr
<221> NAME/KEY: MISC_FEATURE
<222> LOCATION: (5)..(12)
<223> OTHER INFORMATION: any amino acid except Cys
<221> NAME/KEY: MISC_FEATURE
<222> LOCATION: (14)..(14)
<223> OTHER INFORMATION: Ala, Asp, Phe, Gly, His, Leu, Asn, Pro, Gln,
      Arg, Ser, Val, Trp, or Tyr
<221> NAME/KEY: MISC_FEATURE
<222> LOCATION: (15)..(16)
<223> OTHER INFORMATION: Asp, Phe, His, Leu, Asn, Pro, Arg, Ser, Trp, or
      Tyr

<400> SEQUENCE: 238

Xaa Xaa Xaa Cys Xaa Xaa Xaa Xaa Xaa Xaa Xaa Cys Xaa Xaa Xaa
1               5                   10                  15

<210> SEQ ID NO 239
<211> LENGTH: 12
<212> TYPE: PRT
<213> ORGANISM: Artificial Sequence
<220> FEATURE:
<223> OTHER INFORMATION: albumin binding peptide

<400> SEQUENCE: 239

Val Ala Trp Cys Thr Ile Phe Leu Cys Leu Asp Val
1               5                   10

<210> SEQ ID NO 240
<211> LENGTH: 12
<212> TYPE: PRT
<213> ORGANISM: Artificial Sequence
<220> FEATURE:
<223> OTHER INFORMATION: albumin binding peptide

<400> SEQUENCE: 240

Phe Lys Ile Cys Asp Gln Trp Phe Cys Leu Met Pro
1               5                   10

<210> SEQ ID NO 241
<211> LENGTH: 12
<212> TYPE: PRT
<213> ORGANISM: Artificial Sequence
<220> FEATURE:
<223> OTHER INFORMATION: albumin binding peptide

<400> SEQUENCE: 241

His Val Gly Cys Asn Asn Ala Leu Cys Met Gln Tyr
1               5                   10

<210> SEQ ID NO 242
```

```
<211> LENGTH: 12
<212> TYPE: PRT
<213> ORGANISM: Artificial Sequence
<220> FEATURE:
<223> OTHER INFORMATION: albumin binding peptide

<400> SEQUENCE: 242

Trp Lys Val Cys Asp His Phe Phe Cys Leu Ser Pro
1               5                   10

<210> SEQ ID NO 243
<211> LENGTH: 12
<212> TYPE: PRT
<213> ORGANISM: Artificial Sequence
<220> FEATURE:
<223> OTHER INFORMATION: albumin binding peptide

<400> SEQUENCE: 243

Asn His Gly Cys Trp His Phe Ser Cys Ile Trp Asp
1               5                   10

<210> SEQ ID NO 244
<211> LENGTH: 16
<212> TYPE: PRT
<213> ORGANISM: Artificial Sequence
<220> FEATURE:
<223> OTHER INFORMATION: albumin binding peptide

<400> SEQUENCE: 244

Phe Arg Asn Cys Glu Pro Trp Met Leu Arg Phe Gly Cys Asn Pro Arg
1               5                   10                  15

<210> SEQ ID NO 245
<211> LENGTH: 18
<212> TYPE: PRT
<213> ORGANISM: Artificial Sequence
<220> FEATURE:
<223> OTHER INFORMATION: albumin binding peptide

<400> SEQUENCE: 245

Ala Asp Phe Cys Glu Gly Lys Asp Met Ile Asp Trp Val Tyr Cys Arg
1               5                   10                  15

Leu Tyr

<210> SEQ ID NO 246
<211> LENGTH: 19
<212> TYPE: PRT
<213> ORGANISM: Artificial Sequence
<220> FEATURE:
<223> OTHER INFORMATION: albumin binding peptide

<400> SEQUENCE: 246

Phe Trp Phe Cys Asp Arg Ile Ala Trp Tyr Pro Gln His Leu Cys Glu
1               5                   10                  15

Phe Leu Asp

<210> SEQ ID NO 247
<211> LENGTH: 18
<212> TYPE: PRT
<213> ORGANISM: Artificial Sequence
<220> FEATURE:
<223> OTHER INFORMATION: albumin binding peptide

<400> SEQUENCE: 247

Asp Trp Asp Cys Val Thr Arg Trp Ala Asn Arg Asp Gln Gln Cys Trp
1               5                   10                  15
```

Gly Pro

<210> SEQ ID NO 248
<211> LENGTH: 18
<212> TYPE: PRT
<213> ORGANISM: Artificial Sequence
<220> FEATURE:
<223> OTHER INFORMATION: albumin binding peptide

<400> SEQUENCE: 248

Asp Trp Asp Cys Val Thr Arg Trp Ala Asn Arg Asp Gln Gln Cys Trp
1               5                   10                  15

Ala Leu

<210> SEQ ID NO 249
<211> LENGTH: 18
<212> TYPE: PRT
<213> ORGANISM: Artificial Sequence
<220> FEATURE:
<223> OTHER INFORMATION: albumin binding peptide

<400> SEQUENCE: 249

Asp Trp Asp Cys Val Thr Asp Trp Ala Asn Arg His Gln His Cys Trp
1               5                   10                  15

Ala Leu

<210> SEQ ID NO 250
<211> LENGTH: 18
<212> TYPE: PRT
<213> ORGANISM: Artificial Sequence
<220> FEATURE:
<223> OTHER INFORMATION: albumin binding peptide

<400> SEQUENCE: 250

Asp Trp Gln Cys Val Lys Asp Trp Ala Asn Arg Arg Arg Gly Cys Met
1               5                   10                  15

Ala Asp

<210> SEQ ID NO 251
<211> LENGTH: 20
<212> TYPE: PRT
<213> ORGANISM: Artificial Sequence
<220> FEATURE:
<223> OTHER INFORMATION: albumin binding peptide

<400> SEQUENCE: 251

Arg Asn Met Cys Lys Phe Ser Trp Ile Arg Ser Pro Ala Phe Cys Ala
1               5                   10                  15

Arg Ala Asp Pro
            20

<210> SEQ ID NO 252
<211> LENGTH: 26
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (26)..(26)
<223> OTHER INFORMATION: AMIDATION

<400> SEQUENCE: 252

Gly Asp Leu Arg Asp Cys Gln Thr Thr Trp Pro Phe Thr Met Met Gln
1               5                   10                  15

Cys Pro Asn Asn Asp Pro Gly Gly Gly Lys
            20                  25

<210> SEQ ID NO 253
<211> LENGTH: 26
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (26)..(26)
<223> OTHER INFORMATION: AMIDATION

<400> SEQUENCE: 253

Gly Asp Asn Arg Glu Cys Val Thr Met Trp Pro Phe Glu Gln Ile Phe
1               5                   10                  15

Cys Pro Trp Pro Asp Pro Gly Gly Gly Lys
            20                  25

<210> SEQ ID NO 254
<211> LENGTH: 26
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (26)..(26)
<223> OTHER INFORMATION: AMIDATION

<400> SEQUENCE: 254

Gly Asp Leu Arg Ser Cys Phe Thr Tyr Tyr Pro Phe Thr Thr Phe Ser
1               5                   10                  15

Cys Ser Pro Ala Asp Pro Gly Gly Gly Lys
            20                  25

<210> SEQ ID NO 255
<211> LENGTH: 25
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (25)..(25)
<223> OTHER INFORMATION: AMIDATION

<400> SEQUENCE: 255

Gly Asp Asp Ser Met Cys Ile Thr Trp Pro Phe Lys Arg Pro Trp Pro
1               5                   10                  15

Cys Ala Asn Asp Pro Gly Gly Gly Lys
            20                  25

<210> SEQ ID NO 256
<211> LENGTH: 26
<212> TYPE: PRT
<213> ORGANISM: Artificial Sequence
<220> FEATURE:

-continued

```
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (26)..(26)
<223> OTHER INFORMATION: AMIDATION

<400> SEQUENCE: 256

Gly Asp Arg Asn Met Cys Lys Phe Ser Trp Ile Arg Ser Pro Ala Phe
1               5                   10                  15

Cys Ala Arg Ala Asp Pro Gly Gly Gly Lys
            20                  25

<210> SEQ ID NO 257
<211> LENGTH: 25
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (25)..(25)
<223> OTHER INFORMATION: AMIDATION

<400> SEQUENCE: 257

Gly Asp Phe Ser Leu Cys Trp Ile Val Asp Glu Asp Gly Thr Lys Trp
1               5                   10                  15

Cys Leu Pro Asp Pro Gly Gly Gly Lys
            20                  25

<210> SEQ ID NO 258
<211> LENGTH: 26
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (26)..(26)
<223> OTHER INFORMATION: AMIDATION

<400> SEQUENCE: 258

Gly Asp Arg Trp Phe Cys Asp Ser Ala Tyr Trp Gln Glu Ile Pro Ala
1               5                   10                  15

Cys Ala Arg Asp Asp Pro Gly Gly Gly Lys
            20                  25

<210> SEQ ID NO 259
<211> LENGTH: 26
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (26)..(26)
<223> OTHER INFORMATION: AMIDATION

<400> SEQUENCE: 259

Gly Asp Ser Asp Phe Cys Asp Thr Pro Tyr Trp Arg Asp Leu Trp Gln
1               5                   10                  15
```

Cys Asn Ser Pro Asp Pro Gly Gly Gly Lys
            20                  25

<210> SEQ ID NO 260
<211> LENGTH: 25
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (25)..(25)
<223> OTHER INFORMATION: AMIDATION

<400> SEQUENCE: 260

Gly Asp Ser Phe Cys Val Thr Tyr Ile Gly Thr Trp Glu Thr Val Cys
1               5                   10                  15

Lys Arg Ser Asp Pro Gly Gly Gly Lys
            20                  25

<210> SEQ ID NO 261
<211> LENGTH: 26
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (26)..(26)
<223> OTHER INFORMATION: AMIDATION

<400> SEQUENCE: 261

Gly Asp Asn Asp Gly Cys Thr Asp Thr Asn Trp Ser Trp Met Phe Asp
1               5                   10                  15

Cys Pro Pro Leu Asp Pro Gly Gly Gly Lys
            20                  25

<210> SEQ ID NO 262
<211> LENGTH: 26
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (26)..(26)
<223> OTHER INFORMATION: AMIDATION

<400> SEQUENCE: 262

Gly Asp Ser Pro Tyr Cys Lys Ile Ala Leu Phe Gln His Phe Glu Val
1               5                   10                  15

Cys Ala Ala Asp Asp Pro Gly Gly Gly Lys
            20                  25

<210> SEQ ID NO 263
<211> LENGTH: 26
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION

```
<221> NAME/KEY: MOD_RES
<222> LOCATION: (26)..(26)
<223> OTHER INFORMATION: AMIDATION

<400> SEQUENCE: 263

Gly Asp Pro Arg Ser Cys Val Glu Lys Tyr Tyr Trp Asp Val Leu Ile
1               5                   10                  15
Cys Gly Phe Phe Asp Pro Gly Gly Gly Lys
            20                  25

<210> SEQ ID NO 264
<211> LENGTH: 24
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (24)..(24)
<223> OTHER INFORMATION: AMIDATION

<400> SEQUENCE: 264

Gly Ser Arg Ser Phe Cys Met Asp Trp Pro Asn His Arg Asp Cys Asp
1               5                   10                  15
Tyr Ser Ala Pro Gly Gly Gly Lys
            20

<210> SEQ ID NO 265
<211> LENGTH: 22
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (22)..(22)
<223> OTHER INFORMATION: AMIDATION

<400> SEQUENCE: 265

Ala Gly Lys Trp Tyr Cys Ala Trp Asp Pro Leu Val Cys Glu Ile Phe
1               5                   10                  15
Gly Thr Gly Gly Gly Lys
            20

<210> SEQ ID NO 266
<211> LENGTH: 22
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (22)..(22)
<223> OTHER INFORMATION: AMIDATION

<400> SEQUENCE: 266

Ala Gly Trp Thr Thr Cys His Ile Tyr Asp Trp Phe Cys Ser Ser Ser
1               5                   10                  15
Gly Thr Gly Gly Gly Lys
            20
```

```
<210> SEQ ID NO 267
<211> LENGTH: 22
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (22)..(22)
<223> OTHER INFORMATION: AMIDATION

<400> SEQUENCE: 267

Ala Gly Leu Glu Tyr Cys Phe Tyr Gln Trp Trp Gly Cys Pro His Ala
1               5                   10                  15

Gly Thr Gly Gly Gly Lys
            20

<210> SEQ ID NO 268
<211> LENGTH: 22
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (22)..(22)
<223> OTHER INFORMATION: AMIDATION

<400> SEQUENCE: 268

Ala Gly Tyr Gln Phe Cys Thr Trp Asp Pro Ile Phe Cys Gly Trp His
1               5                   10                  15

Gly Thr Gly Gly Gly Lys
            20

<210> SEQ ID NO 269
<211> LENGTH: 20
<212> TYPE: PRT
<213> ORGANISM: Artificial Sequence
<220> FEATURE:
<223> OTHER INFORMATION: albumin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (20)..(20)
<223> OTHER INFORMATION: AMIDATION

<400> SEQUENCE: 269

Gly Ser Leu Trp Asp Cys Trp Leu Tyr Asp Cys Glu Gly Asn Ala Pro
1               5                   10                  15

Gly Gly Gly Lys
            20

<210> SEQ ID NO 270
<211> LENGTH: 18
<212> TYPE: PRT
<213> ORGANISM: Artificial Sequence
<220> FEATURE:
<223> OTHER INFORMATION: albumin binding peptide
<221> NAME/KEY: MISC_FEATURE
<222> LOCATION: (1)..(1)
<223> OTHER INFORMATION: Asn, Leu, or Phe, preferably Leu
<221> NAME/KEY: MISC_FEATURE
<222> LOCATION: (3)..(3)
<223> OTHER INFORMATION: Ala, Asn, Asp, Gln, Glu, Gly, His, Leu, Met,
      Phe, Ser, Thr, Trp, Tyr, or Val
```

```
<221> NAME/KEY: MISC_FEATURE
<222> LOCATION: (5)..(5)
<223> OTHER INFORMATION: Ala, Asn, Asp, Gln, Glu, Gly, Ile, Leu, Lys,
      Phe, Pro, Ser, Thr, Trp, Tyr, or Val
<221> NAME/KEY: MISC_FEATURE
<222> LOCATION: (7)..(7)
<223> OTHER INFORMATION: Ala, Arg, Asp, Gln, Glu, Gly, Ile, Leu, Lys,
      Met, Pro, Ser, Thr, Trp, Tyr, or Val
<221> NAME/KEY: MISC_FEATURE
<222> LOCATION: (8)..(8)
<223> OTHER INFORMATION: Phe, Trp, or Tyr, preferably Trp
<221> NAME/KEY: MISC_FEATURE
<222> LOCATION: (10)..(10)
<223> OTHER INFORMATION: His or Phe, preferably Phe
<221> NAME/KEY: MISC_FEATURE
<222> LOCATION: (11)..(11)
<223> OTHER INFORMATION: Asp, Glu, or Thr
<221> NAME/KEY: MISC_FEATURE
<222> LOCATION: (12)..(12)
<223> OTHER INFORMATION: Ala, Arg, Asp, Gln, Glu, His, Ile, Leu, Met,
      Phe, Pro, Ser, Thr, Trp, or Val
<221> NAME/KEY: MISC_FEATURE
<222> LOCATION: (13)..(13)
<223> OTHER INFORMATION: Ala, Arg, Asp, Gln, Glu, His, Ile, Leu, Lys,
      Met, Phe, Pro, Ser, Thr, Trp, Tyr, or Val
<221> NAME/KEY: MISC_FEATURE
<222> LOCATION: (14)..(14)
<223> OTHER INFORMATION: Ala, Asp, Gln, Glu, Gly, His, Ile, Leu, Lys,
      Phe, Pro, Ser, Thr, Trp, Tyr, or Val
<221> NAME/KEY: MISC_FEATURE
<222> LOCATION: (16)..(16)
<223> OTHER INFORMATION: Pro or Ser
<221> NAME/KEY: MISC_FEATURE
<222> LOCATION: (17)..(17)
<223> OTHER INFORMATION: Asn or Pro
<221> NAME/KEY: MISC_FEATURE
<222> LOCATION: (18)..(18)
<223> OTHER INFORMATION: Asn or Pro

<400> SEQUENCE: 270

Xaa Arg Xaa Cys Xaa Thr Xaa Xaa Pro Xaa Xaa Xaa Xaa Xaa Cys Xaa
1               5                   10                  15

Xaa Xaa

<210> SEQ ID NO 271
<211> LENGTH: 18
<212> TYPE: PRT
<213> ORGANISM: Artificial Sequence
<220> FEATURE:
<223> OTHER INFORMATION: albumin binding peptide
<221> NAME/KEY: MISC_FEATURE
<222> LOCATION: (1)..(1)
<223> OTHER INFORMATION: Ala, Arg, Asp, Asn, Gly, His, Leu, Phe, Pro,
      Ser, Trp, Tyr
<221> NAME/KEY: MISC_FEATURE
<222> LOCATION: (2)..(2)
<223> OTHER INFORMATION: Ala, Arg, Asp, Asn, Gly, His, Phe, Pro, Ser, or
      Trp
<221> NAME/KEY: MISC_FEATURE
<222> LOCATION: (3)..(3)
<223> OTHER INFORMATION: Glu, Leu, or Met, preferably Met
<221> NAME/KEY: MISC_FEATURE
<222> LOCATION: (7)..(7)
<223> OTHER INFORMATION: Trp or Tyr, preferably Trp
<221> NAME/KEY: MISC_FEATURE
<222> LOCATION: (10)..(10)
<223> OTHER INFORMATION: Gln, Glu, or Lys
<221> NAME/KEY: MISC_FEATURE
<222> LOCATION: (11)..(11)
<223> OTHER INFORMATION: Ala, Arg, Asp, Glu, Gly, His, Met, Phe, Pro,
      Ser, Thr, or Trp
<221> NAME/KEY: MISC_FEATURE
<222> LOCATION: (12)..(12)
<223> OTHER INFORMATION: Met, Pro, or Ser, preferably Pro
<221> NAME/KEY: MISC_FEATURE
<222> LOCATION: (13)..(13)
```

```
<223> OTHER INFORMATION: Ala, Arg, Asp, Gln, Glu, His, Ile, Leu, Lys,
      Met, Phe, Pro, Ser, Thr, Trp, Tyr, or Val
<221> NAME/KEY: MISC_FEATURE
<222> LOCATION: (14)..(14)
<223> OTHER INFORMATION: His or Pro, preferably Pro
<221> NAME/KEY: MISC_FEATURE
<222> LOCATION: (16)..(16)
<223> OTHER INFORMATION: Ala, Arg, Asn, Asp, Glu, Gly, His, Ile, Leu,
      Lys, Met, Pro, Ser, Thr, Trp, or Tyr
<221> NAME/KEY: MISC_FEATURE
<222> LOCATION: (18)..(18)
<223> OTHER INFORMATION: Ala, Asn, Asp, Gly, His, Leu, Phe, Pro, Ser,
      Trp, or Tyr

<400> SEQUENCE: 271

Xaa Xaa Xaa Cys Ile Thr Xaa Pro Phe Xaa Xaa Xaa Xaa Xaa Cys Xaa
1               5                   10                  15

Asn Xaa
```